(12) United States Patent
Olek

(10) Patent No.: US 9,096,900 B2
(45) Date of Patent: Aug. 4, 2015

(54) EPIGENETIC MARKER FOR THE IDENTIFICATION OF NATURAL KILLER CELLS

(75) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 94 days.

(21) Appl. No.: 13/318,015

(22) PCT Filed: Apr. 28, 2010

(86) PCT No.: PCT/EP2010/055722
§ 371 (c)(1),
(2), (4) Date: Dec. 29, 2011

(87) PCT Pub. No.: WO2010/125106
PCT Pub. Date: Nov. 4, 2010

(65) Prior Publication Data
US 2012/0094290 A1  Apr. 19, 2012

(30) Foreign Application Priority Data
Apr. 28, 2009 (EP) .................................. 09005876

(51) Int. Cl.
*C12Q 1/68* (2006.01)
*C07H 21/02* (2006.01)
*C07H 21/04* (2006.01)

(52) U.S. Cl.
CPC ........ *C12Q 1/6881* (2013.01); *C12Q 2600/154* (2013.01)

(58) Field of Classification Search
None
See application file for complete search history.

(56) References Cited

PUBLICATIONS

Ehrlich et al. Oncogene 2002. 21: 5400-5413.*
Ushijima (Nature Reviews. 2005. 5: 223-231.*
Weisenberger et al. Application Note: Illumina® Epitgenetic Analysis. Mar. 25, 2008. Pub No. 270-2008-003.*
Ballas et al., "Modulation of NK cell activity by CpG oligodeoxynucleotides", *Immunologic Research*, 2007, vol. 39, No. 1-3, pp. 15-21.
Du et al., "Genomic profiles for human peripheral blood T cells, B cells, natural killer cells, monocytes, and polymorphonuclear cells: Comparisons to ischemic stroke, migraine, and Tourette syndrome", *Genomics*, 2006, vol. 87, No. 6, pp. 693-703.
Fitzpatrick et al., "Methylation and demethylation in the regulation of genes, cells and responses in the immune system", *Clinical Immunology*, 2003, vol. 109, No. 1, pp. 37-45.
Floess et al., "Epigenetic Control of the *foxp3* Locus in Regulatory T Cells", *PLOS Biology*, 2007, vol. 5, No. 2, pp. 169-178.
Hanna et al., "When killers become helpers", *Trends in Immunology*, 2007, vol. 28, No. 5, pp. 201-206.
Kishi et al., "An impaired expression of granulysin on NK cells in cancer patients", *Journal of Interferon and Cytokine Research*, 2001, vol. 21, No. Suppl. 1, pp. S109-S110, P-1-129.
Rogers et al., "A Role for DNA Hypomethylation and Histone Acetylation in Maintaining Allele-Specific Expression of Mouse NKG2A in Developing and Mature NK Cells", *The Journal of Immunology*, 2006, vol. 177, No. 1, pp. 414-421.
Rouhi et al., "Evidence for Epigenetic Maintenance of *Ly49a* Monoallelic Gene Expression", *The Journal of Immunology*, 2006, vol. 176, No. 5, pp. 2991-2999.
Siu et al., "Aberrant promoter CpG methylation as a molecular marker for disease monitoring in natural killer cell lymphomas", *British Journal of Haematology*, 2003, vol. 122, No. 1, pp. 70-77.
Turman et al., "Characterization of a Novel Gene (NKG7) on Human Chromosome 19 That is Expressed in Natural Killer Cells and T Cells", *Human Immunology*, 1993, vol. 36, No. 1, pp. 34-40.

\* cited by examiner

*Primary Examiner* — Carla Myers
(74) *Attorney, Agent, or Firm* — Saliwanchik, Lloyd & Eisenschenk

(57) ABSTRACT

The present invention relates to a method, in particular an in vitro method for identifying natural killer cells of a mammal, which often express the surface proteins CD 16 and/or CD56, comprising analyzing the methylation status of at least one CpG position in the CX3CR1 and/or FGR and/or NKG7 and/or GNLY genes, in particular their upstream regulatory regions, and in particular the promoter and other conserved regions of the genes CX3CR1 and/or FGR and/or NKG7 and/or GNLY, wherein a demethylation of at least one CpG in the analyzed sample to at least 70% is indicative for CD56 expressing NK cells, which might also be CD8+ or CD8−, CD56 dim or bright, CD 16+ or CD 16− NK cells. The methods of the present invention are useful for the detection and quality assurance and control of NK cells. Furthermore, the present invention relates to a kit for performing the above methods as well as respective uses of the inventive methods or kits. The present invention furthermore provides an improved method for analyzing the methylation status of at least one CpG position in the gene CX3CR1 and/or FGR and/or NKG7 and/or GNLY genes that allows for a precise analysis even from sub-optimal quality samples, such as non-freshly obtained blood, tissue or serum samples.

11 Claims, 4 Drawing Sheets

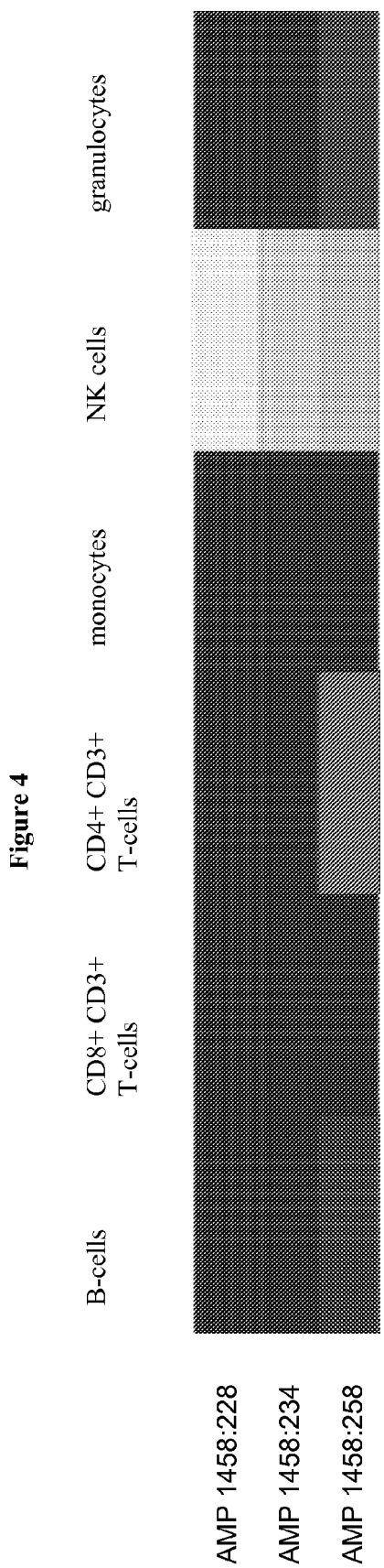

SEQUENCE LISTING

```
<160> NUMBER OF SEQ ID NOS: 181

<210> SEQ ID NO 1
<211> LENGTH: 34514
<212> TYPE: DNA
<213> ORGANISM: Homo sapiens

<400> SEQUENCE: 1
atggggtctc actatgttgt ccaggctggg tctcaaactc ttgatgtcaa ttgatcctcc      60
cacctcagcc tcccaaagca ttgggattac aagtgtgaat tactgcagtg ggccattcca     120
tgggcctttt gcagagagcc tgcataacca gctacatttc ctgctgtagc tatggccagc     180
tcaggaatgc accactctgt gtttgctttc ctctttccct gcctcacttc acttcttcct     240
gcactttgtt cctgttgaat ttcacattct gatatggcat caccatgcag gctttgcctc     300
agcctctgtt gcctagggaa ggaactaagc aagccctgat ggaaatggtg ctattccttg     360
aggcccagtt gtaacgcaca ttcctccaga ggggacttgc ctttacttca cccagtactc     420
tggggtactt ccaacctggg acctctgtgt ttgattggct ttttggccac acaggaagtg     480
tgaaattcag ccccaatatg catgaacaca ggtttgtggc tgagagttct ggagaggact     540 tttcttttt tctactcact ggagccaaag ccaatgtagg catcgttata taatttcccc      600
```

```
tctgtgtgga aatgagactg gggtgggact cttacttcac ttacaaaggg agctccccttt      660 tggggatact ggttttgttt gggcttcaga tagaatctca cccttcctag cccagaactt      720
gtctttgtct tccacgttgc aggcacatga cccatgaagg ccaggctccc ggccttaagg      780
ggccacagag ggcccagggt gaatgtgagc tccagccttt ccttcaccca gcagatttgc      840
attctgcctc tgaggatttt cttcaccttt tttccagatc aaccatttat ttaaaaaggt      900
atttttgagt aattatccag catcctaggt gttctatatc aggaggggt cctctagaca      960 ttcttacacc tctattatct ggaaattgct tcttttctcc ttttttcccc tctctccctc     1020
tttcttttcc acaggccata gtcttccatc cctcccagga tatgacattg gtatgtctca     1080
gaggcttcca gacagactca ctggaattca agttctgca tccacccta gcctagctca      1140 atacttcatg cagtacatct acaagagaat gccctgtctc ctagaactgg gtgatctggc     1200
aaacagaggg catgcacacc agcggtgtag agctggagag gttctagggg agaacatggt     1260
cacttcctct tattgtacac agcagcaaac tgaggcacag catgttaggg ctcagcactc     1320
cagccagcca gaacctgctt ctgacataca gctgtgagaa gggttaaaag aatgactaaa     1380
aagcagtttt taaatagct gtcaatttct actcccagtc aatctgtgca cagctcttat      1440
tcaccgtgaa gcgaaaacat atacaatgta ctattcactc aaagtgaaac tccaaatgaa     1500
gtcatacatt gaaccccagt atcgcccatt gttaggaatc aatgaccctg agtaaatgga     1560
gtttcatgaa gcctctgtgt gccagctgtc catgggaggg ggtttccaaa ggcctttctg     1620
gttggtcctg cagcctaggt gtcacttgag tgggtatgcc tttgtggcct ggtcattcac     1680
agtgtggaat cttcaaagcc taccagtgcg acgtgagttt tatgtgcaaa gctgaattca     1740
aggaacccct gagatggttc atgcagtttt tccctctgag cctccagtga taactccaga     1800
cagcacaggg tcaggtgttg cccctgtgt ctggctgcct tacccttgc ccagaacaag      1860 agtagggccc acagacattt cccaggacac tggggagcct gtcatgtgga cttcctggct     1920
tcatccttcc cccagccagg gcctctgacc tctccactcc tgtgtccctt cccccaggag     1980
gatctctgcc ccactcagta tccggcagat cccttgttat tcttgtgctt ttagaacttt     2040
tgctgttttt ggccaacttg aatcaacatt actgtctcct cgagcgtttc tctgccaggc     2100
aggggactag gaaagcagga ctgcagggcc tgctcattgg gttctaagat gtgggtgaat     2160
tcggagtggg gttgtgcagg gctcccactg agaggagggc aggggcccct tgtgaagtgg     2220
ttagctcgtc ttgtcaatag gtcctcagaa catcccttc agtctcttct caaagaagcc      2280 cttttcaaacc aggcccttgc tcttctgtga tcgaagtgct tgactttttc tgctgttgct    2340
cacatccggc ctgtcaaggt tgttttctgc cagcctggtc gtccatgcac cccatactat     2400
tctcatggac tcatacccgt gaggaattgg gaggtaaggg caagcacctc agcacgctgt     2460
gtgggacccc tagggttgca cctgggagga gcaaggccac acggacctgc tgtcagctcc     2520
tatgctccca tctggctgga accaacccca agcttggggt tcagtgcccc cggcccatgc     2580
actcagcatc tacacccatc acccacctgg cctcctggtc ttctgaccct gggatctccc     2640
aaagaacaga gcagagccaa ggctggccag gatgagcgca gtctctctga gatgggacct     2700
gaaaacaggg gcacccttgg caaggaagga ggcacacaga gtgggaagca gccaggcctg     2760
gcttcgagtc ctgcctgggc actcccccac aaggagactg tgggcaagtg acttcccttc     2820
ccaagccgct gggctgctcc acagcagaaa tgtggcagtg gcgcacccct gaaggttgcc     2880
gtggggagtg aggataaggc atgcagagtg cccggctcag actggatgac gacgacggcc     2940
agtggcaact tctctcctaa ttgtgcaagc aagcagtcat ggacaaatcc ttgtgagagt     3000
```

```
gactgtgtgt acaccaggac acagctgcac aaacaccatc cctaccctca taatgctcca      3060
gtttagtggg ggagacagac attaaacaca tccacacata agaggatggt gatgaagtgt      3120
catcaatttc acaaagaaga aataatggac tgagataatt gacagagtgg gggacctaat      3180
atagcttagg gggtcacagg aggtctctat agaacagact tgctgcctaa ggagctacct      3240
aagtagtgag gatggagggg aaggggtcaa ggctggagaa agcttagggc gtttgagaac      3300
tgaaatgagt tcatagtggc tacacgtacc cggcccatgt aggtaattta aaatttcctg      3360
gtgtgattga aaaagcaaag ggaaataggt aaagttaatt ttaataagat attaaatgta      3420
aggcatctaa tgtaaggcat attatatagt ttcatcatgt cattaacata aaaattatta      3480
atgagatagt ttacatttct ttttaaatac tgagtcttta agaatctggc aaatatttta      3540
catttatatc acatttcaac tgagactagc catatctcaa gggctcaata gccacatgtg      3600
gccagtgacc atcgtattgg acagcacagc tccggacatc ataatattgc aaccactact      3660
cccaggaaag actggttcac tggcacaggc ttcagacacc tgccagaagt gctttagaac      3720
aatattccag gaagcagcta gcacacacag cagctttacg tgaattacag ccaggttagg      3780
tcataggctt ggcctagagc ttgacctaga ccttagttca ctctcatagt acagcaagtg      3840
catacccct ctcgggggcc ctgagtatgc cctcattagt cttccaaca tttttacccc       3900
aaagaactga ctgtaactgg tcttttgttt tgttttgttt ctagctatat cattacctcc      3960
agatattgaa agaggacatc tgaacctgtg tgatgttgta gaaagaagat tgtctagggt      4020
gtcaaagcag acagatgcca gtttgtgctc atcctttacc agactggtgc ctacagtgag      4080
tcacacttgt taagtacagt gtggtaagta agaattcagg ttccagagtc agactgcagc      4140
tccagttcct gaactgtgta atttgggaga gacactcagc ttttctgagc ctccttatcc      4200
tcatccgtaa aatgaggaca attactagca ttgctggagg attaaacaaa ataataaata      4260
gaaggcactt acttagcaca ggtcctggca catggtaaac atttaataaa cagtgtctat      4320
tactatgttt taactgttat tatctctgtg cctctgtttt cttggttttc aagtggagac      4380
aatcatccct aaaaaaccct gctttgcagg attctgtgtg gcttatgaga gatgaggagt      4440
atgaaaacac cttgtaaaac caggaggccc tttacaaagt cagaagcagc tcctcggtgc      4500
tacagtctag ttgagggtct gactttagga agtcacaagg aacttagaaa tgggaagggg      4560
cttccacctg acaacagcag ctctgccact ggaccgggtc ttccagccta gctccaccac      4620
tcttctcatg ggtaaactct gccttcatct ctgttttctc atctctcaca caggctgaga      4680
acacccagct ctcaggctgc cgggctgagg gtcaaatgag tccctgacca tcacgtgcac      4740
agggcctgac ccaaggcagg tgctcaatcc ctggcacttg ctcttgttgc cttagagggg      4800
accttgctgc ccacacccgt ctcagcccag acctggagca gcacttcatg tgattaccac      4860
aagggggcgc ccctaagctt tccattcact ggaaccattt cattgaacct gtcattcagc      4920
ccttccttcc acatccctac tgctatccta gagccaggaa aaagcccttt agaaaggagc      4980
tctgcagacc ccgaaggcat ctgctgtagg ttcagtgact cttagagaaa cagccctgct      5040
ttccaaggcc aaaacactgca tgtaggtaaa tttgtgacct gtggtggccc tcccaccaac      5100
ctatcagctg agtgtcttca agttacttct ctaactttct tgggcctcag tttcctcacc      5160
tgaaaggaag agttggaaat aatcactctt ggtgcctgtg ggagtgcttt gtaaaccatg      5220
gagtgagctg cacatgtgtt tcataactgt ccttttcatt gttcctataa accaaaaagt      5280
atctgagaca ggtctcaata aatttagaga cttagtttgc caaggttaag gatgtgcctc      5340
```

```
ccaaaaaagg aacacaaaat cccaagaaca acctgtgatc tgtgcttttt tccaaagagg    5400
attttgagtg cttcaatatt tgaagaggac aagtaggcgg gagggaaag agggagcgta     5460 tggtcacatg tatggtcaca tgactgaatc tacatgttgc acgtgaaaaa aggcagaata    5520
ccaaaatagt caattatggg ctgggcgcag tggcttacac ctgtaatccc agcactttgg    5580
gagacggagg ctggtggatc acttgaggtc aggagttcca gaccagcctg ccaacacgg    5640 tgaaacccca tctctactaa aaatacaaaa actaggtgga catagtggca ggcccttgta    5700
atcccagcta cttgggaggc tgaggcagga gaattgcttg aacccgggag gtggaggttc    5760
cagtgagctg agattgcgct attgcactcc agcctgggca acaagagtga aattctgtct    5820
caaaaaaaaa aagaaaagaa aagtcaatta tttattcatc tggtgttcag caaatgttta    5880
cgtaagataa agtaagcata gggcagctac ctgtggagac acctggcctt ctatctgact    5940
gttatttttt tgttgttgtt tatttatttg tttgagtcag agtctcgcag tgtcccccca    6000
ggctggagtg caatggcgcg atctcagctc actgcaacct ccgcctccca ggttcaagca    6060
attctcctgc ctcagccttc tgagtagctg ggattacagg cgccaccac catgcctggc     6120 aaatttttg tattttact agagacgagg tttcactatg ttggccaggc tggtctcaaa      6180
ctcctgacct cgtcatctgc ccacctcggc ctcccaaagt gctgggatta caggtgtgaa    6240
ccactgcgcc cggccctatc tgacctttta tctgtagcta tattcttagg aacaaaagga    6300
aggcagttta ttctgtgact cagcttccag cttaatctct ccctttggca tagtgaatga    6360
aggtcccgag attttatttt cctttacat tcacatttag cagattgtac cacttgggat     6420
tccctaatat gaaaaagaa agtgaaaact tgcctgtcag ctgccagact gtgatgttcc     6480
cacacactgt gaccatgttt ggaaaaggct caagaagac cactccacaa ccacaaaact    6540
aaacatcccc acctctgatc ggcatgaggg attgctgctt ctttagcaat gatgactcta    6600
gcccacttca atccccccag ataaaatcca ctaagacact cagtcactga actgcccctg    6660 tttttgaca gtgcctgatc tagaactgcc cctgcttcct gaatcctccc ttagacgtgt    6720
ccagcacaag ccccagctcc ccattaagga catgctccct ggttcctttg acatgtgtct    6780
tcccttgccg cagtaagcta aacaaaccta acttttaaac tctagatgtt cctcatggtc    6840
ttcagcccac aaactatgag aaataatttc accctgatta attgacatta actttggggg    6900
tcagtctcct tgggctttca taacaaaata ccacagactg ggtggcttaa acaatagaaa    6960
tttatttctc acagttctgg aagctggaag tctaagatca aggtgtcagc aggcttgatt    7020
tctcctgagg cctcactcct tggcttgcag atgccgcctc cttctctgt gcacatacat     7080 ccctggtgtc tctctcttct gataaggaca ccagtcctgt tggattaggg tcccactctt    7140
ataacctcac ttaaccttaa tgacctcctt agaggcctca tccccaaata tagtcatatt    7200
gtgggttagg gcttcaaaat atgaatggga gttggggaa acataattca gtccatatac    7260
ttggatttta atttttttct aagaatagtt aaaaggccat tcaggagagg agggacaa     7320 gattgcccac cagtttcaag tagaaaaggg agttgtcact cagaaatttt tgccaagcaa    7380
gtggagtaag agggaaccag gaccagaaac agtgcaatga gttctgaagg acagctgcg    7440 cttcagcaaa gctccagaga gcccagaagg aggctactct gagaggctcc actaatgagt    7500
gaggctcttc taccctcttg acctttgta caacttggtc cctctcctgg cacatcctgc    7560
ccaggtgaat gcatccacca agactcttag gaagagattg ctccttcttt gtatcccgg    7620 aacacagatt tctattaccc tcattaccct actcagcagca ccatatgaag tgctttacac   7680
atgtcaccat taatcctcat gccgactttg ccatataagt ttaccctgat ttttttttt    7740
```

```
tttagatgga gtctcactca ttgcccaggc tggagtgcag tggtgcgatc tcagctcact   7800
gcaacctcca cctcccgggt tcaagtgatt ctcctgcctc agcctcctga gtagctggga   7860
ttacagatgc acgccaccat gcctggctaa tttttgtact tttagtagag atgtgttggt   7920
caggctggtc tcgaactcct gacctcaggt gatccgcccg cctcgacctc ccaaagtgct   7980
gggattacag gcatgagcca ctgtgcccgg cctgccctga ttttaacaat aaggaaattc   8040
aggcttagag aaatatctcg ccctaagcca cacagcttga gagtagcagg gtcaggattt   8100
gaaccaggag agtgggattc caggtaattg tgggccggct ggctcatcac aaaactgtaa   8160
cccaaaggct tgccagattt gcctgcacac accacttcct ctggggaaat gcagctacca   8220
cagatgactg tcagcaaagc caagtgtttt gagtaaaacc aatgaaccag aggggagctc   8280
tgaagccaaa gggctgccca ccaggtgggg ccatctctgc tgattggctg ctccgcctgc   8340
tgctcctgga cctgggggtt gctggtgaga gccagagaca ccaggagggg gagacagagc   8400
tcaggggata gaggcaaggc agctcactcc tgtatctgat gactgtagat taccttaagt   8460
ttcctgagct acctggaaga gtggaagcca aagcgagacc attaagggaa agggtagaga   8520
ccctgcccta ttcatctttg tatccttaac aaacagccct gagcagaagg taggcaggca   8580
acatgtgctt tctaaatacc tggcaagtga gtgagcaagg gtcaggttgg agatgcattg   8640
cttgtgtaca aaagtgtgac acataatagc ggcaattacc aataactatt aagcagtata   8700
tggggcaagt gatggttcat ttgggaataa agaggcactt ttgttttagt ctgcaatgag   8760
ccttttagga cttctgcctc aacatactga ggtttaaaaa taattcaacc caagctaggt   8820
tcccagagaa tgacagacac attttcacat atgaatcaca gatggatttc acttatttaa   8880
aacacacaca cacacacaca cacacattaa atcatctctc tcacacacac acatacgtga   8940
gcttttgaat atgacaactg ttgcttaatt cacatcctaa gttgcttcct ttggtgaaat   9000
gtcaccatcc aggaattata gccatgttgc cgaatgtgtg atttcaacaa acatcagctt   9060
cttcctggga cccagacata cacttaagct atagaatatg tactggcttc aaggaaatat   9120
acctctcagc ctcttttgca tgtgggtaaa attaactcaa cattgtagat ttacaaaatc   9180
ttgatcattg atctaaaaca cttttgaaag gagaatacgt gaaccttcca tttgacccat   9240
tcaaattatt gaaatatata cctccttgtg cccaattcag tttcaaggat attccaaatt   9300
tgtcgaaaat aaatgtgctg aaggcactaa acaatctga agtccgttta ccaagcagag   9360
tgtcagaaac tttggagtga gcatggcatc tccatttggc tctttctaaa ttgaaatgtt   9420
actgcaggtt ccatcaccaa gtgtattgac cgagtgaaat gactcagcac tgcttgctgg   9480
acaccaaaca ctccctcctg gccaaacggt cacttgagga cctaccacct gctctaccaa   9540
ctacatctgc acgacagtaa acagcaaaat aaataccttc tacagccaca tatagattag   9600
gtcttcatta ccttaaacat agataaaact gtgagtgtga tttatataga caagagtctt   9660
ttggcagcta gatcaagcag aaataaatat tgatattttg ttttagagtc aaggagatta   9720
gaagctggct ctgaataaaa tacagattgt tttacttagc acagccattt tgttgttgtt   9780 ataaagaat agagatggac aaaagtacct aagaaagggc ttcttgctat aaccacaggt   9840
tgacggctgt gcaacactct ccagcccggc ttccctgtat tcacttgtag ccacaactac   9900
aatttcatac tgtttaagtt ttcattgaca acggcagcca aatatctgct tatttcagat   9960
attctgaatg ctaagaaagt agatggtcag atgtttcttt cacagccttt gctatgtttg  10020
catcttgtac ttttgaaaca agtttcagtt caggtaaagg attacttaat cctctaaagg  10080
```

```
atgaaaaagt gtagctgagg tgtctaaaat tcttgattca agtttgtcca actgagagag    10140
tttatcagga gctaatttgg ctcacactgg acccagaatc ccaccccca acttcatttg      10200 tggtccaatt atagtctttt tttttttttt tttttttgag acggagtctc gctctgtcgc    10260
ccaggccgga ctgcggactg cagtggcgca atctcggctc actgcaagct ccgcttcccg    10320
ggttcacgcc attctcctgc ctcagcctcc cgagtagctg ggactacagg cgcccgccac    10380
cgcgcccggc taattttttg tatttttttag tagagacggg gtttcacctt gttagccagg    10440
atggtctcga tctcctgacc tcatgatcca cccgcctcgg cctcccaaag tgctgggatt    10500
acaggcgtga gccaccgcgc ccggcccaat tatagtctta tattaaacag tatccactgc    10560
agctcccaaa tatccataag atcacctgtt attagtctct tcgtgtcagt gaacctgctg    10620
catttgtgtc agcaagtgca aggctgcctc tggacgtgtt cctcacctct gcactgtact    10680
ataagcccct tggcttttgt ttttggaatg acccttttgaa ataagtaaaa tcctgaaagc    10740
aatagtttag gaaatctacc tgtcacttct gtagtcatac aatgccacat gtaaggttat    10800
cttgtaggtg cacttatacc ctggccagct ggctaatctg gcagcttatt ttcaatatc     10860 tggccaatga tacagactca tgagttctga tactttattg ccctagttat ttaacgttat    10920
attatctgta cagcgaggac agaaaaggct gttttaaagc tgtttgtgag agacaactat    10980
tattttcctt attttttaaa gcagactctc cataatatca gcaaacaata taaagacatt    11040
ttggcaatta atttgaatta cctgtgtatt tcaaagggct aaaatgggca tgttttaaaa    11100
ttcaagattg tagttcattt attcattttc cattattctt ccattggtaa gttccacttt    11160
aatgaaaaca catgccatat ttggtgagag agcagatttt ttaattttta attttttaaa    11220
aatgacatat actgtctgca gacagatatt tttaagtatt gcaaagcaaa agttgaatga    11280
tgcctaaaaa atagtttatc ctaagtactc ctggagttcc ttgccagatc ctgttttgcta   11340 tggttccaaa ggggaagtgc ttttaatcac tgttgagcag aatttatgaa acaaacctga    11400
aaattgccac agatgatgtt aaatgtaaac attgggacag aaggaggtag taaatagcac    11460
ttactttgtc tacatttact cctctccaac tttccatttt tcttttcttt tcttttaaga    11520
gttggagtca ttcttcacc caggctggag tacagtggca ggatcactgc tcactacacc     11580
cttgaatcct gggctcaagt gatcctccca tctcagcctc ccatagctgg gactacaggt    11640
cggcaccacc atgcccagct atttttttt tttttttttt ttctgtacca atgaggtctc     11700
cctatgttgc ccaggctggt ctcgaactcc tggactcaaa tgatcttccc actttggcct    11760
cccaaggtgc tggaattaca ggcatgagcc acctccaatt ttctattggc ctctaatttt    11820
ctaagtctga tcttttctcc tcttagaggg agaagatctt ttgtcctctt agggtagaag    11880
aggaaagaga gactttttt ctgcttctga aatctcccag catattgctt tcgacttgtc     11940
aatggcaaca cagcctttgg atgctcactt gaccctcaac gtgtctggtc ctttacaatt    12000
ctatgcattt tcctgtagcg agatcccttc tccgtcttcc accacccact gctttggctc    12060
ccctcttgct gttccctgcc tgcatctggg caggaagttc caatcctgac ttgaccctt     12120 ttcagctgtg tggcctagga ctcattgctc ttttctcccc atttcatcat ctgaaaatgg    12180
aaaaaataat acctgactag aaagtgaaag taaaaaagag atataatgga caatgtgcct    12240
cgcacagggc ctggcatgga gaagtccttg atgtacgtct tttccttccc ttttatgcag    12300
ccgtttccct cacacccacc cattgattga ttttctgaa gagactactt ttgtcatgtc     12360
accctctaat ccccagactt taaactggga ggtagcagag tggtctgatt aagacccttag    12420 acaagggttt cttgtctggg cgcagtggct cacgcctgta atcccagcat tttgggaggc    12480
```

```
caaggtgggc agatcacttg aggtcaggag ttcgtgacca gcctggccaa cgtggtgaaa    12540
ccccatctcc actaaaaata caaaaattag ccagatgtgg tagcaggctc ctgtaatccc    12600
agctactcgg gaagctgagg tggaagaata gcttgaaccc aggaggcgga cctcagcact    12660
tctgcctggg tgatgggagt aaatcctgtc taaaaacaaa caaacaaaaa aaaaaaactt    12720
agacaatggt ttctcagctt tttttaatca ctccccaaca agtccttttta gatattatat   12780
tcttttgtgt gtggcggggt acatagcgtg tgtatatgtt tgtaggttac atgaaatgct    12840
ttgatacagg catgtaacgt gtgataatca catcagagga aatggggtat gcatcacctc    12900
aagcatttat cctttgtgtt acacacaatc caatcatact cttttagtta tttgtaaagg    12960
taaattaaat ttttttttact atagtgcccc tgttgtgctt gtaaatacta ggtcttattt   13020
attctaagta ttttttgtgc ctattaacca cattatatat atatatatat atatatatat   13080
atatatatat atatatataa tttttttttt ttttttgagat ggagtctcgc tctttcgccc  13140
aggctgagt gcagtggcgc tatctcggct cactgcaacc tccaccttcc ggtttcaagc     13200
gattctcctg cctcagcctc ccaagtagtt gggattacag gcacccgcca ccacgcctgg    13260
ctaatttttta tattttttagt agagacaggg tttcaccatt ttggccaggc tggtcttgaa  13320
cccctgatct cgtgatccac ccacgttggc ctcccaaagt gctggaatta caggcgtgag    13380
ccaccatgcc tggcccacat tacattctta ctcacctccc cctaccatgg aattttattc    13440
cacagatatg ctattggttt agctactata tgtatatctg tgttttatac ataaagcaca    13500
agaaccttcc agaaccaatt ttcgccacct tggaagtaat accacctcta ctaagaatgc    13560
acagcataga ccataaaacc tcaatgctaa gttcaaatat tggccctacc acacatgagc    13620
tgtgtggtct tgtacaagtt acataacttc tcctccttgt ctcaaactcc tcacatataa    13680
gatgaggata ataatagtac ctgcggccac acacagtggc ttaaacgtgt aatcccagca    13740
ctttgggagg ctgcggcaga aggatcactc aaactcagga gttcaagagc agcctgggta    13800
catggcgaaa ctctgtctct acaaaaaata caaaaattag ctgggtgtgg tgatgtgtgc    13860
ctgtagttcc agctacttgg gaggctgagg tgagaggatc gttcgagccc aggagatcaa    13920
ggatgcagtg agctatgatc atgtggctgc actccagcct ggataacaga gccagaccct    13980
gtctgaaaga aacaaaaaca aaaacattag cacctgcatc atagggtcac tgggggcact    14040
acatgagttc atgtacatcg aggacttagg acattgcctc aggcagacct agtgctgcac    14100
aactgcttat gtaattattc ccaaatttct ccagggccca cagaagaaca tggaagtatc    14160
ttggtttggc aattaaggtg aatcacattc tcactctcct tttctgcatc tctaccccac    14220
attcccacaa agctttattc acaccaagtc tccagtcctt gcctgcattg tgtgatgggt    14280
gcctgcagta tggggtgggg acacccatca ctgtccaggg tgtccccacc atcctcacag    14340
cctctctgtc tggcctcctg cctttgagcc agcccaccac actctcattt ctctgcccag    14400
cagaaaccaa actgtcctct gcatttactg tctcaactgg aagagaaatg cagaatgaca    14460
aagaacttgt gaacaagggt cagctccaac agagagtgaa gccaaggggg ctgggcagaa    14520
agagagatga agacggggat ctaaggaata aggctgtacc agagtgagag tacggggggag   14580
gggttgaaca agagttcagg gaggagagaa ttcccagcgc tgagccagag actcctttac    14640
agaggcccaa ggaggcgtgg agggaggggg aaggctgcca aggctctttc tgtctccatg    14700
agtgtgtcaa gaatgcaaag cactaatgct cttcacttgg tccatcttgc agggttgagt    14760
ttgcagtgag caaccttgaa ggatgagctg acatctcgct cagggccaaa taaccgactt    14820
```

```
gcttactgct tgctataaaa tggcacgtta cccaaggtca gagttcccctt cctataaccct   14880
ccccatccct cacacattca caggtatcta tccaagccat ggcatcactc tgtggggctt    14940
gggggcaagg caactgacac tggacgctgg ttctcatgct tgccaagcat gaagccctgt    15000
gctgctagca gctgtggaac atagccgtta gctttaaaag agggtaaaat cacgtcctgg    15060
acaggacagc caggtgagtt gggaagggaa gagagcctgc cacgggcaca ggcatgttgg    15120
gggaagtgga agtggtgaga gcacagtagg aagtgagaag gggcgggccg tgcttaccag    15180
gccgtggact taaaccagga tgagagaacc cctggaggcg tttaagttgg cagacttgga    15240
tttcaggaag agctctctgg cttctgggtg gagaatggcc agtggggtaa gtggtgagag    15300
gaaagacaga gaacggagaa ggttagatgg gcttgggaaa ttatccaggc cctggatgga    15360
ggtagagatg tgtgctcatg aacacggagg ggattactga tgtggggtgg atgagactgt    15420
cgtcaagagt gtgggacagg aagagaggga gagtcttggc cagatccaag aaaggagccc    15480
tcagaagagg aggggagtca gaggcaagga aggggctgag gcagccagcc cagctgagtg    15540
gaccccagga gaggtatcaa ggggtggtgt ggggtgggga ggggcagtg tcagaaagtg    15600
gatggggagc ggcctgactc tgcttttgtc ctgtggcctt ctggccaaag gcagggaaag    15660
gtggccaaac actgagacca agaacaaaga aagaaaactg ctggtggact tcttccacca    15720
tgagcaggcc accaagcccg cagcactgca ctgcagcccc cagctctgtc ctggggttgg    15780
gggaggtgag gaggggcaag gtggggagca cacagagcac ccgctgtcct cggaacacca    15840
cagcgactag aggtaaggga gcaccggatg tggctgggat gtgggcagca aggggccaga    15900
ggggccttga aggggtcaca gaccatttaa tgaaggtgta ttgaaggcca ccatgggcca    15960
ggccctagtt agggatggat cagaattata tagcatatgc caggggtcag gcaggtaatg    16020
aagtgatcgg aagtgatga ggcagtggca gttgagattc acgttgcagt cgccccaagc    16080
tggccaggcc agggagcaga agcatggctg gatgccggag cccaccaggc tccccactgc    16140
agggcaagag tggcagggg agagactgtg aaaggagcat aggccaggtc ctgggtgaaa    16200
gctgtgtcct cagccttgac tgatgggtat agggagccac taaatgcctt ggggcagaga    16260
ggtgaggaaa aaaatatttta ccgagcatct acaaggtgca aggtactcac tagatgcctt    16320
cagtaccaaa gcttctcaaa cttagtatgc atatcactct tctaagaatt tcattaaaat    16380
gcagattcta attcagcaga tatagggcag ggcttgaggt gctgtcttta ataagctccc    16440
agtgcctggg actgcacttt gaggagaaga gctgtgtgtg cccagtgtg gtccagtgag    16500
tactctgggc tccctctcgt gggcagggaa gctgagggcc ccatgagctc tcccagcttc    16560
ctgaaggctc cccattaatg agagctgact gtgctgtgct ttgctgactg cagggcctgc    16620
tccctgcccc ccacctccag gttggggtaa gtggcacctc tctccctcca gctccgcagt    16680
cttccctgag gtttagatct tccaggttta aaagtcagg ccctcctgtt ggcagctggc    16740
ctccaccctg gagtatctga gcttgcctgt ggcagcatct aaagatagtc tcccttacag    16800
gaaacaagat actattggct aactctgcaa ataaatgct cttagaggga aggaaaggga    16860
aatactcgtc tctggtaaag tctgagcagg acagggtggc tgactggcag atccagaggt    16920
tcccttggca gtccacgcca ggtaggtgca caggactagt tgggtacctg tgggtggggt    16980
ggagcagtgg acagctaata ggttaataat gcctgtttgc ttacgtgcag acaatggaaa    17040
ccattttcct ggggatgttg tagcctaaat atgtccaagg ggatggaaga gtgggaggca    17100
aggggtgatc agatcattta taatacactc aacctggtgg aatagtatta gaagcattag    17160
taattacatt ttagagacat ggagaaaagc tcatgatttt aaactaactg aaaaaagcat    17220
```

```
gaaaaattgc atctggatgc tgttgaggaa ttattgctaa ttttttgaga tgagaaattg   17280
tattaaagtc ttttcaaaa aagagtcctt aacttttaga gatgcacaca agtgtttatg   17340
ggtgaaatta aataattcag tagagacatt aagtgggaaa tagaggaaat attgaccatg   17400
ggttgctaat agttgaagcc aggtgttggg tataaggagg ttctcgctgc ttttatttga   17460
aaagttgctt tttatttgaa aatttaataa taaagagttt ttaaatttgt atctgtattt   17520
taatataaat ataaatgcac ttaatataaa tataaaatat gtaacatt tagatagaga    17580 aaagctaaaa gattactgtg gttgattcta ggaaactgca ttgcagatag tttcatgggt   17640
ttttttttcc tttttcttcc acttttttgta ccatctatgg gtttttgttt gtttttttgtt 17700 ttttgggttt tctttcttgt ttgtgttttg tttttttgaga cggagttttg ctcttgttgc 17760
ctaagctgga gtgcaatggc acagtctcgg ctcactgcaa cctctgcctc ctgggttcaa   17820
gtgattctcc tgcctcagcc tcccaagtag ctgggattat aggcatgtac caccgcccgg   17880
ctaattttgt attttagta gaggcgggt ttctccatta ataaattcct ggcacaaatt    17940
tagtgttcaa ttttgatata tgttgttata accattgtga ggatactcag gctcaggttt   18000
gtgtgggtgg aaaacatggt cttcagaaag aaattatgag tgcaagacag gaggaaatcc   18060
atcagaggcc ccagctgagg actgaccacg gcttgttatt tctcttgcct tgcctctggc   18120
aatcacagcc tcacagagcc tgcaatcctt gctttgtgag tttatagctc agtccagaga   18180
atggctaaga aagtttagga ttcttcaac acccactcca caaaaaaaa aaaaaaaag    18240 aaagaaaaa aaaattaatt tttgaaatac ttgaggtaga aaacttgagg cagaaaaaaa   18300
ttgagccaaa aaaaaggaa aattgaacca cgtgaaagca ggcaagaaag cttgcattgc   18360
tcagggcatc ccaggcccag agggcgcttt ggagggagct gggtttcctg agaggaggca   18420
gggtgggtga cggacctgtg ctggagagcc ttgaggacca ctgtgggttg ggaatggggg   18480
cagtggattg gggttcaaaa cccctgggaa tgagaaatgg gctcaggaag ctagggtgg    18540 attctttcat cttcctcttt gcttggcttt atttttcacaa aggaaggcag ggcaggaaat 18600
agtctcagcc caacttcagt gtggttcttc ttagtgctca ggcttacctg gcacttgcca   18660
cacctctggg atgggagcac ctactatcca tcagccacgt gccagtctcc acaaagtctg   18720
ctcctgaacc ctgctcctca gctggcccca cttcacagat ggggacatag gcagcttggc   18780
tttggaatga aggaatgaag tcaggaatga agtcctggct ctgcacttgg tgactgtgca   18840
ctgggcttgc taagtctgtt tcctgctttt aaaatggaga ttgtccatca gcctttgaag   18900
ccatgtaatg ggtatgtgtc aactttctgc aaggattaaa ggcatggtat aggaagtccc   18960
aaacacactg cctgacccat ctttgatgct caagaaacga tatatgttgt tgtcatgagg   19020
aaactgagcc tcagaaagtt tggatacctg aaaaacactg actactattg aatgaggttg   19080
tgaagaatcc agagctgtag gggcaggaaa gcaaagaacg tattagagct gacccagtca   19140
ggacgatcgt ctatcccctt cctcacccca cccatccca ggaggaagcc tgcccggccc    19200
taggcagcta tggcacagtg gcaatgtcag gtatggttct ccctagccag agaccctagc   19260
ctcaaaaaac ctccttcttg ggatccaggc atccaactgc tcctcccag ccccagcctc    19320 tgacccagta tcctgagtcc agagacgttt ggaaccagca cctgtaatgg aggagctgaa   19380
caaggagggg aacttctgct gctccacagc aggtcacggt cataggaggg agtggaacca   19440
gaatggcaga atccagatct tggctgcctt tcccaaggac ttgttctgat tcctagcagc   19500
acagcccagg cattccgaga agttgggctc tctggcatca ctcactctgc ccagaagagc   19560
```

```
caggggaaag ttggggcttc tagctgaacc ttgatcccac ctgccctctt gagggctca   19620 gaatctgctg gctgcttcac aggtgggatt ctcacggcac gctggccaca gctgatgctt   19680
cgaccccctc atcttgtttg gccaaagtgc agctttttag cttgtgagta aggaagaaaa   19740
gctgtatcat atgtctttaa acatcttcct agaccacctt tgttttcccc ttaaagtgtg   19800
cttaaggaga aaatggaaag tctcttttca gtgtgttgta ttttgtttat tgcaaaatac   19860
aacacactga agaacaatg tctgggttag caaagtatta gatttaattt cccacattac   19920
taccatccag gctgagaaag agaaccccag aagcctctct catgtccctt cctgaccaca   19980
gcctcttcct ctcccacaaa gaaccacaag tctgacttct atggtgatca cttccttgct   20040
tttccctata gtttgactga atctaaatat catccctaaa caatatagct tagctttgcc   20100
tatttttgat cttcatattt ggattcatac ttttggttt ggctcaagac taaacttta    20160 aaatgcatcc acgttgtagg agatgtacat gcacaaaaat tttcacggca acattgtcca   20220
aactagcaac aaactgaaag ccacctatgt gtgcattagc agtagaaatg gcaataaatc   20280
atggactagt cacacagtgg aatcctacgc agcaaggaga attagcagtc tacagccaaa   20340
ccaacagcat gggtgagatg cttccagaaa tactgagatg aatttagaga taaaggcaca   20400
attggtccat atctacaggg cacttaatcc agtgcatctc cactagacaa aatttgtatt   20460
tccatgagca agagtcattt gcactgctat ctgctataac ctacggtgct gtaaaattag   20520
ctcaggcaat aaaaggggga ggtagcccca aagagtatgc cagaaaggac tcccagtaat   20580
cttcagtgtg tgtctatttc aaagtctttc atcattttc cttgtagtta cttagtgtgg   20640
aatttcagac ccctctctat gtccctcttc tcccttttca gccttggctt tctctgcatc   20700
cttccccgaa gccctgcact cagcctaaac tgactttcct gaacactctg ggagcatgtg   20760
ggctcctccc aactccacca tcttcactgc ctttctgttcc tatttccctc tgcctggcct   20820
tggcccaggg aaaccttcct atgctcagac cctctgtgcc tttgtcttca agcccaccc    20880 actattcact gccacctcca tcttggtcaa cctggaagac ttttccccatc cttaaaacat   20940 cagctcaaac ggcagatttt tttttttttt tttgtgatat cctcttgatc accctccccc   21000 agttttaag gagacagata tagaggttca atccttgggc ttcccatgac ttttcttata    21060
ttctgttact gagcaataat aaacacttct aggaactgta tcttaaacac ttttgcctct   21120
acagaatcta gcacagtgcc tagtattggt gaaatataat taacaaagtc ttctttcaac   21180
acagagattc tctccacaaa aggagtagag aaagaacagt tttattatgg aataagcagt   21240
aaaccaaaat atgcagagca ttataggcca tctactaaga ggttgcaaga acagaaagaa   21300
atctccccct tttgtatagc caagtagata caacctgtta catacatgtt atcaaggcaa   21360
acaataactg ttcctcaagt aagaggtctt gccagcaccg tttgccgtac atggttcact   21420
ctaaatttac ctggtaatta gggtaaccac ttgtgttagc taactggctc tacccagagg   21480
aaaatcaaat ttatctttaa gacaaggggt aattttgcag cactgagcaa ggctcttcag   21540
ttaggctcat accttcccac agaaactaag agatagaagc actatctccc ttaggtttgt   21600
ttacatttca aagagatgac gcccaggtcc ttgggaaaga ctagcttagc tcataaagct   21660 gacaaaagc ctatctagtt tcaaaaggat ttacacatgt tcaaagagag gagaaagtat    21720
gtaaaagttt tctaggtggg cacggtggct cacacctgta ttcccagcac tttgagaggc   21780
tgaggcgggt ggatcacctg aagtcaggaa tttgagatca gcctggccaa catggtgaaa   21840
ccttgtctct actaaaaata caaaaattag ctgggcatgg tggtgggcgc ctgtaatccc   21900
agctacttgg gaggctgagg caggagaatc acttgaaccc aggaggtgga ggtggcagtg   21960
```

```
agccaagatg gcaccattgc actccagcct gggcgatgag agtgaaactc catgtcaaaa   22020
aaaaaaaaag ttttctaaag taaatgctct gagaaaaaaa cagaaggtga ggagatctct   22080
gtccttattt ttaacaagaa taattaaatg ttttttatttt taatttctac ttagactaga   22140
atatggtaca gatgctcaaa aatattgact taattaataa ttaaacaatt aacaagtcta   22200
tctctttcct aattattaaa aaaattatga agtatttccc ttcaaaattt cacagtttac   22260
tttgacataa ataaataaat accataaagt attttgaaga ggaaagggaa gggtggggct   22320
tcaaacacaa aataatggca ggttttgtaa aggggcaatt cactaaaccc aataggattc   22380
tcctgttgct attttttttt tttttttttt tttggtggtg gttggaggga agggttgggt   22440
gtgcatttgg cctgtgtgaa aaactggtgg gtagacaatg ccatgctgtt ctagatgggc   22500
tcattgctat aggaatagat agtcactgaa tttacttgca taggggatgg ggtataaaat   22560
gtttccttat agctccttaa catggaattc agcacccctc tccccatcag ccttagctct   22620
ctctgaatcc caagggatat gtgttataaa aatagctgcc atcataaatg agaaaaccat   22680
caggacctgg taaaacttgg cttcccaaac agtcaggggt ctgggcatgg cagccgactg   22740
agaacctttc tatctagtac aaggtaaaca agatttgcca agacttgatc aactgatcca   22800
gctccctatc tccaaacaga acctcatctg aatgctcaca ggctgtgccc cagaagtgta   22860
gaagtgtcat gttccctggg caggctgctg ggcagcctct ctgttgacaa tagaccacac   22920
ttttgctgac ctaggactca tgttgctctt taagactgct tccttggcca ggcatgatgg   22980
ctcacacctg taatcctggc actttgagag gcccaggcag gaggatctct tgaggccaga   23040
tgttcaagac cagcctggtc aacatagtaa gaccccatat ctaccaaaaa tagctgggca   23100
tggtggtgca cacctatact cccagctact taggagactg aggtgggagg attgctacat   23160
cccaggagtt caaggctgta gtgagctatg atcatgccac tgcactccag cctgggcaac   23220
agagcgagat cctgtctcaa acaaacagtt tccttctgtt tgattcttgc tgaaaaattg   23280
agcatgccag agctagcaag gctcttagag gtggtctggt ccaatgcttt aatttcatac   23340
atcaagaaac tgaagcagag cagagtgacc tgcccagggt ctctcagcca ttcatgctca   23400
gaaatgtatg ggctcctgtg aaacatgtgg ctcttaaaag cactatcata tatttgaagg   23460
cagaaaatag gctaaacctt cagccttcag acttttcctc tccagagaaa atgaccccag   23520
tttcctcact atggttgctg ggagctagat tcctggggat ctggcagtgt ggaccaccta   23580
gtggtggcta gaggagcaaa taatatcccg cattccattt tccactcacc aatccctgag   23640
gggcagcctg ctgggttatg agcccacagg gggagaaccc caacgaattc agagatgcat   23700
catggaccag tttctcttaa ggggcctggg tctactattt tcagttctac ttcgagagaa   23760
gtggcctgca atatcctgca gatttcccct ccagggagaa aagcattgtg cggtgcaagg   23820
agcacaggct ttgtggaaag aggcatctgg ggttgagatc ctggctcttt tgcttccttg   23880
aacaagttaa ccaaatctct gggcctctgc tggttaattt ataccatggg gatcatcatt   23940
tctccagtgg ggttgtgaag agaatgtggt gggatcttgt gtgtggagca tgacacttag   24000
caggcatccg ggaatggcag cctcctccct ttctaaactg gggctttctg agggtgactt   24060
cagattccac aatgtcaaca gcacaatggc atcctcataa ggaaagtttg ggttgggct   24120 cctcaagcaa ttctctactc tcatttggta caaagaaaaa aattaagcct cacaattttc   24180
ttggcaccag actgaacctc aaacccagtc ttcacttttta ctaaaagcc ataaacagag   24240 accaggaggg taaaaactac cagaagatac actggattta gaaaacagta agctggatgt   24300
```

```
gaagccaaaa gagagggaga aagcaacata aaagaatgtc agattgaaga agaaatggat    24360
tctggccacc taaagaagaa gggaagtata gaaaagggaa gctgattgga aacaatgggt    24420
aatgatgagt gtccctcccc taaaaagtta aaaaataaat gagcaggcat gagaaaagga    24480
agtaggccag aggaagtaga ccaggatcag ccacggatgt gagtgggaa  ttttacaaat    24540 ttctacttgg gtgtgaaaca tgtgtacact caaagctctg tctaggttca ccgaaactct    24600
cccagctcaa ggccatttag taaaaccttg gcttaactga atagtgggta aggaggcctg    24660
aggatggccc agagaaggtt taaattctta ctggctgctg cactaagttg taaagtgcag    24720
ccttagttga tgatgccttt attagtgcaa catcccagaa tgcatgcgtc ttacaaccct    24780
tgtggatatg aaacccagct gggtagacac tgcaaagtct tctcatttga ttcttccact    24840
tggtttctag tgtccctcag ggacaaagga aagccatggt ccagtctaag atgaaaacca    24900
attagacctc tggcaggcct ttgaccaccc tgagggccac ccccaaggca cggccacact    24960
cgcatctgct gccaggaggc cctatcttag gctcagctcc caaaccttga acatcttgga    25020
ggatccacaa ataggaggta cactcagctc aggctcagtc ttccttaaaa agcgccttgc    25080
taaagctatc aagttcactg gaatacttct gcgaaggaca cagcttcagc gatgtcagat    25140
tttttatgta aatggtgcct tcacatgctc tggggcattt ggctaccaag gcggtttga    25200 actagctcca gcacacagaa tacaagtctc ttcagaacca ggcaaaaccc tatgttgccc    25260
aatgactcct gctgtttctt gagatttgca cagaagacag agctgcaatt acccacgctg    25320
atatctattt catgaccaca tatgttcaaa agccacatgt gagaggtatg gttgaaatga    25380
gaggttgtgt ttgccaagtt gtcttctgac tgtggagagc tggtgagcct cttctcatct    25440
cctggggctc catattatag agctgacgaa tctcttttct tgctccttga agtctttcat    25500
tcacttattt attaattcat ttaacacatc aggcacctac taacttctca gagttcaagg    25560
cttcctagcc tatgatcaga aaggacacct gtgtgctcat gagcacccct gggatcaggg    25620
tgactgatag ggtgctgtca tcactactag atgaaactct ttggaacaaa ggtctaggat    25680
ataatattta tccttctgca aatattcata tggcattcgc tgtgtaccag gccttctgtt    25740
gaacattggc ctgcagagct gaagaggacg tgggtcttct cttaggaact cctagtcttg    25800
ggaaaaagga atggggaagg gctgtaatgt gaagttaaaa aaaagtgctg aggccgaaca    25860
catctgggcc ctcactgcag ccctattgca cacacactgc atcacctcga caagttatt     25920 caccctctct gaattcatct atttgcccat aaaaatagag atgatccttt tatatgttgg    25980
ctaccactta ttatgtgcag catgcttgtt attgtactaa gttactcatt ttttagtttt    26040
tcatataact catatttttg ttgattttta ttttaaaatt ccaaacgaat taattaaact    26100
attttccaaa atacgtagta tgtgtacatg gtaaaaaaca tttccaaaag tttaccataa    26160
aaactgtctc ctttcccata tcctcaatcc ttcagaatcc ctctccaggg ataattacca    26220
ccaccagtgt attccttaag agatatttaa actttataca aaatacgcac acatcattct    26280
tttccacaaa tgacagcata ctatgtacat ggtacctcac ctagcttttt tcacttacca    26340
gtatatctta gagattgttg catgacagaa tatacagatc tgcctgtttt tgttgttttt    26400
cccaagtttc caagagctag aaactgtttg gtttttaagc agctgcttgg tattccatta    26460
attggactta tcgtgctttg atctgtccct agtgatggac attggggttg tttcccttca    26520
tttatatttg aagcttgttg cagtgacagt gtacacactt gcttgagcat gtgtgtgtct    26580
acgataaatc ccaataagca atttaaagta atttaattct tatgctctca acaaacctaa    26640
gaggttattt ttttagagga ggaagctaag gctgttgttt tgatgccttt ttaccactgg    26700
```

```
acttgggact caactgtttg atagtcatcg agtccttgac tcttctcccc tgccaggatt   26760
tggcccctaa gcccagggcc cgagtctcct ccatcttcaa gggagagtgg gaacagcaca   26820
ggccttggcc tcagtcctgc tcccctgct tctagctgtg ggatgggcca ggtgcttcac    26880
ccagctgtgc ctcctgtgag gcacagtgtg tgcaaaatgg aaatgtgaac atgaagatca   26940
aaaatgtccc tcaatgacca gtgctgttcc tcagagtcac gtgggaactc atagaaagcg   27000
atattggtac tgctctttcc tctgtagcat ggtccagatg gctcatagca gggaccatga   27060
tatgctgggt gagcacccac tgcatgcacc cactgtgcca gcactgagag actcctgtgg   27120
gagccacagc aattctaggg tcttcactgg ggactctgag acagcaggga gctaggatga   27180
gggctgcaga gtgttcgtct gccctcactg agcagacccc ctggatggca gggagcagtc   27240
ccaagccaga tggatgccca taaccagcca tttggctctc aatacataat atcaccacgt   27300
atcaggcaaa accatcctgc ccagagcatt atctgaattt gcatcccatc tgcagaagat   27360
acattcaccc acttcttcca ttctgtctta atcaaagtct ttatgtgaat tttccccatt   27420
gagaagacaa gccccttcct ggcttagact gtacctgact gatcttttca tgagctcctt   27480
gccaagccag accacccca gcttatatgg agacttggtg caaattagag atgcccctgt    27540
gcacgtggca gccctgagcc caagcaccca gtaaggcaaa gggcctgatt tgggacccct   27600
ctgccactcc accaggcaat cagttgctta tttctaactt tcccttcctt ctccacattt   27660
gtcccattcc ttcctctcat catgaatatc cccagaggca ttcagcagtg cagtgaatta   27720
aatatagaac tttttttttt cagaattgca gaacggatta gatcaatatt aatccaaaca   27780
gagcaatgag cctgacagtt tagtaaaagc tcaataaagg gtggcttacc tcccccaaaa   27840
taatctgaaa agaaagcatg tcttatttca gggggaaaaa aaaataaagt gacctttaaa   27900
gaccaaattc ccaggatacc cagggtggag gtggaacatg ggagtccaca ggcagcctgg   27960
atgtttccaa agatccaaag ggcttttgct tcctcacata atgcaggaaa caaattgaac   28020
atgtattaag tgcttgctgt atgtgacaca ctgtgccagg tgctcccctt aaaacagttc   28080
tgtgggcagg catgagaatg aatcccgatc ttacagacaa ggaatgttag gctcagaggt   28140
ttcaagctca cccatcactc agccagagag gacagatgca ggattcaatc tcgggagtgc   28200
ccgagtccac agaagttcct gtgctgaagg accgaccaca ggcacataaa gagatgcgag   28260 acaatttta ctgatttggg ccacctctcg aggtcggctt tgccagctct tctcactggg    28320
ggaaggggag ggagaaagta gctagctcca gggtccctaa catagaacca ccaaggactt   28380
gactattttt actcatacag cagcttgtct gggaagatca tgctctgtga caagctgcag   28440
gcactaagta gcaatttctg tttcccacat attagcttga gtcatataaa actgacatgg   28500
atgtggctca aaaatagctg tatgtcagcc attttatacc atttgactta aatgttatta   28560
attaacgtca cagccagaga ttattctctg agaaagggc attgtagcct gaagcagaga    28620
aagcatacac gttccctggg gttgagaact catcacagcc tgagacagct taggttgtaa   28680
agccccggcc cacttatccc aggagagtct gggtgagatg caggccccaa agcagaggct   28740
gggaagcgag aagtgacaca ccctggctgg gtgggccctc atcttggtga cacaccct    28800 gggtaaaacc atcatggaaa gggtgtagtg gggcgtggaa actccctcgg ttaaagcgtg   28860
agctttgctg taagttgtgg taaggaggga ggcagtgaca accaggaggc ctgttttgag   28920
ggtttctgag ggaccatct gtggtatcac gaggagacgc ccagaggagc cgtgtgaaag    28980
ggctgcctcc cagccggctc tggagtgaat gagcagcaag tcctggctgc gaaaagaagg   29040
```

```
ggagtgcagc ctgcagaagt gtcttctttt ttcaattcct gctcagaagg aaacaggaga   29100
taagaatagt ggggaagtcc aaaccaaagt gaactatagg gctggtaatc gtaggggaa    29160 ttagtcaccc ggagactagc ccagcagact aacggagccc catcctccat cttgaatcag   29220
tcagcccctc tatgactgca gagtcctgaa tgatggcaac accttctctt cacttagcgt   29280
tgtaggatga ccaacagtcc tgatttgcct gggactgagg ggttcccaat agatgggact   29340
ttcagggcta aaaccaggaa agtcctgggc agcccaaaac aaggtagtca ctctagagtg   29400
tatgactctg tctgatacct gctaagaaag agaaggactt gttgattata aggagaagag   29460
gaggtgaaat ggttctcaaa aaacaaagat gagggcttcc gggtgctgtt ctgcccaagg   29520
ctctgggtct gaggcttctc tctccaggcc tagcttcatg gaaaagtaag gggccagagg   29580
gtggaaaagg tggaaacaaa ggaagaggat ggagaattgc tttggggaag tttggactgg   29640
aagtgtgaat tacagctgca cccccaattc accccatctc accccctcc cctcctgct    29700 catggttctc cctttctcat ccacacattg gtcaaactag ctagcttttg gagagatttt   29760
gggcagtaaa agtaaaacag atctgtctca agcttcaaaa agcctagagc tggctgggcg   29820
ctgtggctca cgcctgtaat cctagcattt gggaggctg aggcggaagg ataatctgag    29880
gtcaggagtt tgagaccagc ctggctaaca tgatgaaacc ccatctctac taaaaataca   29940
aaaattagcc aggcgtggta gtgcacgcct ataatcccag ctatttggga ggctgaggca   30000
ggagaatcgc ttgaacccca ggggacagag gttgcagtga gctgagatcg caccactgca   30060
ctccagcctg ggtgacacag cgagactcca tttaaaaaaa aaaaatgcc tagagccaaa    30120 tgctcacaga gccatttact gcatggcttt ggcaagtca aaggagtccg cctctcctgt    30180
cagaagagtc tgttgcagtc ttcatcacaa gactgttgtg gggattaaac aagatggcaa   30240
gtgggaagtt gggaaatgta gtgtgcaccc aaccaatatt tgtttcttcc tgcctgccta   30300
catatgaggc cacacagaat tccaactttg tttctctgat aactaacaca gttacttgtt   30360
tttcttcctg atccaggcct tcaccatgga tcagttccct gaatcagtga cagaaaactt   30420
tgagtacgat gatttggctg aggcctgtta tattggggac atcgtggtct ttgggactgt   30480
gttcctgtcc atattctact ccgtcatctt tgccattggc ctggtgggaa atttgttggt   30540
agtgtttgcc ctcaccaaca gcaagaagcc caagagtgtc accgacattt acctcctgaa   30600
cctggccttg tctgatctgc tgtttgtagc cactttgccc ttctggactc actatttgat   30660
aaatgaaaag ggcctccaca atgccatgtg caaattcact accgccttct tcttcatcgg   30720
cttttttgga agcatattct tcatcaccgt catcagcatt gataggtacc tggccatcgt   30780
cctggccgcc aactccatga acaaccggac cgtgcagcat ggcgtcacca tcagcctagg   30840
cgtctgggca gcagccattt tggtggcagc accccagttc atgttcacaa agcagaaaga   30900
aaatgaatgc cttggtgact accccgaggt cctccaggaa atctggcccg tgctccgcaa   30960
tgtggaaaca aatttcttg gcttcctact ccccctgctc attatgagtt attgctactt    31020
cagaatcatc cagacgctgt tttcctgcaa gaaccacaag aaagccaaag ccattaaact   31080
gatccttctg gtggtcatcg tgttttcct cttctggaca ccctacaacg ttatgatttt    31140
cctggagacg cttaagctct atgacttctt tcccagttgt gacatgagga aggatctgag   31200
gctggccctc agtgtgactg agacggttgc atttagccat atgttgcctga atcctctcat   31260 ctatgcattt gctggggaga agttcagaag ataccttac cacctgtatg gaaaatgcct    31320
ggctgtcctg tgtgggcgct cagtccacgt tgatttctcc tcatctgaat cacaaaggag   31380
caggcatgga agtgttctga gcagcaattt tacttaccac acgagtgatg gagatgcatt   31440
```

```
gctccttctc tgaagggaat cccaaagcct tgtgtctaca gagaacctgg agttcctgaa    31500
cctgatgctg actagtgagg aaagattttt gttgttattt cttacaggca caaaatgatg    31560
gacccaatgc acacaaaaca accctagagt gttgttgaga attgtgctca aaatttgaag    31620
aatgaacaaa ttgaactctt tgaatgacaa agagtagaca tttctcttac tgcaaatgtc    31680
atcagaactt tttggtttgc agatgacaaa aattcaactc agactagttt agttaaatga    31740
gggtggtgaa tattgttcat attgtggcac aagcaaaagg gtgtctgagc cctcaaagtg    31800
aggggaaacc agggcctgag ccaagctaga attccctctc tctgactctc aaatctttta    31860
gtcattatag atcccccaga ctttacatga cacagcttta tcaccagaga gggactgaca    31920
cccatgtttc tctggcccca agggcaaaat cccagggaa gtgctctgat aggccaagtt     31980
tgtatcaggt gcccatccct ggaaggtgct gttatccatg gggaagggat atataagatg    32040
gaagcttcca gtccaatctc atggagaagc agaaatacat atttccaaga agttggatgg    32100
gtgggtacta ttctgattac acaaaacaaa tgccacacat cacccttacc atgtgcctga    32160
tccagcctct ccctgatta caccagcctc gtcttcatta agccctcttc catcatgtcc     32220
ccaaacctgc aagggctccc cactgcctac tgcatcgagt caaaactcaa atgcttggct    32280
tctcatacgt ccaccatggg gtcctaccaa tagattcccc attgcctcct ccttcccaaa    32340
ggactccacc catcctatca gcctgtctct tccatatgac ctcatgcatc tccacctgct    32400
cccaggccag taagggaaat agaaaaaccc tgcccccaaa taagaaggga tggattccaa    32460
ccccaactcc agtagcttgg gacaaatcaa gcttcagttt cctggtctgt agaagaggga    32520
taaggtacct ttcacataga gatcatcctt tccagcatga ggaactagcc accaactctt    32580
gcaggtctca acccttttgt ctgcctctta gacttctgct ttccacacct ggcactgctg    32640
tgctgtgccc aagttgtggt gctgacaaag cttggaagag cctgcaggtg ctgctgcgtg    32700
gcatagccca gacacagaag aggctggttc ttacgatggc acccagtgag cactcccaag    32760
tctacagagt gatagccttc cgtaacccaa ctctcctgga ctgccttgaa tatcccctcc    32820
cagtcacctt gtggcaagcc cctgcccatc tgggaaaata ccccatcatt catgctactg    32880
ccaacctggg gagccagggc tatgggagca gcttttttttt ccccctaga aacgtttgga    32940 acaatctaaa agtttaaagc tcgaaaacaa ttgtaataat gctaaagaaa aagtcatcca    33000
atctaaccac atcaatattg tcattcctgt attcacccgt ccagaccttg ttcacactct    33060
cacatgttta gagttgcaat cgtaatgtac agatggtttt ataatctgat ttgttttcct    33120
cttaacgtta gaccacaaat agtgctcgct ttctatgtag tttggtaatt atcattttag    33180
aagactctac cagactgtgt attcattgaa gtcagatgtg gtaactgtta aattgctgtg    33240
tatctgatag ctctttggca gtctatatgt ttgtataatg aatgagagaa taagtcatgt    33300
tccttcaaga tcatgtaccc caatttactt gccattactc aattgataaa catttaactt    33360
gtttccaatg tttagcaaat acatatttta tagaacttcc atctgtgtaa tcttctttct    33420
cctattcaat tatttcctgt ggttaaattc attgccatgg ggaaaactga gtcaaagggc    33480
atgggaacac attatctttg catacacaca tatgaaagtc atatattaca caacctttac    33540
tgagtcgtat tatatacaaa acatgaacgc agatccagct ctattccaaa ggcaatgaga    33600
ccaagcctct tccctcaata atttaaatgc agaagagaag tgaaggaata atcacgcttt    33660
gcattaggtg gtagcagagg agtactacgt gacttctgac ctgcgtcttt aagggacagg    33720
ggttctccag gtaaagaaag aggtggcatt ccaggctgag gaaacagcat gtataaagga    33780
```

```
agtgtgtgag agccacaatg tgagaaaact ctgtgcgaat attaaaaggc gttagaagcg    33840
gagtgggtgg taggaacttt ctgagctgag ctgttagctg tgggctgagc taaaacaacc    33900
aatggagggg gtgctggttc tcctcagggt gtttacgggg tttcttcgtt attacctgat    33960
cctcattcca actgttgaac cataagactt ttaattaaag tttaacctat tcctggactt    34020
ctaagaagga ggaaataatt attttggctt gagaaataaa agaagagaaa taaacacttt    34080
catttctaga agaaaattaa atttgtaaca ttaggaacct atatttattc attcattttg    34140
ctgaatagga cagaataggg agaaaataag gaagctcatt gaaaaatcca aaatagcaag    34200
gatgttggtg tctaaataaa ggaaggcatt tttggaaagg acagctggcc ctcagagcac    34260
acctgaatca gacccactcc tgcttctgag gtctgggctt cccaagagca gagggatctg    34320
cctgtgatga atcccgacat attaactctc tgcttcggca ggttgcttaa catctctgag    34380
gctcaatctc ctcatcagaa aaataaagat aaaagtagtt cccacctggt aggggttggag    34440 cagaggattc agtaagatta cccctgcaaa gatcacacag aggattcagt aagattaccc    34500
ctgcaaagat caca                                                      34514

<210> SEQ ID NO 2
<211> LENGTH: 30001
<212> TYPE: DNA
<213> ORGANISM: Homo sapiens

<400> SEQUENCE: 2
tcaagtgatt ctcctacctc agcctcctga gtagctggga ttatgggcgc ccaccaccac      60
acctggctaa ttttttgtact tttagtagag acgtggtttc gccatgttgg ccaggctggt     120
ctcgaactcc tgacttctgg ttgatctgcc caccgcaacc tcccaaagtg cagggattac     180
aggcataaac caccacgccc ggttttttt ttttttttt gagatggagt tttgctcttg     240
ttgcccagac tggagtgcag ttcctcaatc tcggctcact gcaacctctg cctcccagat     300
tcaagcaatt cttctgcctc agcctctgga gtagctggga ttacaggcac ctgccaccat     360
tcccggctaa ttttttgtat ttttagtaga cagggtttt caccatgttg gccaggctga     420
tcttgaactc ctgacttcag gtgatccacc cgcctcagcc tcccagagtg ctgggattac     480
aggcatgagc caccacaccc agctttagct ggcattttc tacaaagagg atcttcaact     540
agaaatgaac cacagtttct ccttaaaaag gcaggataaa tgcttaattc tctaaggaaa     600
gggttttgtt ttttcttttt aaacaagaga ttctagaatg tgtttgtatg ctaagaggat     660
aactctgtgg aaggaaaagc tggatggtac gagagatgga gttacagagg tgtaacatcc     720
ccagaaggtg agaggattta gaattcaggt ggggaaggag gagaagggt aggatgttgg     780 aagacaaaag aaaagtgtg agctgctcat ctgggcagag tgatagggcc tgcttagtga     840
gaaatgcacc agaggattgc tgggcctggt tagtgtccta ttgaggctgg gagttgcgac     900
cctgtctgca tagcaagcag ttttctcctc cacatttaga aggtaaggga ggtcgggcgc     960
agtggctcac gcctataatc ccaacacttt gggaggccga ggcaggtgga tcacctaagg    1020
ttgggacttc gagaccagcc tgaccaacat ggagaaaccc tgtctctact aaaaatacaa    1080
aattactgca ctccagcctg gcgacagag tgagactcca tctcaaaaaa aaaaaaata    1140 caaaattagg caggcgtggt ggcgcatgcc tgtaatccca gctactcggg aggctgaggc    1200
aggagaatcg cttgaatctg ggaggaggag attgcggtga gctgagatcg tgccattgca    1260
ctccagccta ggcaacaaga gcgaaactct gtctcaaaaa aaaaaaaaaa aaaaaagaa    1320 ggtaatggtt agattcctgc aggcctgggt tttccaggca ggtacactgg agggagaggg    1380
```

```
agggagaggg aggccggaca gtgccaggtc tttgcaacga atgaccataa ggactgacag    1440
cagaatctag gctggttgaa agcaggagtg agaagaggag gagagtgatg gctagctggg    1500
aaatggatga gagaggtctc attgggcttg ctgggctttg attttttgatt ttggtatcag    1560 ttttttagaat tgttttatttt atttatttag agacaggggtc ttgctctgtc acccagccta   1620
gagtgcagtg gtacaaccat ggctcactgc agcctcgaac tcctgggctg cccaggctgg    1680
tctcgaactc ctggcttcaa gtgatcctcc tgtctcagcc tcccaaagtt ctgggattac    1740
aggtgtgagc caccatacct gacttagaat tgttttcaag gagcttgtga atacatgggc    1800
tgaaaggata ggaaactgtg gtcagagagt tgaggtttaa ttgaatgaat gaatgaatga    1860
atgaatgata gtgaacactt atgtggtatt tactatgtgc caaacactcc tctaacagct    1920
cactgatttc tctcaagact tctgtgaggt gaggtctact aaatttccat tttacatatg    1980
aggaaactga ggtacagaaa ggtgaaataa cttgggcagg gcgcggtggc ccacacctat    2040
aatcccagca ctttgggagg ccaaggcagg tggatcagtt gaggtcagga gtttgagacc    2100
agcctggcca acagagcgaa accctgtctc tactaaaaat acaaaaatta gctgggtgtg    2160
gtggctcacg cctgtaatcc cagacactca agaggctgag gcaggagaat cgcttgaacc    2220
tgggagttac agtgagccaa gatcacatca ctgcactcca gcctgggaga cagagcaaga    2280
ctctgtctaa aaaaaaaaaa aaaaaaaaaa ggtgaaataa cttgtccaag gtcagagttg    2340
gtctgcaaac caggcagcct gggcccagag tctgtgttcc taatcaaggt tattctgaaa    2400
ggatgaatga gggcatagaa tccactttgc tcgtcctaag aagtgccagc tgtctcctga    2460
cctcagattg ggtcagagcc ctaatctggt ttagagaggt ccagagacaa aaacaatga    2520 acacagaaat atataattcc agattgtgat agccatagag gagacaaact ggatgctgag    2580
accgagaata aggagacctt cttagatgtg gcagtcaggg gaggcttccc tgaggagacg    2640
gcacttcaat tgaagaataa aaaggaagca gtactgtgaa gagcaagaag aagagcatcc    2700
taggaagagg gaacaccatg taaaaagact gtgagacaaa aattcagtgt attctaggaa    2760
ctgaaaaaga tccaaatgtg ggtaaaggga aagatggcta aagctgggac tggagaggag    2820
gcaggggcca agcacacagg gcctcagagg acaagacaaa gctgctggat tttattattc    2880
tttattatta tggtatcgta tgtattgtat ttttattttt ccaagcaaaa tgaaaggtaa    2940
ggcactggga gattttaagc aagggactaa tgtggcccaa cacatatttt aaaaagtaga    3000
agcaattttt ttttttgaga cggagtcttg ctttgtcgcc caggctgaag tccagtgccg    3060
tgatctccgc tcactgcaac ctccgcctcc tgggttcaaa cgattctcct gcctcagcct    3120
cctgagtagc tgggattaca ggcaccggca ccacacccag ctaatttttgg tatttttagt    3180 agaggcgggg ctttcaccaaa ttggccaggc tggtctcgat ctcctgacct caagtgattc    3240
gcccgcctca gcctcccaaa acaatgggat tacaggcgtc agccaccgag cccggcctga    3300
gaagcaatgt tgtcattttg ttcttccatt catttgctta ttcagtcatc aattcttgaa    3360
tttcttcatt cattctttct taccttccat tatttagttt ttcactgggc tttcctttgt    3420
tcatctgtta attcctttgt cctttggttg attcacgtgt tcctatacac agaaagcctg    3480
ctactgtgtg ctgggccttg tgtgggtact ggaggcatct acaagagcca gaccctgcc    3540 cttgaggaaa acatatccca cacacccatc ccccaggaac cagtggtgcc ccaggcagaa    3600
gatgctgagg ttctgctggg ggtgtggagt gggtagaggc agcaatcagg gaaggcctct    3660
agagcagatg cttgtgagtc agaccttgaa ggatgacaga gcgagcatga tagattgggg    3720
```

```
ggatccccca agagcaggga ccagtctctc atctctgtgt tccctaaggc tggcacctaa    3780
gacacaatta taaacgtttg cttgtttgct aattgaacat gtgggccgat ggccaggcag    3840
ggagcatttg atgcggagg  tgatgctgcc cggctagggt gaagccactc ttccagagac    3900
cctgcactgc cactggctcc tctgtcttcc cctcatccc  cctcccatt  tcctaagaga    3960 aaagcattct tatctccatc ccaccactct gttaccccag gcacattggg ccacacttga    4020
gcatgtgtac gcatgcacac acacatcccc acatgcccct gcccatacaa agaaacacac    4080
ttgcctgcac accatggcct agttgttgat tccaaaagca aagtcatcat gtcattgctt    4140
tctctctctc tctctctctc acacacacac acacacacac acttctgt   gtttacgcac    4200 actctccctg cctctcacca catcccaaca gacacatcct tctccaccaa acagccctcc    4260
ccaccacacc tcttcctctc ctggacagga gggatattcc gggttcttgc tttaaggctg    4320
aagtaacagt ggtgggagtg gggactgaac cccagattga ggaggggtca gggatcccta    4380
tcagacagag agactggaac tgatagagga tgctaccgtt tctcttttg  ttttaaaaa    4440 tcttttcca  catgttctaa gatactcagt ttttcttcct tttttttttt tttttttttt    4500
ttcttgagac ggagtctcgc tctgtcgccc aggctggagt gcagtggcgc catctcggct    4560
cactgcaagc tccgcctccc gggttcacac cattctcctg cctcagcctc ctgagtagct    4620
gagactacag gcgcccgcca ccacgcccgg ctaattttt  gatttttagt agagatgggc    4680
tttcactgtg ttagccagga cggtcttgat ctcctaacat cgtgatccac ccgcctcggc    4740
ctcccaaagt gctgggatta caggcgtgag ccgctgcacc cggccttttc tttctttttt    4800
ttaaaaaaag tcattttctg caacaaaacc cacattcttt ttttgtgttt ttttttttta    4860
aggcagggtc ttgctctgtc acccaaggta gagtgcagta gctcaatcac agctcactgc    4920
agcctcgacc tgcctgactc gagggatcct tccacctctg cctctgcagt agctgggacc    4980
acaggtgcac accaccacac cgagctaact taagaaaaat ttttttggt  agagatggtg    5040 tctccctatg ctgcctaggc tggtctgaa  ttcctgggct caagcaatcc tcccacccaa    5100
cctcccaaag tgctgggatt acaggctgag ccactgcccc cagccagtta tcagtttttt    5160
ctaaaacttg ggtgcctggg ggaggctgac acccttccca ctcctctgaa aggcagtttc    5220
ctaagggaag ggtcttctgc tgctcaccac ccttaacagc cctgtgtccc cagtgctcag    5280
cccctgagga agggaaggcg tgctgacagg gtccatgtga tccatgtcca gtggctctgg    5340
tgacagcagt ctgaagtcaa ctggctgtga gaactcgagt aaggccagtc ccgatctggt    5400
cctcagtgat ggagaaaagc ccctcttaac ctccaattca atgatcctaa aagagcaggt    5460
gcttcggggg tgctgaaact gcgcttttgg agggggcttt tgggaaggcc gggctgggga    5520
ctcaggtctg gagggtgaca gagccgacct cccgtaaacc agggaggagg aaggtggggg    5580
cgggtgggcc taggatctgg gggcgcctcc tcgctgcggg gagctggctt ggggctaggg    5640
cgtgactgtc tccctgccac catcaccgcc cgccggccgt gactgcaata agagaagtcc    5700
gaggcggctt cctcctccct gcccagcagg ggcggcggtc agaggcgggc agcacccag    5760 ttctccccgc acgccggcac tcgcggctgc tggagccccg ctggctcac  cccggggccg    5820 ggcagaattg ggctccaggt aagcgacagc gtcgggtggg gactgggcag gtcaagcagt    5880
gccctccccc tcgaggctct ggagagagga ctgggggtac acgggaagag aagcctgaac    5940 ctggggtcg  gggacacat  gagcaaggtg acagccaaag ggaccccagc ccgaaaaggc    6000
ctaaggagga aaacgggcga cctgaaaagc aaggctgata aacctggagg agagggcgga    6060
ggggagcacg ggggaagccg accaaaggga cccccaaaaa ggtctagtgg gtaaaatgga    6120
```

```
ggggactgat aagagtttag aagggggct gaggtggggg agaaggatta agggggaatcc    6180
ccaggacggt ctgggggaga aactgaaggg atcgtgagag tgggactttg gggagaagcc    6240
gacgggtctg atgggtccag gagaggggaa atgggtgggg gtgctggagg aacaggaga    6300
gggagctggc gggaagggggg ttgaggagaa cgacttctgg aggacggaga acctggggtg    6360
caattgcggg tccaggaagt tcccctcttc cgagccggcc gaagtcgggg tgaagcccac    6420
agcccgcagg gtaacgttag cggcgcgac cgcggcccg cgaccctctc ggcccgccct    6480
tgcggtaggt tccgggctgc agggggactcc tgccgggcgc gcgaggcgtg ggtccccgct    6540
tcctggggaa gtccccgccc tcggcaggga caggcctctc cgggcgcccc ctccgcgccc    6600
gcggcggtct cggcccgcgc tccccgctgg atccgggaat tgctgccgcc ccgacggaaa    6660
tcctgccttt gaccgcgagt gcccgcaggg gctgcctcca aggcaacgag agggcgggcc    6720
gcgctgggcc gccgcggggc tccgggtggg cgcagccccc tttgctctcc gccttcgccc    6780
cctttttggaa tcctcggtct ggtgggtggg ggtgggcttt cccgaccgag gtaggaggcg    6840
atgccgctgt gttcagggat cctggggtgg aggatctgct gtttgagaga cctgggttct    6900
tagcaagact gggccccttaa ttgctgtgtg actgtgggca agttacaggg cttctctggg    6960
cctcactttc ctcatctgaa ctatggtgag aaatgatcct tgtgtccact cttcccccac    7020
gagaatcagg tgcagaaagc agttttttgct gagtgtcctg aagggttaag ggctatccct    7080
gactcagcga gcctccccctt caccttctca aaaacatgca gaggaggcca gcctgggcag    7140
cacagggaga ccccccgtcct gtctctacaa aaaaatatag ttagccagaa ggctggaagt    7200
ggtggcacct gctgtagtcc cagctactcc agaggctgag gccggaggat cgctggagcc    7260
cacgagttca aggctgcagt gagagctcct ggatgagaga gtgagatttt tgtctgtaaac    7320
aacaacaaca acaaaaagca tggaggggga ccagactgcc cggctctcac tgacagggcc    7380
tccagggacc agcacacagt tggcgtctaa atagtttatg gctctgatga gagcccatac    7440
tggggaggtc agcagagtta aaatctgtct cacaccctct ctggtgctgc atccagttgg    7500
ccgcccctcg ggtgtgtact ctcagggggcc ctgatgtcct tggcatcctt ccgactgtgg    7560
tgatgatggg agagcaggac cctgttccca cttcacagat gggaagatgg aggtttggga    7620
gttggcaacc tgcagggcca acagtaggga ccagaattcc aggacatctc gtctctgatg    7680
tagcctgagc tgaggcctga atccttacct catccctacc aagtttcatg taccctccgg    7740
ggaggagggt gtgggtttta ggggcttcat gactacttcc tgttccagtg agtaggtgct    7800
ctcacaccct cctccagtga gggtgtgagt gttttgtatgt tttgggctct gagtgaatga    7860
gcatgaaccc ttgagcatat gagtggatgt ttgggtgatc tctgcagcca cctggggctg    7920
atgtggcaaa ggaagtggcc agacctcagg aggctgggta gggaacccca gagctgggga    7980
agtaggggcc agggctcttc ccacgcagag cagactgggc tgacctaagg tgggaaaagg    8040
caggatgtcc ccctcaccgc cccactcccc tgagggacca gggaggggc ttcctgtctg    8100
gccacactgt gaaatctaga ctcccatccc ttggctgccc ctggacccccc gcccccgcc    8160
gccatggctt ccatctcctg aaaatcctga gtcccaggcc agatggcatc taaagagctg    8220
tgttttagag gctggtgggt ggttttcagc aacaggtgga aaaccacttt tacccacaag    8280
aagtggaaaa aactgctaat ggcctcggga ccacatggag ggtaaaggcc accccgatc    8340
ctgcacacac ctgcctcac cacgtggtg gtggagtcag acagggttgg gtgggtatgt    8400
cttcttcagg aggcagtttc gaggcctcaa gaaaggatgg tgtgagatga aaggggtta    8460
```

-continued

```
atgaaggcag ggcacggtgg ctcacgcctg taatcccagc actttaggag gccgaggtgg    8520
gtggatcacc tgaggtcaga agttcaagaa cagcctggcc aacatgacta aaccccatct    8580
ctactaaaaa tacaaaaatt tagctgggca tggtggcaga cgcctgtaat cccagctact    8640
caggaggctg aggcaggaga attgcttgaa cccgggaggc agaggttgca gtgagccgag    8700
atcgaaccat cgcattccag ccttggcgac agaatgagac actgtttcaa aaaaaaaaa    8760 aagaagaaga agaagaagaa gaacaaagaa agaaagaaag ggagttaatg agcagtgggg    8820
gcctcagcaa aggcactggc attcagccag gtggagggtc tcggtgagag gactgagggt    8880
gagggatgga agcccgcccg gtctgaggga tagggcctag tgagagatgc ggcacagtgg    8940
gatgggagtc acctgcagac ctcagccttg ctccctgacc ctccagcccct ggcctgcccc    9000 cggccagccc agagcctgga ggagaagccg gaactcttgc aggatggtgg tttcctgccc    9060
ctgcccaaag tcccggttcc cttttgatga atcccccag gcggctgggc cagctcagcc    9120
ctctcacctc accctgggaa cttctctttc ttctcagccc tgcccagttc tgtaccctct    9180
ggtcccacac cgtcactgcc acggaggacc ttcctcaagg gaaaggaggg aagtgaaagt    9240
tcactgggca cttactgtat gtctgatgct ttcagtgatg tgaccccatt tgatgctgag    9300
aagcaacccc aggaggtgga catttgtatt cttattttat aggcaaagat gctgccgctc    9360
agggagatga actgacttgc ccaatgcctt aagctagttg tcaggcaggc tagaatttga    9420
gcctaaatct gcctctagat cccacagata cttggtgagg gttgcgggg caggacatcc    9480 tgtgtctaca tcaaagaact ggcatagctt tgggaagtgt gggcctcgaa aaaggatggg    9540
tggacctggg gttcctatgt ccagcagtag gggtgagtgg gaggcagggt ccctccctgc    9600
tgggtgacca gctgccatat gacaggggtg gtgtgttcga ccggaagtat gacattcact    9660
agttaggaac agcatgatct cctgctcagg ctttggagaa cacagcagtg ggggagggaa    9720
cagaactctg gacttgaatt aatagtcctg actttgaatc ccttgtctgg ctgtgtgatc    9780
ctgggaaagt aacttccccc tatgcaaaag agaaggtgga gtggtaaatg gtccctgggg    9840
gccattctgg ttttggttat tggtcacact tggccactgc acatcgggca agagccacat    9900
gtcatgaagc cctcacaaca actactcaga aggtgcagat gcaacaacta aggctcagag    9960
gcttatgtca aagatccaag gtcatagagc tactgaagaa tggagctggg gagggccaca    10020
gggcagatgt tgaagtgagg agcactgcgg tccagggttg gacctcagtt tgatacttgt    10080
aacctgattt tgaccctgat ggggatctcg gaggcgactc ctgtaaacca gatgttcaag    10140
agacatattt ataaacagaa ccaagtgccc agaatgatgc tgtggctact ctctgagctg    10200
cccccttcct ggtattagca ggcagcgaag ttcagtgctg agaaaagaga gacctggctt    10260
cttcagattc agcgactgcc tgagaaaatc tgggcagata tggctctctc tctctctctc    10320
ctgcgcccct ccctccccc acctgcgccc tgcctgctgt atcaaggatt tagagcatga    10380
ggcacagggc tgagaacact aggtgctcct taagagacac acgttattgc aggggtgtcc    10440
aatcttttgg cttccctggg ccgcattgga agaagaaaaa ttgtcttgag ccacacataa    10500
aatacactaa cactaatgat agctgatgag ctttaaaaaa ttgcaaaaaa ggccgggtgc    10560
agtggctcat gcctgtaatc ccagcacttt gggaggccga gcgggcaga tcacgaggtc    10620 aggagatcga gaccatccgg gctaacacgg tgaaacccg tctctactca aaatacaaaa    10680
aattagccag gcgtgttggc agcgcgcctg tagtcccagc tactcaggag gctgaggcag    10740
aagaatcact tgaacccagg aggcggaggt tgcagtgagc caagattgtg ccactttact    10800
ccagcctggg caacagagtg agaccccgtc tcaaaaaaaa tcacaaaaaa aatctcataa    10860
```

```
tgttttcaga aagtttacta atatgtgttg ggccacattc aaagctgtcc tgggctgcat   10920
atggcccatg gaccatggga tggacaagct tgcattattg cttctactag gattacagaa   10980
tggactagtg gttacagtgg tttttggcaa caagttgatc agcattgcat tttagcatcc   11040
tttactcaca atgtaatctt gggcaagtta cttaacatct ctgtgcctca gtttcttcat   11100
ctgtaaaata agggtagtca taaacccacc tcataggttc accaaataag accatgactg   11160
ggagttactt ggcaagatgc tagtcactgt gtaactgttt aataaattag ctcattttta   11220
ctgccacctg gatttctagg aagtcaaatt actctccaaa gaattggtgg cacatagaga   11280
tcagagcaag aggaggatga agagtcctag ggctattttc atgcagatgt ctgagcagag   11340
tgaacccaat ctgctctccc tccgtctttt tccctccttg tctctttagc tctctctctc   11400
tctttctctt catctctgcc tctctctgtt tctatctctt tctgtctctt gattactctt   11460
tctccttaat tctcatttct gcctctgtct ctttgtctct gtttctttct ggcagtgtgt   11520
gctggagcca gctacttact ggctcagggg agttcattct gtgtgtctct tccaccccag   11580
cttttcaggaa gtcactttgg tagctttaaa tcagccattg tgggaatatt tacaccatgg   11640
aaatcagaaa atgtgacaaa tcagggcttt ttcttttctt ttcttttctt tttttgagag   11700
tcagtttacc agcataccac gctgtgtttc tctgtctctg tctcttcctt ctatctctct   11760
gtctttctgt ctctctggct cttttctctt atctccctgt atctctcaaa ctctgcctct   11820
ctctctcttt ctttctgcct ctcctttttc tgtctttccc catctctttc tttcctctga   11880
caaaacagca tgaacatggc tacatgcagt gtggcccctc cctgccttgg gccatgcaga   11940
tgtcataccc tgtgccctac atccctgac gcctcagcat actggtcccc agagagccag   12000
gcctggccag ggctttggtc tgcatcaagt ttggaagtga taagacccaa gagctgccta   12060
cctctgcctg ctgacgacac ggtcagtcct gccagggctc ttcctgagcc cacagagctt   12120
ccttctcaga tgctgatagt ctctcccttc cagccatact gggcatgcag aattcaggga   12180
tcccctccat ctgatataga tatgttgtgg caatatatac gtgggtatta ttggaagtgg   12240
caatattgta tctgtgtgtg aacatgagag attgtataag tctatgttct cctatagagg   12300
agagctctat gtgggtccat gtcaccgag agggctgtgt atatctgtgt gtgtgtgtgt   12360
gtgtgtgtgt gtgtgtgtgt gtgtgtatcc ctacatgggg ggtgggggga cagtgtgggg   12420
gcatccgcat ttgtgcatgc tagcaggaat ggctgcatct gtctgtatct gtgataggca   12480
atggagagaa atgcttgaaa gctcagattc tggagccaaa caccaggata catcatgtct   12540
gtggcccttct ttttgagac agagtttcac tatgctgccc aggctggagt acagtggcat   12600
gatcatagct cactgcagcc tctatctcct ggtcttgagt ggtcctcctg cctcagcctc   12660
tcgaggcacg tgccaccatg ccaagctaat ttttggagtt tttttggttt ttttttgttt   12720
tttttttttt tgagacagag cttcactgtc actcaggctg gagtgcagtg acaggcgtaa   12780
gccaccgtgc ctgccaatt tttgtatttt ttgtagagat gggatttgcc atattgccca   12840
ggttggtctc gaattcctgg acccaagcaa tcctcttgcc ttggcttccc aaagttctgg   12900
gattacagat atgagccact gtgactggcc aaccctgggc aggtttccaa acctctctgt   12960
gcttcagttg cctcatcagt aataataata cttaggccag gtgcagtggc tcaccctgt   13020
aatcccaaca ctttgggagg ccaaggcagg tggatcactt gaggtcagga attcaagacc   13080
agcctggcca acatagtgaa aacccatcgc tactaaaaat acagaaatta gcctggcatg   13140
gtgttgggtg cctgtaatcc cagctactca ggaggctgag gcaagagaat ggcttgaacc   13200
```

```
caggaggcgg aggttgcagt gagctgagat catgccattg cactccagcc tgggtgacaa   13260
gagtgaaact ccctctcaaa ataaataaat taataataat aatactactt aaatcatagg   13320
gttgtgtgga taaaatgaga taatataggt aaagtgctta atgcagtggc cagcgcatat   13380
agtaagcgct ataaatttg tatttgctat tctttatag aggatgtgtg tgtgtgtgtg    13440
tgtgtgtgtg tgtgttcatg tgcatgcaca tctatgtgca gacggatgag ggctggaggt   13500
gtgtgtatat ggggtgtgtg tacactagaa gatgtttgtg ctaggaatct gtgcaggaga   13560
gcctggagcc tgtgcatgag gcagctgagg taatgtgcca actgagaagg ggtctgaagg   13620
gctgtgtgga tctgggtatc agcatggtgc gccatttgag gtgtgtatgt gtgtcttcct   13680
gtgagaaggc tttattctca cccttggttt ttctgttttc tttttaaaat agagacaggg   13740
tcttactctg tctcccaggc tggagtgcag cggtgcaatc acagctcctg cagcctcgaa   13800
ctcccaggct taagcaatcc tcccacctca gcctcccgag tagctgggac tacaggtggg   13860
tgccatcagg actggctaat taaaaaaaga ttttttttta tagagacggg gtgtccctat   13920
gttgctcagg ctggtctcaa gctcctgggc tcaagcaatc atcctgcctc ggcctaccaa   13980
agtcctggga tagcaggtgt gaaccactgt gcccggcctc acccttgttt ttgtatcagc   14040
cccatctctc ttttcaccag ttcctgaaat ccctcccgct gggccctgga tggcttccag   14100
tcctccacct ctattttctg ccctggctct aactagccct gtagcatcct ggggcgtttt   14160
agacacagtg gtttcatccc agggaggggt cccggggcaa aggtctcagg cagggcccag   14220
tgaacagggg ctattttagg gcaggcttct caccacagcc cgccccacag ttcaccacat   14280
gggtgtgatg cccccacccc cacccaatac acacatgaga gatcacttag agcaaagggt   14340
gagaggggca ggtggggcta gggtggagac caaagcactg atgtgacgga accatcagcc   14400
aggcaactgg acctggtgga tccaggaaga ctttctggaa gaggtgagtg gtgctaggta   14460
gaaaggatag gacccagaga gaagaggaag agaatatctg taaggatgac tggactgggg   14520
atcgagagag agaagctggg ggccctttct tctaggacct tggggcccct ctggggcaaa   14580
tcagggttca caaggttggc cccaccctaa actctccatt ctcacatctt aggaaaccaa   14640
gccctctcac cagtcggttc ctctctgagt gttgcaatgg caatgtttct ggcagggtgt   14700
gggggaccct tgctcaatga cctcctgccc tgttgctcag aggataccgc tgccagaaaa   14760
gggttggctc attgtgggc ttcccaaggt actctggtag ccccagcttc tgacctggtc    14820 cttttctctgg tatggggata ggaggagagc tccggaggta ggtatccact ctcactcagc   14880
caccacatga aaccctaggg tggctgggag cacagcaggg ttcagaggaa ggactgtttt   14940
ttgtttgttt gtttgtttgt ttttgagatg gagtcttgct ctgtcacccg gctggagtg    15000 cagtggtgcg atctcggctc actgcaagct ccacctccca ggttcaagtg attctgctgc   15060
ctcggcctcc caagtagctg ggactacagg cgcccacctc cacgtctggc taattttgt    15120 attttagta gagacggggt ttcaccatat tggccaggct ggtctcgaac tcctgacctt     15180
gtgatccact cacctcggtc tcccaaagtg ctgggattat aggcgtgagc cactgcgcct   15240
ggccggaaga actggttttt aggagatggt gactggggac tgtgagggag ctgagcatgg   15300
cttgatagaa atcctgttag agagatgatt ataatgttca aaatcatgtg tgtctgagtg   15360
tgttcgtctg ttaacctggc aggcaccca tgtatatgtg catgtgtatg tgtgtgtgct    15420
attgtgagct tgggcttgtt agagcctgta ttggcgtgtg atggggttgg cacgcacact   15480
catgcaaata tatgctgtga gtgttattgt gtgactgtgc tggtgggtca ggtgagtatg   15540
agtgtgaaag agagctggtg tgggtggttt gccctatgtg acgggggttg tgtaagtgtg   15600
```

```
ccaggggtga taggaaggaa agtgaaggca gaagtcatgc tggggcagag cccaggcctt   15660
ctggcttcct gaagagggca ggagctgggc agctgctgac agaaacattg gcagagactt   15720
catcttcctt gtccttctgt ctcaccctca ggtctctgac ccctcccaag gatcatgccg   15780
cagccccact gacccaggag taggggccta aggggtgagt ggggtagact gagggctttc   15840
agggtcagga aacagggtgg gggtggcctt cctgaacccc acaactcctc acagcctcct   15900
cctcctacaa ggaccctgtt gctaggtaac ggatggggga gccagaatga ggcagcttga   15960
gaggctgaag gctggaccca cgacaggaaa tggccttgat ccccctctgc agtgactctc   16020
caggtgcaga cacacagcct cacacacact cacacacaaa catgcgcaga tatatagaca   16080
tacatgcaga gatacacaca tccagagaca ggcacactgc tcccacacag agataggtgc   16140
acattcatag acacacagac acagagacac ccactcacac agacaggcac acacatactc   16200
acacagaaac acatgcacac aaacacggtc ttacagacat atacacatgc agccaaacac   16260
atacacagag acttttatac actctcgtat acacacaaac ctgcacacac agacagacat   16320
ccacaaagag ctgcacacac atgcataccc acacaggcaa actcacccat acttagagac   16380
acacaaagac gcacatgtac aagcacactg aaagagtcac agaaacacaa catatcaaag   16440
caataggacc caacctgagc aatatagcaa gaccttgtct ctactaaaaa tcaaacaaat   16500
tagccagggg tactgcacg cacctgtata gtcccagttc ttggggaggct gagaccagag   16560 gatcacttga gcccaggaga tcaaggctgc agcaagctat gattgtgcca ctgcactcca   16620
gcctgggcaa cagagtgaga tcttgtctca aaacaaaaca aaaaaagcaa agcaatagga   16680
ggcaaaaata tgcaaataag catagcaata tcccaatgta gaaagccagc cccagagata   16740
tagacatgag ccaatgggaa gagaagcact gaggggggac atactgtgag gcagactgaa   16800
cggtacagta ggtggcccag ttccgccttt atcccttaca ggggaggaccc caatctaggc   16860 ccaagaggga aagccacgtg cctgtatgag cgtatgagca tgtgcatgcg cgtgtgtgca   16920
cagggtggtg cacctggcag gggtccttga gtgaggcatg ccccattctg tagcagggaa   16980
cctggaatgg gctgtgtgtt ctgcaagaaa ttggagccgg tggccacggc caaggaggat   17040
gctggcctgg aagggactt cagaagctac ggggcagcag accactatgg gcctgacccc   17100
actaaggccc ggcctgcatc ctcatttgcc cacatcccca actacagcaa cttctcctct   17160
caggccatca accctggctt ccttgatagt ggcaccatca ggggtgtgtc aggtgagtcc   17220
aaggggtcgg aggcaggagc tgcctggatc ctgggagaaa ctgagggaag aagaagagat   17280
gcgaacttgc ccttaggagc ctccaggagg atgtggcaga tacaaccccg cttccaagat   17340
cacatgggct gagggagtct gtacagccct cccatcagaa accacagtct gcagggagg    17400 gtcaagaagc tctactccca gtctgagagg ggcaggatcc tgtgacagat gcaagtgaca   17460
aagagaaact tcttgccctt ttaggtgcca cttcccagat gggaagtctt cttggtgggg   17520
aagaggagga gtgggcaaca agggatcct ccatggtggg aggaatgggc ttgaagttgt    17580
gtgtcctaag ctgtggagac caaatcagaa attccttgga ccccaaaggc ctttgggaac   17640
cagagcacta aaggagtggg gaggtgcagc acctggctgg ggaacaggaa tttggggtgc   17700 agccccttg gtgcttctgc cccatgccct acctgctga gtagccctga ctctgcaggg     17760
attggggtga ccctgttcat tgccctgtat gactatgagg ctcgaactga ggatgacctc   17820
accttcacca agggcgagaa gttccacatc ctgaacaata cgtaagtgac caggccacct   17880
agtcagaaca ttgcctgggc tgggagcagg acacagacag gaatcccacc tggtccctag   17940
```

```
cctcagaatg ctccagccta gttgggaaca catatacata acaataaaaa ccctgggtga   18000
ctgcaactgt gtgctggttg agggggggtgg tgttgggcca ctgcacccgg cctggaggag   18060
atgattttta agctgaggct ataaaaatga aatagacggc cgggtgcagt ggctcatgcc   18120
tgtaatccca gcactttggg aggccaaggc gggtggatca cctgaggtca ggagttcgag   18180
accagcctgg ccaacatggt gaaaccctgt ctctattaaa aatacaaaaa ttagcagggc   18240
atggtggcgc atgcctgtaa tcccagctac ttgagaggct gaggcagaag aatcacttga   18300
acccgggagg cagaggttgc agtgagctga gattgcacca ctgcactcca gcctaggcaa   18360
cagagggaga ctccatttca aaaaaataaa taaataatta aaaaataaaa aataaaaatg   18420
aatagacagt gaaggaagag gtaagaaaag aggaagagag tgagagagaa tgagaataaa   18480
tgatgacttc tggaaaccac aaagtggttc accttaggtg gttcataaaa tatgggatgc   18540
agaatgggag agaacagagg ctagagaggt aggcagaggc agattctgcc aggctttttt   18600 ttttttttt ttttgagttg gagtctcgct ctgtctcccg ggctggagtg cagtggtgca   18660
atcttggctc actgtaaccc cgcctcctg ggttccagtg atcctgggac tacaggcaag   18720
agccaccaag cctggctaat ttttttgtatt ttcagtaaag atagggtttc accatgttgg   18780
ccaggatggt ctcgaactcc tgacctcagg agatctgcct gcctgggcct cccaaactgc   18840
tggaattaca ggcatgagcc accacacctg gtctctgtca ggcttttttaa gccacattga   18900 gaagtctaga ttttatccag aaggaaatca gtagccattt tctgtgggga agtgacctag   18960
tcagctgtcc tctgaattcc caatccccag cccaacccag ctggggagcc caaggaagaa   19020
gctaagagcc ctaagtgccc ccgagcttat tccttctgca gggacaagcc ctcccaggga   19080
agctgcagtg gctggggcag agcggacaaa agccccagtg gtgggggggtg tccaagatga   19140 gggtttggca ggattcatct ctgcagacct gtgtggctcc acctggcctc agggtgcctt   19200
gggggctgga ggtgctgctg accatgccct gttctgtgcc tacagtgaag gtgactggtg   19260
ggaggctcgg tctctcagct ccggaaaaac tggctgcatt cccagcaact acgtggcccc   19320
tgttgactca atccaagctg aagagtaagt agggattggg gcaagaccag ccctatggac   19380
aggaccctgg agtccagact ccaaggccac ctcttggaca agtcattgct ccagtccgag   19440
cctgtctcct tatctaataa ttttgtaagg tcattgtgag aacaaaagaa gattgtactg   19500
ataataataa tagtagataa tagagcatgt actatgttct gggcactatt caaagtactg   19560
tctgtgtatt aacggggtta gaaattacta ctatcctatt tcacaaatga ggaagttgag   19620
gcacagagaa agtaaatatc ctgtgcaagt tcacatggct agtgagtggt ggagctgatg   19680
tatgaaccca gatagttggg ctgcatttgc taagcattac acatattgcc tcccagtaaa   19740
aacaacagtg tatgagcttt aaaaaattgt aaagtgctga aaaagtgcaa gggagcatta   19800
ctaggaatta attctattaa ggaggcaaga atttttcttt ttcttttttct tttgttttt   19860 cttttcttt ctttctttct ttcttttttt tttttttttt ttttttttt tgagacaggg   19920 tcctactctg ttgcctaggc tagagtgtag tgtagtggca caatctcggc tcaccgcagc   19980
tttgacctcc ctggctcaga tgattctttc accatgcctg gctaatattt tttttttaa   20040 gtagagatgt gtttcgcca tattgcccag gctggtcttg aactcctgag ctcaagccat   20100
ccgcccatct tggcctccca aagttcaggg attacagcca tgagccaccg agacctggcc   20160
caagaggcag gaatttatca ttcattgaat accttttatat acttgagcaa gtatactaca   20220
gcaagtattt atctccttgg ttcacttaat tctcacaata acaccgttat attattagtt   20280
ttttaagaga caggggcgtg ctctgatgcc caggctgggg tacagtgaca tgattttagc   20340
```

```
ttactacagc ctcaaactcc tgagctcaag tgatcctccc acctcagcct cctgagtagc   20400
tgatactacc ggtgtgtgcc accatgcctg gctaattttt gtatattttt ttatagaagc   20460
agaatcttgc tatgttgctc aggctggtct caaacttctg agctcaagca gtcctctcac   20520
cttggcttcc caaagtgctg ggatttcagg catgagtcac catgcctggc cttgatatta   20580
ttattttaga cagagtcttg ctctgttgcc caggttggag ggcagtggcg taatcttggc   20640
tcactgcaac ctccacctcc tgagttcaag caattctcct gcctcagcct tccaagtacc   20700
tgggactaca ggtgcacgcc accacacctg gctaattttt ataattttag tagagacggg   20760
gtttcacgat gttggccagg ctggtctcaa actcctgacc tcaagtgatc ttcctgcctc   20820
agactcccaa agtgctgaga ttacaggcat gagccaccgt gtccggcccc ttgatattat   20880
tattgttccc attttacaga tgaggaaact gaggctcaaa aagcttttaa aaatctatcc   20940
tcacaaatgt catacatata tgagaaaaga agggattgaa gagactttgc agagtgagaa   21000
tccaggactc tgtgactgat ttgggttatg ggagtgggga ggaatcaagg gtggctcaaa   21060
gtctccttaa ggagctgggt ggatgatggc accatttgct aaggcgggaa acacaggagc   21120
aggtataagt tcatgagttc tagggggtac ttgttggatt gtggtttgtg gagaggaaca   21180
tccaggtgga cgaagctgcc agcaattcga ttaggttgtg ctttgtatgg caggcaacca   21240
gcccatgcta atccatgccc ctgaatcagc ccagaggaag ggacaccttt tcttaattgc   21300
cactaaaact cctcagtttg tttgctgtgg cccttgcaga gggcacaacg ggctagggca   21360
gaaatttggg actcatgaga gtaaagatga tcattaaggc tatataggag ggggctgggg   21420
gcggtgacac atgcatgtaa tcccagcact ttgggaggcc gaggcgggcg gatcacatga   21480
ggtcaggagt tcaagaccag cctggccaat gtggtgaaac cttatctcta ctaaaaatac   21540
aaaaattagc cgggtgtagt ggcaggcacc tgtagttcca gctactcaga aggctgaggc   21600
aagagaatca cttgaacctg ggaggtggag gttgcagtga gctgagatcg agccactgca   21660
ctccagcctg ggtgacagag caagactccg tctcaaaaaa aattaattaa ttaaaaattt   21720
ttaaaaaagc tatatagacg gttaaggaag agagtggaga gtgcaaaagg ttggccctag   21780
gaccccactt tggggaaagc tgccctcgaa ggagaaggag ccattggaga agagaggaaa   21840
tccagaccag gccaagtcag aacaaccgag agagcggaga agcttcagga aacaagagag   21900
ggcgtgtcag aggctaccgc tggatttggc agtgggggtg accttggtga gagatttctc   21960
tgtgtgaggg tgggaggcgg aggccagaca gcagagcctg ggagggagtg ggaggtgagg   22020
aagtggagac ccaagtgtga agcactttt caagtgaagg gaaggcgaga agatacagca   22080
gaatgttgac ggcaagatgg aacttagaat agtttccttt ggggaaggga gaaatgtggg   22140
catgtttgga ggttgttgga atagagaggc tgcatgcagg tggaggctgc tggcaggaag   22200
tgggtatcac tgagcaggag cgggtaggcg aggttcagag gtcaagtgcg gtgaggccca   22260
agtctgggga ggtggtagga ggcgtgaaga agaggacgga caattatgca gaggacagga   22320
ggtttgtggg gagcttcatg cttgtgtcca catcttggag ccagtgtcac caagcactga   22380
gaggtgctca gtgcagtgtt gtggttacgg gtagtgtggt taggagcaca ggccctaaag   22440
cagacagcct gggttcctgt tctagcaact gctgccctga ctgtctaatg gggtttaaca   22500
atagtagcta tctcacaaca ttgttaggag aattaagtga atacatacgt gtattaaggc   22560
agaccctaac acgaaatatg tgtgttatta ttatagtgat tattaaggag gtagctaatg   22620
tcatgcgtgt gggagcgggg agggctttga aaaaacttga caatgtgtcc tgtctataca   22680
```

```
gtccctcaac acttcctccg tccccctcct gcctgccctc ctggacacac cacttgccaa    22740
tgccttcccc tgtttcctga actgtgccta gtacccaggg gcggactgac cttcccaggg    22800
tccactgaga cttccaccac ccttggtttg aaaacacgag gctcctttaa ttcaacccaa    22860
gatggccaca ggccagtttc atgatcatct gagtcttcta tggcacctgt ggtcacttca    22920
gctcccccat tgtacctgca cagttggttt agggctacgg ttcaatccca gaaagaatcc    22980
ccaagggaga ggagtgattg aggcctgagg ttgaagttta gacttaggac aacatccaag    23040
tctaagagag tgcaggaaga gcagtagccg gggcgggagc agccagagag aagagaagca    23100
ggagactgtg ctgctctgga ggccaaagga ggaaagagtt tggaggtgga ggtgggagaa    23160
ggatctgagt gatctgatta ctggagtggt gaaaaaagaa ctagggagag cggcagagga    23220
ttttaggtgg agctcattag ccagcctgtg gacaggtcac tttccctctc tgagcctcaa    23280
cttcctcatc tgtaaaatga gtgcacagaa gggctacagt gagatgaact gaggctccat    23340
ggcaccctga tgactgtgat tgtagcaatt ttaattcaag agaaacctaa cgagaagaga    23400
tgctaacctt tgcagggcac ctactgtgtg ccaggcattt tacactcccc ttctctgtaa    23460
ccctcccagc caggatgtga agcaggtgta ccagccccat tttacacatg gggaaaatgg    23520
agtcttggct tgtgaggtga ctgtgcagga ggctgaggtg aggtttgagc agagcgtacc    23580
tgactcttgc ctgcctttcc caacaggtgg tactttggaa agattgggag aaaggatgca    23640
gagaggcagc tgctttcacc aggcaacccc caggggggcct ttctcattcg ggaaagcgag    23700
accaccaaag gtaggggtgg tgccacgccc caaggcgact gggaggccca gccattgggg    23760
tagggctagg agcggtaggc tgcttgggtt aaggccaaga ctgggaccag gtcctaggga    23820
tgctgctgtc gggcctctcc cagctcccag actagggcag aggagaacag cagatcaaaa    23880
gtgatcctct ccacaggtgc ctactccctg tccatccggg actgggatca gaccagaggc    23940
gatcatgtga agcattacaa gatccgcaaa ctggacatgg gcggctacta catcaccaca    24000
cgggttcagt tcaactcggt gcaggagctg gtgcagcact acatgggtga gggcaggggc    24060
ctcagatccc tgaaccaacc aactgaagca ttgtccagat gggggaactg aggcccagag    24120
aagggaaggg actaccaagc agtattggcc agacggaaac cagaacccaa ggatggggtc    24180
tgccagccca ggatccagct ctgtgagctt ctggaggaaa gcagtccttc accaagcagc    24240 acccctaat gactgagcaa ggcattggcc agtttcttgc ctcaaggcct caatttgtgg    24300
aaacttgatg gagtgtttgt gccgcctgaa tgccccacca aggcaccagg actgccctgt    24360
gggcagacag ggagccatca tcacaggcc ctgagcaggg ggtgacagag gctggtctca    24420
cttttgtgag aaactctggc tgctggtgga gcttggatgc caggggccaa ggcagagtga    24480
ggggtccatt agaaggcagt ggctgttgtc caggtgagag gtggtggagg ccagactaaa    24540
tcggtggcag tggagtaaag atgaagcaga cgattctgaa gctgggtagg aggcagaata    24600
ggcctgactt ggtggagaat tggctgtggg ggtgaaggga aggcaggagt caatgcccac    24660
gtttctgcct tgattggtta tgccaaggat gaggtccacg gaagaccgtg gcctcatgt     24720 ccacaccttt gcctggaatc ccaaccccat ttccacctgt gagaatccca ccttatcctt    24780
caaggcccag ctggaggcta cctcctatgg gaggccccca gtccttacag aaggcttaca    24840
gggatcatct ctccctctgg gtgccacccc cttccttggg caccaacatg ttcccctatt    24900
tagtggatcg ggttgccttt cttcctggcc tgtgacctca cttggggcct agttccttat    24960
aactgatctt agggtctggc accaggctgg gataggataa ggagtggagg gggtgtcct     25020 ggcccacctg tgactctact tcatgacccc tccctagag gtgaatgacg ggctgtgcaa     25080
```

```
cctgctcatc gcgccctgca ccatcatgaa gccgcagacg ctgggcctgg ccaaggacgc    25140
ctgggagatc agccgcagct ccatcacgct ggagcgccgg ctgggcaccg gctgcttcgg    25200
ggatgtgtgg ctgggtacgg agctcccggg ggccgggacg agggcctggg ctcggggagg    25260
agggtcctga caagacagcc tccgagcagg cacgtgaaac ggcagcacta aggtggcggt    25320
gaagacgctg aagccgggca ccatgtcccc gaaggccttc ctggaggagg cgcaggtcat    25380
gaagctgctg cggcacgaca agctggtgca gctgtacgcc gtggtgtcgg aggagcccat    25440
ctacatcgtg accgagttca tgtgtcacgg tcaggaggcg agcctggtc gggcgggatt    25500 cggggtgaag ttaagagggg agttttcagg cgtgggacct gggacgcgat ctgtgaggga    25560
caagggacaa tgggcagagt cccactaagg gaccaggtgt gtaaaacgac tggagggctg    25620
aggtgggagc cgggccgagt gagaccacta gggagctggg gaggggggcg gtgcctccgg    25680
tgttaggcgg gtagggcttg ggctaacgaa ggcagaatcg ggaatgaggg agggtctggg    25740
gcggagtctg ggtgggtcgt gtccggaaca ccaaggaaca gaagaaacga gatgtgggca    25800
gagtccgtgt ctggcagcag ggccaggacg agacaagtga ggggttgagg cacccgcggg    25860
gtcctaagtg agggggcgggt ccaggtggga ggggctgagg ggcggggtca agcgagagga    25920
ggaggggctg gggcccgggg tagggctttg ccgctgactt tctggcttct tcccaggcag    25980
cttgctggat tttctcaaga acccagaggg ccaggatttg aggctgcccc aattggtgga    26040
catggcagcc caggtaactg ggccagcagc ctttacctcc cggacctccc acctattaac    26100
tgttcacaaa ttctctgtcc cttcaaacgc tgggagggc ggccccgccc cctgcatcag    26160
ctgtgcctcc agctgtgcct gagaggtact gcctctcttt ctgggcctca gtctcccct    26220 ctggaaagtg ggttttcaa atggtccctc accctcaaa caggccacgg tgttgtgagt    26280
ccacatgagc tcccatctct ccacactatg gtcccccagg tagctgaggg catggcctac    26340
atggaacgca tgaactacat tcaccgcgac ctgagggcag ccaacatcct ggttggggag    26400
cggctggcgt gcaagatcgc agactttggc ttggcgcgtc tcatcaagga cgatgagtac    26460 aaccccctgcc aaggtgccct gcttcacccc accttccaag agctccccat gcaacaaggg    26520
acttccatgg ggccccacgc actcaggaac ccttcctcac tccaggtcgc ccgagtcgcc    26580
ccatcctgat gtagtatgag aggcaattct gggctcaaat cccaggtcgg ccacttacca    26640
gccatgtggc cttgggcaag tcacctaacc tctgggagct gccgtttctc ttctgtaaag    26700
tgacaatatt cagataacag gaagtcagca gatgtttacc aggcacctgc tatgtgacag    26760
gcacagctat aattcttgaa tgaaagacaa tggcgtgtaa cagtgggaat tctgtagcca    26820
gaatgcctga gtatgaatcc cagccaggta ttaactctgt gatctgggca agttacctaa    26880
ctactcagtg tctccgtttc ctcgtctgta aaatgagtct ctatctcatg ggggttttgg    26940
gagggttaaa tgagttaatg catgcatatc acttaaaaca gtgtctggca cacaggaaag    27000
gctagccaag tattggccgt tattaggata agaattattg cgattttggg aaagtgccca    27060
tcactatact agacacatag taggtgttga ctagatacca tgtcctttct actatgccca    27120
gagacccttg tgctcaggat ccccgaaatc ctcatcccta gagtcccca ttctctctctg    27180 tctctttttt tttttttttt ttttttttga gatggagtct cactgtcacc caggctgaag    27240
tgcagtggtg cgatctcagg ttattgaagc ctcccaggtt caagcaattc tcctgccgca    27300
gcctccctag tagctgggat tacaggcacc cgccaccatg cccggctaat ttttgtattt    27360
ttagtagaga cagggtttcg ccatgttggc caggctggtc tcaaactcct gacctcaagt    27420
```

```
gatccgcctg ccttggcctc ccaaagtgct gggattacag acgtgagcca ctgcgcccag   27480 acccattct cttaatccag ctgtttccag ggaccccctc actaactttc cctgctcccc    27540
catcttctcc aggttccaag ttccccatca agtggacagc cccagaagct gccctctttg   27600
gcagattcac catcaagtca gacgtgtggt cctttgggat cctgctcact gagctcatca   27660
ccaagggccg aatcccctac ccaggtttgc ctcgccaggg gtagggctgg ggtgggggat   27720
ggtcacgggg aagggcttcc acctggctgt cccctttgact gacagagacc catccttcag  27780
gcatgaataa acgggaagtg ttggaacagg tggagcaggg ctaccacatg ccgtgccctc   27840
caggctgccc agcatccctg tacgaggcca tggaacagac ctggcgtctg gacccggagg   27900
agaggcctac cttcgagtac ctgcagtcct tcctggagga ctacttcacc tccgctgaac   27960
cacagtacca gcccggggat cagacatagc ctgtccgggc atcaaccctc tctggcggtg   28020
gccaccagtc cttgccaatc cccagagctg ttcttccaaa gccccaggc tggcttagaa    28080 ccccatagag tcctagcatc accgaggacg tggctgctct gacaccacct agggcaacct   28140
acttgtttta cagatggggc aaaaggaggc ccagagctga tctctcatcc gctctggccc   28200
caagcactat ttcttccttt tccacttagg cccctacatg cctgtagcct ttctcactcc   28260
atccccaccc aaagtgctca gaccttgtct agttatttat aaaactgtat gtacctccct   28320
cacttctctc ctatcactgc tttcctactc tccttttatc tcactctagt ccaggtgcca   28380
agaatttccc ttctaccctc tattctcttg tgtctgtaag ttacaaagtc aggaaaagtc   28440
ttggctggac ccctttcctg ctgggtggat gcagtggtcc aggactgggg tctgggccca   28500
ggtttgaggg agaaggttgc agagcacttc ccacctctct gaatagtgtg tatgtgttgg   28560
tttattgatt ctgtaaataa gtaaaatgac aatatgaatc ctcaaaccat gaaatacccct  28620 tgaaccttcc tttgggagcg ggggtggtca ataggggtg aacggacaga tatggctaca   28680
ggcagcagca ggggaagctg gagagggccc taatgcctac caagcacggg gcatccaagg   28740
tgtggagttt tagaacaccc agagtcccac tgctcatctg cacgtgagtt tagaagacaa   28800
gcagctgaag atacattaaa atgtccccctt cgttgctgat atggccttca atctgtgtat  28860
aataggtttg ctaattcttt atctgagttc atcagatttg ccattcatca caggcgcaat   28920
gggacaacct taggcctcct ttgccagggc agggaggaag accacagtgg accctctgga  28980
gctgtcagac tctccaaaag aggacagaag agaggggagg agagagaaga ggcctgaggg   29040
ttagtctaac tcactggatc tcattagggg agttttgccc ccaggggagc ttttggagag   29100
gtttgaaggc agtttgattt gtttggatcc tacaggtagg gttcagggat gctgaacaat   29160
ctgcagtgca cctgcgcgat gatgaatctt cccactccct cgttcccctg agagaaactc   29220
tggaagctga catgcctccg tgtggaaaca aggggagcag ggaataaaga ttccacctc    29280 tcccatcaga aaatgtttgt tgaccatctg acttactaag ggaatggaca gagaaggaat   29340
ctgggagctg ggaatcactg cagcaattgg caaatcatta ctgagcattg actctgcaaa   29400
gcattgactc tttgctaagg aggaccctgg gaacacaaac atgaataaga cctgtccctg   29460
ccctggagga ggagttcata gtcaagcaga ggaggaaaat tataataata ataactcact   29520
tattaagtgt cttctgaatg tcagatgtat ttacagccat cttttcaatt taatccagta   29580
ctgagcctgg ttctgtgatt agccccattt gtaggtgaga aaactgaggc tcagggtta    29640 catgatgtac caagagcatg cagtgtatgt gacagagcta ggatttgaac ctagatctta   29700
caccaaagct catggtcttt tcactagact tcattgcctc taggctttgg gaagagagcc   29760
tctgtggagt gtgtgtgtgt gcgtgtgtgt gtgtgtgtgt gtgtgtgtgt gatccttcct   29820
```

-continued

| | |
|---|---|
| cctctagtta ttggtagaaa gattccctgg aaatcctcct atgctgggtg acctaaagga | 29880 |
| aagaaagata aggcaatcaa tgcagattga gaattccctg tgtcctgccc tgtgctgggg | 29940 |
| gttgctgaat gagagcagta agatggagag aagccaaatg gctgctcaga ggggttgtca | 30000 |
| t | 30001 |

<210> SEQ ID NO 3
<211> LENGTH: 7682
<212> TYPE: DNA
<213> ORGANISM: Homo sapiens

<400> SEQUENCE: 3

| | |
|---|---|
| tggtgtgtgc ctgtaatccc agctactcag gaggctgagg caggagaatt gcttgaagcc | 60 |
| gggagacaga ggtggcagtg agccgagatc acgccactgc actccagcct gggcgacaga | 120 |
| gtgaggatcc atctcaaaaa aaaaaaaaag gaatttcttt gtgatttacg atgttgagca | 180 |
| ggttttcaaa tgttttggtc attcttatct tcctttgcga attacctgtt caaatatttt | 240 |
| gcccatttaa aaaattggat tgctttatta ttattattgc agtagcagtt gatataataa | 300 |
| ggagtccgta aacagaccca cagtcaattg atattcaacc aacgtgccaa agcaattcaa | 360 |
| tgggaaaaga aaatctttt caagaaattg atatgaagaa acaaaacctc aacccagctc | 420 |
| acactataca ttaatttgag atgagtcata gacctaaatg tcaaagttaa aattataaaa | 480 |
| gttctagaaa aaaacataga ggtgattttt atgatagcgt aagtgaagat ttcctgaaga | 540 |
| agatacagca ggcaatattt ctttctttt cttttttttg agacggagtc tcgctctgtc | 600 |
| gcccaggctg agtgcagtgg cgcgatctcg gctcactgca agctccgcag aaggcaatat | 660 |
| ttcacagagg aattctttgt gggcctgggc ctgacttgca atgggccagt tcctggggta | 720 |
| ccatgggtgg gaattgggta aaacttaccc caggttctta tcacacggga ccccagaggc | 780 |
| ctgggtggag gcttgtgact aactacatga gctttgccac gtactcctca ataccctctga | 840 |
| caaggactta ctgcagtgtt tggtctcacc aagtttccca caataaagag acatgagtca | 900 |
| cctttcaaga cccttttaccc ccaagaatgt ggtcttcaca catgagacca aggtctacaa | 960 |
| gtggtcagga gagagggggt ctgctcagat gggggagtag tgcctgagct ggcctcaaga | 1020 |
| gggttaagtg gccctgcact gaaaacctgg acactgagtt agggtagggc tgggggaaaa | 1080 |
| cttgggctttt ggagtcgtag ggtctgggtt caaatccaca gaccattccc ttcctagctg | 1140 |
| tgtgttggtg ggtaattcac tggatctttc tgagtcctgg tttcctcatc tgaggtaaaa | 1200 |
| cgagtttgcc ggttggtctg agagctgttc taggcatggt ggggagaccc tgacaggcag | 1260 |
| aggcagccct gctctcaagc agttgattta cagctgggga acaagacag ccacaaatgc | 1320 |
| aatacctcaa actcaacttc tcaccagaaa gctccttttc ctaattttca cagccagtcc | 1380 |
| ctcagcctcc tgggccccaa atactagtaa aacctttgcc tcctctctct tctttctttc | 1440 |
| ttgtaatcat ataggtacaa agtcctacca attcttcctg aaatatgttt ccttatcaaa | 1500 |
| aagtcctgca aagccgtgcg tggttgctca tgcctataat cccagcactt tggaggctgg | 1560 |
| gaggatcgct tgagtccagg agttcgagac cagcctggac aacatatgga gacccatctc | 1620 |
| taccaaaaat tttaaaatca gcaggggtgg tagtggcaag cacctgtggt ctcatctact | 1680 |
| tgggaggctg aggtgggggg attgttggag cctgggcggt tgaggctgca gtgatctgtg | 1740 |
| attgcaccac tgcactctag cctgaggtac agagcaagaa cttgtatcag aaaaaaaaaa | 1800 |
| aaaaagtcct gcggtagctg acactgccat tgcctatacg attcccattc cctcatcctc | 1860 |

```
cctagcagga tatcaattttt gttcgaagtg tcaatgaagg ccaggtgcgg tggctgatgc    1920
ctgtaatcct aacactttgg gaggccgagg caggcggatc acctgaggtc aggagttcaa    1980
gaccagcctg gccaacatgg tgaaaccctg tctctactaa aaacacacaa attagcaggg    2040
catggtggcg tgcacctgta atcccagcta ctcaggaggc tgagacagga gaatcacttg    2100
aacccggagg tggaggttgc aatcagccaa gatcacacca ctgcacttca gcttgggtga    2160
caagagtgaa actctgtctc aaaaaagaaa aacaaaacaa aaacaaacaa caacaacaaa    2220
aagcaaagtg tcagtgaagg tccagcaaaa gactcccttc ctattgccct ttgcagccag    2280
ggtcatcatg tgacacagtt cagatcaatg agatggaggc tgagggtccc tgggaaagat    2340 gttttttccta tacaggtacc acctcttttca gcttcactct ttccatttttc cacgtgaaca    2400 ggccttgtag cctggaggag ctacagctgc cttttttgaga tgctgaggca ccctgtctga    2460
agaaggccct cacatcactc aacttgacta ctgggtgagc ccttggagag cttcccagc    2520 ctctgctctt caagccgaag taccacaggg gacacgagtc ccagagttac aggaccccag    2580
ctatggttca tgtgtaaagg gaaccattag gcaaccaggg gaaatgatga agaagatcta    2640
catttacaaa tgtggaaaga tgttcgtggt atattgttaa attaaaaagc tgtttaaaaa    2700 tagttttttgg gtcaagtgag atgactcact tatacttttta gtataagtat gtcccatgca    2760
atatctggaa cgtacttgta ctaaggggtt tctccctcca tcggcacatc ccaggcatcc    2820
tggcagctgc tggcctccag caaccccaca ttctagttgt gtgggagtgg ggtgtggcat    2880
ggaccctgtg ggctaccact gccctgagct gcttcttcac acactggtat ttgtatctgt    2940
ggtaaaccca gtgacacggg ggagatgaca tacaaaaagg gcaggacctg agaaagatta    3000
agctgcaggc tccctgccca taaaacaggg tgtgaaaggc atctcagcgg ctgccccacc    3060
atggctacct gggccctcct gctccttgca gccatgctcc tgggcaaccc aggtaaggcc    3120
ttcccctcgg gatcgatcct gatggcccac ccagcctcgc actctcaggc tggctgaacc    3180
tggagcttgg actctgtggg cacccaggtg cccctgcctc cccccggcct tctccccccgt    3240 catggaggcc tggcctcccc tcagagccag gcttagtcca gtgtgctgcc cagcctgtca    3300
ctggcctggc caaggaggag agacaggcca gggattctgg tcctaactct actggccaca    3360
ctgtgtggcc tgagaccccc ctttccctcc caagcccctg cctccgcatc tgcgtggtga    3420
aggccattgg ccctcatcgg tggatctgcg tttcctcggg cctacactgt ctaggattgt    3480
gcggggctgg tgagagaaca agatctcttc tgtgttcaag gcagacttcc tgcccccctgc    3540 accctgctct ctcccaggcc ttgaggtcag tgtgagcccc aagggcaaga acacttctgg    3600
aagggagagt ggatttggct gggccatctg gatggaaggt aaaaaaagaa aatcccttga    3660
aaggagattg agggaagttt ctagacaaac cgacccccaa atctgtgttg ctggggggaac    3720 agaggagaag agagagtctc gccctcctgg ctttctagaa ggaacgtgag aacacgtgtt    3780
tgtgctgaga gtgggtcaga gcggctccag ggcaaagcat gtggacaggt atcctggccc    3840
cctgcaaggc ccagctcctg tcctaggccc tggtcacctc ctggactccc accagccagg    3900
agaacgggct ttccctctcc ttccgcctgc ggaggggaag ctgaagtctg tcttcctca    3960 ggtctggtct tctctcgtct gagccctgag tactacgacc tggcaagagc ccacctgcgt    4020
gatgaggaga atcctgcccc gtgcctggcc caggagggcc cccaggtacg tgttggctct    4080
ctgctcacct gccacagtcc ctctcctttc cctcctcccct ggtggctcct gggtgaggt    4140 ctggagctct ctaatggtca ggaggtggga gtggaggctg gctgtttttct gacgatgctg    4200 gttttgttga attcatgtct ggccaggagg gctacaggta tctggcagac tcctccagga    4260
```

```
ggatcctctg gggtctcacc ctccaaggag cctggggctg cagaacccaa ataggcagac    4320
tcccctggga gttcctcaat aggagagggg caagtgcagg gctgggaaag tactgggggt    4380
gtgggaggct gtttctgggg tgtctcagag cctctaagac aagcaaaagg gtgggcaggg    4440
gccaggcagc cagttcaggc cttcagtgta tccacgctct gggaagagat cacggacatt    4500
cctgccggcc tcagaaacac aaagggcccc tttcctgggc actttcacgc gctcccagag    4560
tgtctgagag accatcataa gggctttctt tcctgacagg gtgacctgtt gaccaaaaca    4620
caggagctgg gccgtgacta caggacctgt ctgacgatag tccaaaaact gaagaagatg    4680
gtggataagc ccacccaggt gaggccaagg ggctacagag cctcctgtct gctgctcaat    4740 ggagggcca gcctgtgacc aggtcgggga tcggggagcc cggggcacc ttgcacagtg     4800 atcctggggg agggcttcct agaagggaat ctgtgagtcc ccgtgtgtct gtggatgaat    4860
ttcagagaac ttgtgaaatt gtgactctct ggaactgtgt aagtcagacg gcagagtata    4920
catggttttc atcatgtatc ctcaaagagg gcttgtccca gagaagttag gaatcttccc    4980
ctaaagccct aacatttgtg tccaaggcag agtttgagaa gctagttccc caagaggcct    5040
gggtcaggac tgataaatcc cagatctgct acttccaagc tgcatggcct tgggcaagtc    5100
acttccactt tctgagcctc tgttatctta tctttgaaat gtgatggata atagtcccta    5160
tcttgcaagt tgtcaaaccc ttttttttt ttttccttg agataggatc ttactctgag     5220
acccaggctg gagtgcactg tgtgatctt ggctcactgc aacctctgcc tccctggccc     5280
aagcaattct cctgtctaag cctcctgagt acctggggct ccaggtgtgc gccaccatgc    5340
ccagctaatt tttgtacttt tgtagaaaca gggtctcact gtgttccca ggctggtctc     5400 caacttctga gctgaagcaa tccacctgcc ttggcctccc aaagtgtggg attacaggca    5460
tgagccactg cacctggctg ctgaagcttt ttaaaagagc tgagggctgg gatgtactta    5520
gctccacgtc cagcactgag taaatgctta acgaatgact gtgttactac caagaattat    5580
tgtttcactc tccctccttc cctctcctct gctgccccaa actactcagc atcctggcac    5640
tgcaggctcg cacttagccc tggataccca gattcatcct cctcccctgg gatggcatag    5700
aagagacttt aaaaccaaat gagccaagac tccaagctct gaccacacct cccaccccac    5760
cagtcttctc tatgcacccc ctctatctgg agccccagc caggtcctgg acccaggtag     5820
ctacatggca gagcatttaa tgtgtgcctg gcagccatgg gcaccattct ccacacagaa    5880
ggcaggggac aggtgcacaa ggcgctgaga ccccagcagg gctaactgtc cttgtctcag    5940
gagccctacc tggccagtct tgggccaggc cttggggact gggagtaggg gctgagcccc    6000
gtctgtacag tctctggccc catgggcacc aggtgccagc cctcgcacc cagtactccc     6060 attgctaggg ctgctggaac ctgcagggtg gcagagctgg gcaggactca ccctataacc    6120
atgtccactg tggtgctgct gctgcagaga agtgtttcca atgctgcgac ccgggtgtgt    6180
aggacgggga ggtcacgatg gcgcgacgtc tgcagaaatt tcatgaggag gtatcagtct    6240
agagttaccc agggcctcgt ggccggagaa actgcccagc agatctgtga ggacctcagg    6300
ttgtgtatac cttctacagg tgagtgcaga ggtgacagca gggatacctc ctgagggttg    6360
gagacagctt ccccccaggat atatcaaagc tgcctcctta ctcccccatc tcccagcttg    6420
ggaaagtgtg gagaattgag cagatggact ttagctagaa atgtttgaga aatactgatt    6480
agagcttggg cttcagacac aggtggtcgt ggagtaaaat ctggtctcca tctctccctg    6540
gctgtgtgac cttaagcaaa taacttgacc tctctgagct tcagtttctt catctgtgaa    6600
```

-continued

```
gggagatag caatcctgat tttgagatt ggaatgagaa ttgaaggagg tcaccgtgtg      6660
tgtggacctg accctgggga aatgtcctca gactgaggct attcaaggtc atcagaccct      6720
cagtcaaact ccaatcccag cccagcacag gcccctgggg tcgggagctg ggccatatc       6780 ctcccccaca atcctgggcc ctgagatctg ggctagggaa cccttcaggc aggggagcat      6840
gaggcctttc cctccatggc tgcccaggct gtgcctggag agaacagatc tcggctgtag      6900
gaaatggggc cagaaagggg cctcggtgat tggctctggc agctcagctg gcacttgcca      6960
atgctctggg attttatgct ggcagatcgg gggtccccac catttcctgt cattggagct      7020
tgtggctttt ctattcaagg ccccacaacc tgctcaggct gccgactggc ttccaggatg      7080
tgcctctggg tgtgttcagt agggtcaggt ggctctggga ccttaagcaa gtaacattct      7140
gagtgcctgc ttctccttga ggacccacca catctgccca cagctggctg ttctctcctc      7200
tccaggtccc ctctgagccc tctcaccttg tcctgtggaa aagcacagg ctcctgtcct       7260 cagatcccgg gaacctcagc aacctctgcc ggctcctcgc ttcctcgatc cagaatccac      7320
tctccagtct ccctcccctg actccctctg ctgtcctccc ctctcacgag aataaagtgt      7380
caagcaagat tttagccgca gctgcttctt ctttggtgga tttgagggggt gggtgtcagt     7440 ggcatgctgg ggtgagctgt gtagtccttc aataaatgtc tgtcgtgtgt cccatacact      7500
gttgtagatg ttatggattt agtggtgaac gagacaacct taacagcatt cacacagtta      7560
gtcgtgaaat gcttactgag cactcaccac agccatgcgt tattcagaaa ggccaaggca      7620
cacagtggcg atgtccccag aagctctcag accagtggga tagaccagca gggttagagg      7680
tg                                                                    7682
```

<210> SEQ ID NO 4
<211> LENGTH: 8269
<212> TYPE: DNA
<213> ORGANISM: Homo sapiens

<400> SEQUENCE: 4

```
agtgagctgt gatagcacca ctgcactcca gcctgagcga gagtaagact atgtctcaaa        60 ataaaaaga aaagaaaaa gaaaataaat ggttgctaac tgccatgaga tttactgatg         120
tctatcataa gactatttca taaggctgat tctaatcaga ctatttacta cagctatgct       180
aataaatgtt atgtttatag aggcttattc cctaaaataa tatttactgg ggcctcctca       240
aataaaaata ctgtatttat agaggttttc tctaataata atgacaattg aagatttctc       300
taataattta ttgaggccta tttaaataga aatatttgcc gagacttatt ctagtaatca      360
tatttatagg ggcttactct agcaataata atgatataat tatgactcca gactcaggac       420
tccaacttac ctgctcaact tacttactca acattccccac ttgaaaagaa gaggcatctc     480
caatctcaca tatccaaaaa taagttcctg atctcacaca cagcctatgt gttcctccca       540
tggtcttccc catcttagga aatggcaacc ccattttta tttttactttat ttgttttttt    600 gagatggagt ctcgccctgt tgcccaggct ggagtgcagt ggtgcaatct cggctcactg       660
caacctccgc ctcccctcct gggttcaagt gattctcctg cctcagcctc ccaagtagct       720
gggattacag gcgtctgcca ccacgcccag ctaattttg tatttttagt ggagacgggg        780
tttcaccatg ttggccaggc tagtctcaaa ctcctgacct cgtgatccgc ccgcctcggc       840
ctcccaaagt gctgggatta caggtgtgag ccaccacgcc cggccaaaca acccccatttt     900 tatccagcta ctcaagccaa caactttggg attcaatgtt ggcttttttt tttttttttt      960 tttttgaga cagggtctca ctcttgccca ggctacaatg cagtggcgtg atcacagctc      1020
```

```
actgcagcct ccacctccca ggctcaactg agcctcccac ctcagcctcc tgagcagcta   1080
agactacagg catgcaccac ccactatgcc tgggtaattt tttaattttt tgtagagatg   1140
gggtctcctt atgttgccta gactggtctc tgtctactgg tctcaagtga tcctcccacc   1200
ttggcctccc gaagtgctgg gatcacatgc gtgagccacc ccagctggcc tgtgtctgct   1260
tttggtttcc tgtaaatcct caaagacagc acctggcaca tggtaatcac tcaaaagaac   1320
atttgttgaa cataaatct ttattcaggc caactgactt acataaagta agtgctgttt   1380
attgacttac ataaagtatt atttattgaa atgtactcta atgatactga gatttaatat   1440 cttttatca ttataatagc cattaaatat tatgactaga gtgcacctca atagaaatga   1500
tgatgccttc cataataact gtttaccatt agcattcatt tctttaatag aacgtaggtt   1560
aattgaggat tagtcttttt aaattttatt ttattttatt tttttgaga tggagtctca   1620 ctctgtcacc caggctggag tacggtggtg cgatcttggc tcactgcaac ttctgactcc   1680
cgggttcaag cgattctcct gcctcagcct cccgagtagc tggaattaca ggtgcacgcc   1740
accactccca gctaattttt tggggtcttc cgtggcagat ggggctact gaggagcttt   1800 caagcccggg agaggttgga aggggctgga gaaagttgga agagacctgg gtgattcaaa   1860
aaaactgaca gtgcttagac aagactgaca gagacctaag agaaccaagt ggccaagcag   1920
gcgacgtgag ctgtgaaccc cgaaaatctg acaggtct cagttaattt agaaagttta   1980
ttttgccatg tagtcacagc tactcaggag gctgaggcag gagaatggcg tgaacccggg   2040
aggcggagct tgcagtgagc cgagatcgtg ccactgcact ccagcctggg caacagagcg   2100
agattccatc tcaaaaaaaa gaacaataga aagtttattt tgccaaagtt gaggacatgc   2160
gcccgtgaca cagcctcagg atgtcctgac gacatgtgcc caaggtggtc ggggcacagc   2220
ttggttctat acattttagg gagacatgac atatcaatca atagatgtaa gaagtacatt   2280
ggtgcatcca ggaaggtggg gacaactcaa agcaggagg gggattccac gttacaggta   2340
ggtgagagac aaattgttgc attctttgag tttctttttt cctagatgga gtctaactct   2400
gttgcccagg ctagagtgca gtggcacaat ctcggcttac tgcaacctcc acctcctggg   2460
ttcaagtgat tctcctacct cagtctcctg agtctgagac tacaggcgtg caccaccatg   2520
cccggctaat ttttgtattt ttagtagaga tggggtttca ccatgttggc caggctggtt   2580
ttgaactcat aacctcaggt gatccacctg cttaggcctc ctaaagtgct gggattacag   2640
gcatggcctc ttttgagttt ctgataagcc tttccaaagg aggcaatcag atatgcatcg   2700
atctcagtga gcagagggat gactttgaat agaatgagag gcaggtttgc cctgagctgt   2760
tcccagcctg actttcccct ttagctcagt aattttgggg ccccaagatt ttcctttcac   2820
agagctctca ggaaaagctt cagaaggagg cctgggtttt cctctggca accacagacc   2880 acatctggtt gagaaagctg ctggagatcc tgcgagcaat tctgtcttca aggccccagc   2940
tgccttgcct ttgtgctctt aagagatggt cttggctggc tgggtgcggt cactcacgcc   3000
tgtaattcca gcactttggg aggctgaagc aggtggatca cctgaggtca ggagttcgag   3060
accagcctga ccaacgtgga gaaacccgt ctctactaaa aatagaaagt cagccgggca   3120
tggtggcgca tgcctgtaat cctagttact taggaggctg aggcaggagg atctcttgaa   3180
cctgggaggc agaggttgct gtgagcccg atcatgccat tgcactccag cctgagcaac   3240
aaaagtgaaa ctgcgtctca aaaaaaaaaa aaaaaaaaa aaaaaagat gaccttcact   3300 cacccgctct tactggcttg tggtgtctgt cagagggcct gggcctgtga tcagcctgtg   3360
```

```
atacctacat gtgcagagac tcactggagc caggtacagg tcacctctgt gtatgcatgc    3420
atgcatgggt gtgatggtgg tggtagtggg acccacttgg ggagatgaga aatgaggtta    3480
caggcttgga cctggaggtg aaaggagaat gaaaatggtc ggagttaggt atgaattata    3540
gaggttgcag agaagaatga aaagacagtg gctgggcgca gtggctcact cctgtaatct    3600
cagcactgtg ggaggctgag gcaggtggat cacctgaggt caggagttca agaccagcct    3660
ggccaacatg gcaaaacccc atttctacta aaatacaaa aaaaaaaaaa aaattagcct    3720
ggtgtggtgg cgtacaacca taaccccagc tactcaggag gctgaggcac aggaatcact    3780
taaacccagg aggcggaggt tgcagtgagc caagatcatg ccactgtact ccagcctggg    3840
tgacagagtg agactccatc tcaaaaaaaa aaaaagggtt gggatgggaa tgagaatagg    3900
gtcaagtttc aggaagagga tgggttgggg tttggagtag gggctggggt taataatgga    3960
gaggggtttg gtttggagat agggtggggt ttcagaatga gaatggagtt agatttgagg    4020
gtgggaaggg tataagggtt ggaactggga ataaggatga tgttgagttt gggaattaga    4080
atgacgttag gtttggggat gggggcgaat cggggatgg ggttgagtgt gtagttggga    4140
ctgagaatgg agttctattt gaggatgggg gttggagcta gggtggagat tacgaatagg    4200
gatgggattg ggtatggagt tgtgttcagg aatgggaata gggttaactt tggggatagg    4260
gatgggttga atttgtggtt ggaactgggc ttgatactga gtttggggat ggagttgggt    4320 ttgggggttaa ggatggcttt gggtttggga ggggtcagg gtcacagata gataggctgt    4380
gtgctctgac ctgctactca ctgcacacca tggcaggttt tccggagacc tggcctgctc    4440
atggcctctg ccacctctgg gagcctgtgc tcataaatgt gttctcagag tggtgcagat    4500
ctgagtgaag gatgggggct gccgatctga gtctctccaa taaaggagag gaaccagtct    4560
tccaggtcat ttcccattct ccacatttgc cagctgtcct gggactgctg gaccagttca    4620
tctccaagac agaggtcctc ttccagacta ctccctatgt attagtctat tctcacactg    4680
ctataaataa ctgcctggcc gggcgtggtg gctcacacct gtaatcccaa cactttggga    4740
ggccaaggtg ggcagatcac ctgaggtcag gagttaaaga ccagcctgtc aacatggtg    4800 aaaacccgaa aatctactaa acctgaaatc tactaaaaat acaaaaatta gctgggtgtg    4860
gtggcgggca cctgtaatcc cagctacttg ggaggctgaa gcaggagaac tgcttgaacc    4920
tgggaggtgg agattgcagt gagccgagat tttgccactg ccctccagcc tgagtgacaa    4980
gagtgagact ctgtctcaaa caacaacaac aacaacaaca aatgcctgag actgggtaat    5040
ttataaagga aagaggttta tttgattcac agttcagcat ggctggggag gcctcaggaa    5100
acttacaatc atggtggaag gtgaagggga agcaagccac tgtcttcaca gagtggcagg    5160
aagaaggcca agcgaaggca ggaagagccc cttaaaaaaa caccatatct tgtgaaaact    5220
cactcactat cacaagaaca gcatggggga agccggcccc atgattcaat tacctccacc    5280
tggtctctac ctagacacgt gaggattatg ggacacaat tcaaggtgcg atttgggtag    5340
ggacacaaac cctaaccata tcaccgtttc acagaggtca agttttcctg gccttctac    5400 ctgggctgtg gtaccgtcac cttatacctg ctcgtagatg aggtgttgcc aggacctgat    5460
ggtgtggatg gaagaggcta gcgtttgggg ggctggagaa ccctaaacca aaatccttat    5520
gtcccccaac accccctagg ccccccgatc ctggtgataa aggccaccag gctggagccc    5580
ccacccaagc agggatgcca ctgaactcat taatcagatg aggatgtggg tatgtctgac    5640
tctctgcaaa cctttcagaa ttgtgattct ctgctgtttg cctgcccttg gcatatgctc    5700
caaactgggg cccaggattc tgagctcctg cccgcctctt cctccctcag gacctggagt    5760
```

```
tcaggccccc agctccttcc tccttaagcc ccaggagttc taactcccaa gtccctcct    5820 tcagtagaga ccctagactt ggggacttcc tctcccagaa tggaagactg cataacccac    5880
aggaaagcat gacacatccc cagctgtccc ctccagccac atctgccctc cccttaatg    5940 tacaccctag cctgattggc ttcctcccac ctcaggcccc caagcctct ctctctcacc    6000 tcttccagga agccccgact tggtgttgaa ggttccatgg gtgggagttg tagaatctgt    6060
gacagaggca agtactaaac caccgcccaa accactgatg atctgacacc ctcagtgccc    6120
tcccccatca cacactaagc ggggaactgg accccaggga ggggagggag gacgttgcct    6180
gtgcaatcca ggaagggagg gtatgtgaaa agctaccggg aactgtgtga aaccaaacca    6240
gcctcatgtg acaaagcgca ggacccctca ctgccccaac tgcttgctgt tctctctttc    6300
ttgggctcta aggacccagg agtctgggtg cacagcctcc ttctctctga gattcaagag    6360
tctgatcagc agcctcttcc tcctccagga cccagaagcc ctgagcttat ccccatggag    6420
ctctgccggt ccctggccct gctgggggc tccctgggcc tgatgttctg cctgattgct    6480
ttgagcaccg atttctggtt tgaggctgtg gtcccaccc actcagctca ctcgggcctc    6540
tggccaacag gcatgggga catcatatca ggtaagggga atgggtgtcc tacagagggg    6600
ttgccagcgg ggatgggtgc tcagtggtct tctcccgatc aggctacatc cacgtgacgc    6660
agaccttcag cattatggct gttctgtggg ccctggtgtc cgtgagcttc ctggtcctgt    6720
cctgcttccc ctcactgttc ccccaggcc acggcccgct tgtctcaacc accgcagcct    6780
ttgctgcagg taaggactct ggactggact ggggcatcgc gagccagcga attcctgccg    6840
aggagctgag ccatctctct tgtccttgtc cccagccatc tccatggtgg tggccatggc    6900
ggtgtacacc agcgagcggt gggaccagcc tccacacccc cagatccaga ccttcttctc    6960
ctggtccttc tacctgggct gggtctcagc tatcctcttg ctctgtacag gtgactatcc    7020
tgcccactgc cctggggagc tttgggaggg tccagttggg gtccctgagg acagagggca    7080
ggggcaagtg cttaaactct ttctggctcc ccaggtgccc tgagcctggg tgctcactgt    7140
ggcggtcccc gtcctggcta tgaaaccttg tgagcagaag gcaagagcgg caagatgagt    7200
tttgagcgtt gtattccaaa ggcctcatct ggagcctcgg gaaagtctgg tcccacatct    7260
gcccgccctt ccagcccttc cccagcccct cctcttgttt cttcattcat tcaacaaaat    7320
ttggctggaa tctggttatt ttgagattaa ttctgccaag acataagcca actgtctgcc    7380
agctccatgg taggagctgg gcaccaaggg aaggtgaggg cccaccaggc cgaccagcct    7440
gcagggcgct cctgcccagt acgagtgccc ggcccgtgtg gacacaggct ccaacccgtg    7500
tctatgtctc cccttctcca gcacttttct tcctccctgt gtctttctcc ctttagctgg    7560
ctctcttttc cttctctctcc ctctctgatt ttgtcccct tgccagaact cagcccttcc    7620
ttgcactcag tcagttctct ttgcacattt ccccatgctg gggacactgg cacgggtcag    7680
acccaggccc tgcccagcag gggctcagtc tgtggggtgg tggggaggag gcacttacag    7740
accagaagca gttaatacag gccagacagc agtcccagtg cagggagaat gccggaaaaa    7800
gactgaccat attgtggagg gatggagacg acttttctgg agagaaaca tttaggagct    7860 tcttaagggc cagggaaagg taatatccag gcagagggcc ccaaagatga acgtgcagaa    7920
aagtcaggag tcttgtgggg atgaagatcg gtaatttagg gtcaggatat agaatgtggg    7980
gggcggggga tggaaaatga agagggagag gcaggtgggg gctgtggcct ctaatgtcat    8040
gctggacttt ctcttgaaca tgatggggag ttgggagaaa aattgtgggc aggggaggga    8100
```

| | |
|---|---|
| cagtgtcagc tctgggtgcc agaaagaccc ccctgtagac atggagggga ggccagaagg | 8160 |
| tgagggagga acttggcaat gcaataggtg ggacatgatg aggcctgacc tgggaccagg | 8220 |
| aaaggaggga atgagccaga cagattcagg ggcaggagga gcaggactt | 8269 |

<210> SEQ ID NO 5
<211> LENGTH: 477
<212> TYPE: DNA
<213> ORGANISM: Homo sapiens

<400> SEQUENCE: 5

| | |
|---|---|
| caggggtcag gcaggtaatg aagtgatcgg aaggtgatga ggcagtggca gttgagattc | 60 |
| acgttgcagt cgccccaagc tggccaggcc agggagcaga agcatggctg gatgccggag | 120 |
| cccaccaggc tccccactgc agggcaagag tggcaggggg agagactgtg aaaggagcat | 180 |
| aggccaggtc ctgggtgaaa gctgtgtcct cagccttgac tgatgggtat agggagccac | 240 |
| taaatgcctt gggcagaga ggtgaggaaa aaaatattta ccgagcatct acaaggtgca | 300 |
| aggtactcac tagatgcctt cagtaccaaa gcttctcaaa cttagtatgc atatcactct | 360 |
| tctaagaatt tcattaaaat gcagattcta attcagcaga tatagggcag ggcttgaggt | 420 |
| gctgtcttta ataagctccc agtgcctggg actgcacttt gaggagaaga gctgtgt | 477 |

<210> SEQ ID NO 6
<211> LENGTH: 1800
<212> TYPE: DNA
<213> ORGANISM: Homo sapiens

<400> SEQUENCE: 6

| | |
|---|---|
| tcatccttcc cccagccagg gcctctgacc tctccactcc tgtgtccctt ccccccaggag | 60 |
| gatctctgcc ccactcagta tccggcagat cccttgttat tcttgtgctt ttagaacttt | 120 |
| tgctgttttt ggccaacttg aatcaacatt actgtctcct cgagcgtttc tctgccaggc | 180 |
| aggggactag gaaagcagga ctgcaggggcc tgctcattgg gttctaagat gtgggtgaat | 240 |
| tcggagtggg gttgtgcagg gctcccactg agaggagggc aggggcccct tgtgaagtgg | 300 |
| ttagctcgtc ttgtcaatag gtcctcagaa catcccttc agtctcttct caaagaagcc | 360 |
| cttttcaaacc aggcccttgc tcttctgtga tcgaagtgct tgacttttt tgctgttgct | 420 |
| cacatccggc ctgtcaaggt tgttttctgc cagcctggtc gtccatgcac cccatactat | 480 |
| tctcatggac tcatacccgt gaggaattgg gaggtaaggg caagcacctc agcacgctgt | 540 |
| gtgggacccc tagggttgca cctgggagga gcaaggccac acggacctgc tgtcagctcc | 600 |
| tatgctccca tctggctgga accaacccca agcttggggt tcagtgcccc cggcccatgc | 660 |
| actcagcatc tacacccatc acccacctgg cctcctggtc ttctgaccct gggatctccc | 720 |
| aaagaacaga gcagagccaa ggctggccag gatgagcgca gtctctctga gatgggacct | 780 |
| gaaaacaggg gcacccttgg caaggaagga ggcacacaga gtgggaagca gccaggcctg | 840 |
| gcttcgagtc ctgcctgggc actccccac aaggagactg tgggcaagtg acttcccttc | 900 |
| ccaagccgct gggctgctcc acagcagaaa tgtggcagtg gcgcacccct gaaggttgcc | 960 |
| gtggggagtg aggataaggc atgcagagtg cccggctcag actggatgac gacgacggcc | 1020 |
| agtggcaact tctctcctaa ttgtgcaagc aagcagtcat ggacaaatcc ttgtgagagt | 1080 |
| gactgtgtgt acaccaggac acagctgcac aaacaccatc cctaccctca taatgctcca | 1140 |
| gtttagtggg ggagacagac attaaacaca tccacacata agaggatggt gatgaagtgt | 1200 |
| catcaatttc acaaagaaga aataatggac tgagataatt gacagagtgg gggacctaat | 1260 |

```
atagcttagg gggtcacagg aggtctctat agaacagact tgctgcctaa ggagctacct   1320
aagtagtgag gatggagggg aagggtcaa ggctggagaa agcttagggc gtttgagaac   1380
tgaaatgagt tcatagtggc tacacgtacc cggcccatgt aggtaattta aaatttcctg   1440
gtgtgattga aaaagcaaag ggaaataggt aagttaattt ttaataagat attaaatgta   1500
aggcatctaa tgtaaggcat attatatagt ttcatcatgt cattaacata aaaattatta   1560
atgagatagt ttacatttct ttttaaatac tgagtctta agaatctggc aaatatttta   1620
catttatatc acatttcaac tgagactagc catatctcaa gggctcaata gccacatgtg   1680
gccagtgacc atcgtattgg acagcacagc tccggacatc ataatattgc aaccactact   1740
cccaggaaag actggttcac tggcacaggc ttcagacacc tgccagaagt gctttagaac   1800
```

<210> SEQ ID NO 7
<211> LENGTH: 2040
<212> TYPE: DNA
<213> ORGANISM: Homo sapiens

<400> SEQUENCE: 7

```
aatcatccct aaaaaccct gctttgcagg attctgtgtg cttatgaga gatgaggagt     60 atgaaaacac cttgtaaaac caggaggccc tttacaaagt cagaagcagc tcctcggtgc    120
tacagtctag ttgagggtct gactttagga agtcacaagg aacttagaaa tgggaagggg    180
cttccacctg acaacagcag ctctgccact ggaccgggtc ttccagccta gctccaccac    240
tcttctcatg ggtaaactct gccttcatct ctgttttctc atctctcaca caggctgaga    300
acacccagct ctcaggctgc cgggctgagg gtcaaatgag tccctgacca tcacgtgcac    360
agggcctgac ccaaggcagg tgctcaatcc ctggcacttg ctcttgttgc cttagagggg    420
accttgctgc ccacacccgt ctcagcccag acctggagca gcacttcatg tgattaccac    480 aaggggcgc ccctaagctt tccattcact ggaaccattt cattgaacct gtcattcagc    540
ccttccttcc acatccctac tgctatccta gagccaggag aaagcccttt agaaaggagc    600
tctgcagacc ccgaaggcat ctgctgtagg ttcagtgact cttagagaaa cagccctgct    660
ttccaaggcc aaacactgca tgtaggtaaa tttgtgacct gtggtggccc tcccaccaac    720
ctatcagctg agtgtcttca agttacttct ctaactttct tgggcctcag ttttcctcacc   780 tgaaaggaag agttggaaat aatcactctt ggtgcctgtg ggagtgcttt gtaaaccatg    840
gagtgagctg cacatgtgtt tcataactgt ccttttcatt gttcctataa accaaaaagt    900
atctgagaca ggtctcaata aatttagaga cttagtttgc caaggttaag gatgtgcctc    960
ccaaaaaagg aacacaaaat cccaagaaca acctgtgatc tgtgcttttt tccaagagg    1020 attttgagtg cttcaatatt tgaagaggac aagtaggcgg gagggaaag agggagcgta    1080 tggtcacatg tatggtcaca tgactgaatc tacatgttgc acgtgaaaaa aggcagaata    1140
ccaaaatagt caattatggg ctgggcgcag tggcttacac ctgtaatccc agcactttgg    1200
gagacggagg ctggtggatc acttgaggtc aggagttcca gaccagcctg ccaacacgg    1260 tgaaacccca tctctactaa aaatacaaaa actaggtgga catagtggca ggcccttgta    1320
atcccagcta cttgggaggc tgaggcagga gaattgcttg aacccgggag gtggaggttc    1380
cagtgagctg agattgcgct attgcactcc agcctgggca acaagagtga aattctgtct    1440
caaaaaaaaa aagaaaagaa aagtcaatta tttattcatc tggtgttcag caaatgttta    1500
cgtaagataa agtaagcata gggcagctac ctgtggagac acctggcctt ctatctgact    1560
```

```
gttattttttt tgttgttgtt tatttatttg tttgagtcag agtctcgcag tgtccccca      1620 ggctggagtg caatggcgcg atctcagctc actgcaacct ccgcctccca ggttcaagca      1680
attctcctgc ctcagccttc tgagtagctg ggattacagg cgcccaccac catgcctggc     1740 aaatttttg tattttact agagacgagg tttcactatg ttggccaggc tggtctcaaa       1800
ctcctgacct cgtcatctgc ccacctcggc ctcccaaagt gctgggatta caggtgtgaa     1860
ccactgcgcc cggccctatc tgaccttta tctgtagcta tattcttagg aacaaaagga      1920
aggcagttta ttctgtgact cagcttccag cttaatctct ccctttggca tagtgaatga     1980
aggtcccgag attttattt ccttttacat tcacatttag cagattgtac cacttgggat      2040

<210> SEQ ID NO 8
<211> LENGTH: 540
<212> TYPE: DNA
<213> ORGANISM: Homo sapiens

<400> SEQUENCE: 8
atgtcaccat taatcctcat gccgactttg ccatataagt ttaccctgat ttttttttt       60 tttagatgga gtctcactca ttgcccaggc tggagtgcag tggtgcgatc tcagctcact     120
gcaacctcca cctcccgggt tcaagtgatt ctcctgcctc agcctcctga gtagctggga     180
ttacagatgc acgccaccat gcctggctaa ttttgtact tttagtagag atgtgttggt      240
caggctggtc tcgaactcct gacctcaggt gatccgcccg cctcgacctc ccaaagtgct     300
gggattacag gcatgagcca ctgtgcccgg cctgccctga ttttaacaat aaggaaattc     360
aggcttagag aaatatctcg ccctaagcca cacagcttga gagtagcagg gtcaggattt     420
gaaccaggag agtgggattc caggtaattg tgggccggct ggctcatcac aaaactgtaa     480
cccaaaggct tgccagattt gcctgcacac accacttcct ctggggaaat gcagctacca     540

<210> SEQ ID NO 9
<211> LENGTH: 660
<212> TYPE: DNA
<213> ORGANISM: Homo sapiens

<400> SEQUENCE: 9
tttatcagga gctaatttgg ctcacactgg acccagaatc ccaccccca acttcatttg       60 tggtccaatt atagtctttt tttttttttt tttttttgag acggagtctc gctctgtcgc     120
ccaggccgga ctgcggactg cagtggcgca atctcggctc actgcaagct ccgcttcccg     180
ggttcacgcc attctcctgc ctcagcctcc cgagtagctg ggactacagg cgcccgccac     240
cgcgcccggc taattttttg tattttttag tagagacggg gtttcaccttg ttagccagg    300 atggtctcga tctcctgacc tcatgatcca cccgcctcgg cctcccaaag tgctgggatt     360
acaggcgtga gccaccgcgc ccggcccaat tatagtctta tattaaacag tatccactgc     420
agctcccaaa tatccataag atcacctgtt attagtctct tcgtgtcagt gaacctgctg     480
catttgtgtc agcaagtgca aggctgcctc tggacgtgtt cctcacctct gcactgtact    540
ataagcccct tggcttttgt ttttggaatg accctttgaa ataagtaaaa tcctgaaagc     600
aatagtttag gaaatctacc tgtcacttct gtagtcatac aatgccacat gtaaggttat     660

<210> SEQ ID NO 10
<211> LENGTH: 1140
<212> TYPE: DNA
<213> ORGANISM: Homo sapiens

<400> SEQUENCE: 10
```

```
accctctaat ccccagactt taaactggga ggtagcagag tggtctgatt aagaccttag    60
acaagggttt cttgtctggg cgcagtggct cacgcctgta atcccagcat tttgggaggc   120
caaggtgggc agatcacttg aggtcaggag ttcgtgacca gcctggccaa cgtggtgaaa   180
ccccatctcc actaaaaata caaaaattag ccagatgtgg tagcaggctc ctgtaatccc   240
agctactcgg gaagctgagg tggaagaata gcttgaaccc aggaggcgga cctcagcact   300
tctgcctggg tgatgggagt aaatcctgtc taaaaacaaa caaacaaaaa aaaaaactt    360 agacaatggt ttctcagctt tttttaatca ctccccaaca agtcctttta gatattatat   420
tcttttgtgt gtggcggggt acatagcgtg tgtatatgtt tgtaggttac atgaaatgct   480
ttgatacagg catgtaacgt gtgataatca catcagagga aatggggtat gcatcacctc   540
aagcatttat cctttgtgtt acacacaatc caatcatact cttttagtta tttgtaaagg   600
taaattaaat ttttttttact atagtgcccc tgttgtgctt gtaaatacta ggtcttattt   660
attctaagta ttttttgtgc ctattaacca cattatatat atatatatat atatatatat   720
atatatatat atatatataa tttttttttt ttttgagat ggagtctcgc tctttcgccc    780
aggctggagt gcagtggcgc tatctcggct cactgcaacc tccaccttcc ggtttcaagc   840
gattctcctg cctcagcctc ccaagtagtt gggattacag gcacccgcca ccacgcctgg   900
ctaattttta tattttagt agagacaggg tttcaccatt ttggccaggc tggtcttgaa    960
cccctgatct cgtgatccac ccacgttggc ctcccaaagt gctggaatta caggcgtgag  1020
ccaccatgcc tggcccacat tacattctta ctcacctccc cctaccatgg aattttattc  1080
cacagatatg ctattggttt agctactata tgtatatctg tgttttatac ataaagcaca  1140
```

<210> SEQ ID NO 11
<211> LENGTH: 900
<212> TYPE: DNA
<213> ORGANISM: Homo sapiens

<400> SEQUENCE: 11

```
acaggacagc caggtgagtt gggaagggaa gagagcctgc cacgggcaca ggcatgttgg    60
gggaagtgga agtggtgaga gcacagtagg aagtgagaag gggcgggccg tgcttaccag   120
gccgtggact taaaccagga tgagagaacc cctggaggcg tttaagttgg cagacttgga   180
tttcaggaag agctctctgg cttctgggtg gagaatggcc agtgggtaa gtggtgagag    240 gaaagacaga gaacggagaa ggttagatgg gcttgggaaa ttatccaggc cctggatgga   300
ggtagagatg tgtgctcatg aacacggagg ggattactga tgtggggtgg atgagactgt   360
cgtcaagagt gtgggacagg aagagaggga gagtcttggc cagatccaag aaaggagccc   420
tcagaagagg aggggagtca gaggcaagga aggggctgag gcagccagcc cagctgagtg   480
gaccccagga gaggtatcaa gggggtggtgt ggggtgggga ggggccagtg tcagaaagtg   540
gatggggagc ggcctgactc tgcttttgtc ctgtggcctt ctggccaaag gcagggaaag   600
gtggccaaac actgagacca agaacaaaga aagaaaactg ctggtggact tcttccacca   660
tgagcaggcc accaagcccg cagcactgca ctgcagcccc cagctctgtc ctggggttgg   720
gggaggtgag gaggggcaag gtggggagca cacagagcac ccgctgtcct cggaacacca   780
cagcgactag aggtaaggga gcaccggatg tggctgggat gtgggcagca aggggccaga   840
ggggccttga agggtcaca gaccatttaa tgaaggtgta ttgaaggcca ccatgggcca    900
```

<210> SEQ ID NO 12

```
<211> LENGTH: 660
<212> TYPE: DNA
<213> ORGANISM: Homo sapiens

<400> SEQUENCE: 12
agtgcctggg actgcactt  gaggagaaga gctgtgtgtg ccccagtgtg gtccagtgag      60
tactctgggc tccctctcgt gggcagggaa gctgagggcc ccatgagctc tcccagcttc     120
ctgaaggctc cccattaatg agagctgact gtgctgtgct ttgctgactg cagggcctgc     180
tccctgcccc ccacctccag gttggggtaa gtggcacctc tctccctcca gctccgcagt     240
cttccctgag gtttagatct tccaggttta taaagtcagg ccctcctgtt ggcagctggc     300
ctccaccctg gagtatctga gcttgcctgt ggcagcatct aaagatagtc tcccttacag     360
gaaacaagat actattggct aactctgcaa ataaaatgct cttagaggga aggaaaggga     420
aatactcgtc tctggtaaag tctgagcagg acagggtggc tgactggcag atccagaggt     480
tcccttggca gtccacgcca ggtaggtgca caggactagt tgggtacctg tgggtgsggt     540
ggagcagtgg acagctaata ggttaataat gcctgtttgc ttacgtgcag acaatggaaa     600 ccatttcct  gggatgttg  tagcctaaat atgtccaagg ggatggaaga gtgggaggca     660

<210> SEQ ID NO 13
<211> LENGTH: 2100
<212> TYPE: DNA
<213> ORGANISM: Homo sapiens

<400> SEQUENCE: 13
ttttgggttt tctttcttgt tgtgtttttg tttttgaga cggagttttg ctcttgttgc      60
ctaagctgga gtgcaatggc acagtctcgg ctcactgcaa cctctgcctc ctgggttcaa    120
gtgattctcc tgcctcagcc tcccaagtag ctgggattat aggcatgtac caccgcccgg    180 ctaatttgt  attttagta  gaggcggggt ttctccatta ataaattcct ggcacaaatt    240
tagtgttcaa ttttgatata tgttgttata accattgtga ggatactcag gctcaggttt    300
gtgtgggtgg aaaacatggt cttcagaaag aaattatgag tgcaagacag gaggaaatcc    360
atcagaggcc ccagctgagg actgaccacg gcttgttatt tctcttgcct tgcctctggc    420
aatcacagcc tcacagagcc tgcaatcctt gctttgtgag tttatagctc agtccagaga    480
atggctaaga aagtttagga ttcttcaac  acccactcca caaaaaaaaa aaaaaaaag    540 aaaagaaaaa aaaattaatt tttgaaatac ttgaggtaga aaacttgagg cagaaaaaaa    600
ttgagccaaa aaaaaggaa  aattgaacca cgtgaaagca ggcaagaaag cttgcattgc    660
tcagggcatc ccaggcccag agggcgcttt ggagggagct gggtttcctg agaggaggca    720
gggtgggtga cggacctgtg ctggagagcc ttgaggacca ctgtgggttg ggaatggggg    780
cagtggattg gggttcaaaa cccctgggaa tgagaaatgg gctcaggaag ctagggtgg    840 attctttcat cttcctcttt gcttggcttt attttcacaa aggaaggcag ggcaggaaat    900
agtctcagcc caacttcagt gtggttcttc ttagtgctca ggcttacctg gcacttgcca    960
cacctctggg atgggagcac ctactatcca tcagccacgt gccagtctcc acaaagtctg   1020
ctcctgaacc ctgctcctca gctggcccca cttcacagat ggggacatag gcagcttggc   1080
tttggaatga aggaatgaag tcaggaatga agtcctggct ctgcacttgg tgactgtgca   1140
ctgggcttgc taagtctgtt tcctgctttt aaaatggaga ttgtccatca gcctttgaag   1200
ccatgtaatg ggtatgtgtc aactttctgc aaggattaaa ggcatggtat aggaagtccc   1260
aaacacactg cctgacccat ctttgatgct caagaaacga tatatgttgt tgtcatgagg   1320
```

-continued

```
aaactgagcc tcagaaagtt tggatacctg aaaaacactg actactattg aatgaggttg    1380
tgaagaatcc agagctgtag gggcaggaaa gcaaagaacg tattagagct gacccagtca    1440
ggacgatcgt ctatccccTt cctcacccca ccccatccca ggaggaagcc tgcccggccc    1500
taggcagcta tggcacagtg gcaatgtcag gtatggttct ccctagccag agaccctagc    1560
ctcaaaaaac ctccttcttg ggatccaggc atccaactgc tcctcccag ccccagcctc     1620
tgacccagta tcctgagtcc agagacgttt ggaaccagca cctgtaatgg aggagctgaa    1680
caaggagggg aacttctgct gctccacagc aggtcacggt cataggaggg agtggaacca    1740
gaatggcaga atccagatct tggctgcctt tcccaaggac ttgttctgat tcctagcagc    1800
acagcccagg cattccgaga agttgggctc tctggcatca ctcactctgc cagaagagc     1860
caggggaaag ttggggcttc tagctgaacc ttgatcccac ctgccctctt gaggggctca    1920
gaatctgctg gctgcttcac aggtgggatt ctcacggcac gctggccaca gctgatgctt    1980
cgaccccctc atcttgtttg gccaaagtgc agcttttTag cttgtgagta aggaagaaaa    2040
gctgtatcat atgtctttaa acatcttcct agaccacctt tgttttcccc ttaaagtgtg    2100
```

<210> SEQ ID NO 14
<211> LENGTH: 1380
<212> TYPE: DNA
<213> ORGANISM: Homo sapiens

<400> SEQUENCE: 14

```
atgtattaag tgcttgctgt atgtgacaca ctgtgccagg tgctcccctt aaaacagttc      60
tgtgggcagg catgagaatg aatcccgatc ttacagacaa ggaatgttag gctcagaggt     120
ttcaagctca cccatcactc agccagagag gacagatgca ggattcaatc tcgggagtgc     180
ccgagtccac agaagttcct gtgctgaagg accgaccaca ggcacataaa gagatgcgag     240
acaatttta ctggatttgg ccacctctcg aggtcggctt tgccagctct tctcactggg      300
ggaaggggag ggagaaagta gctagctcca gggtccctaa catagaacca ccaaggactt     360
gactattttt actcatacag cagcttgtct gggaagatca tgctctgtga caagctgcag    420
gcactaagta gcaatttctg tttcccacat attagcttga gtcatataaa actgacatgg     480
atgtggctca aaaatagctg tatgtcagcc attttatacc atttgactta aatgttatta    540
attaacgtca cagccagaga ttattctctg agaaagggc attgtagcct gaagcagaga     600
aagcatacac gttccctggg gttgagaact catcacagcc tgagacagct taggttgtaa     660
agccccggcc cacttatccc aggagagtct gggtgagatg caggccccaa agcagaggct     720
gggaagcgag aagtgacaca ccctggctgg gtgggccctc atcttggtga caccacct      780
gggtaaaacc atcatggaaa gggtgtagtg gggcgtggaa actccctcgg ttaaagcgtg     840
agctttgctg taagttgtgg taaggaggga ggcagtgaca accaggaggc ctgttttgag    900
ggtttctgag ggacccatct gtggtatcac gaggagacgc ccagaggagc cgtgtgaaag    960
ggctgcctcc cagccggctc tggagtgaat gagcagcaag tcctggctgc gaaaagaagg    1020
ggagtgcagc ctgcagaagt gtcttctttt ttcaattcct gctcagaagg aaacaggaga    1080
taagaatagt ggggaagtcc aaaccaaagt gaactatagg gctggtaatc gtaggggaa     1140
ttagtcaccc ggagactagc ccagcagact aacggagccc catcctccat cttgaatcag    1200
tcagcccctc tatgactgca gagtcctgaa tgatggcaac accttctctt cacttagcgt    1260
tgtaggatga ccaacagtcc tgatttgcct gggactgagg ggttcccaat agatgggact    1320
```

```
ttcagggcta aaaccaggaa agtcctgggc agcccaaaac aaggtagtca ctctagagtg    1380
```

<210> SEQ ID NO 15
<211> LENGTH: 1740
<212> TYPE: DNA
<213> ORGANISM: Homo sapiens

<400> SEQUENCE: 15

```
gggcagtaaa agtaaaacag atctgtctca agcttcaaaa agcctagagc tggctgggcg      60
ctgtggctca cgcctgtaat cctagcattt tgggaggctg aggcggaagg ataatctgag     120
gtcaggagtt tgagaccagc ctggctaaca tgatgaaacc ccatctctac taaaaataca     180
aaaattagcc aggcgtggta gtgcacgcct ataatcccag ctatttggga ggctgaggca     240
ggagaatcgc ttgaacccca ggggacagag gttgcagtga gctgagatcg caccactgca     300
ctccagcctg ggtgacacag cgagactcca tttaaaaaaa aaaaaatgcc tagagccaaa     360
tgctcacaga gccatttact gcatggcttt gggcaagtca aaggagtccg cctctcctgt     420
cagaagagtc tgttgcagtc ttcatcacaa gactgttgtg gggattaaac aagatggcaa     480
gtgggaagtt gggaaatgta gtgtgcaccc aaccaatatt tgtttcttcc tgcctgccta     540
catatgaggc cacacagaat tccaactttg tttctctgat aactaacaca gttacttgtt     600
tttctttctg atccaggcct tcaccatgga tcagttccct gaatcagtga cagaaaactt     660
tgagtacgat gatttggctg aggcctgtta tattgggggac atcgtggtct ttgggactgt     720
gttcctgtcc atattctact ccgtcatctt gccattggc ctggtgggaa atttgttggt     780
agtgtttgcc ctcaccaaca gcaagaagcc caagagtgtc accgacattt acctcctgaa     840
cctggccttg tctgatctgc tgtttgtagc cactttgccc ttctggactc actatttgat     900
aaaatgaaaag ggcctccaca atgccatgtg caaattcact accgccttct tcttcatcgg     960
ctttttttgga agcatattct tcatcaccgt catcagcatt gataggtacc tggccatcgt    1020
cctgccgcc aactccatga acaaccggac cgtgcagcat ggcgtcacca tcagcctagg    1080
cgtctgggca gcagccattt tggtggcagc accccagttc atgttcacaa agcagaaaga    1140
aaatgaatgc cttggtgact accccgaggt cctccaggaa atctggcccg tgctccgcaa    1200
tgtggaaaca aattttcttg gcttcctact ccccctgctc attatgagtt attgctactt    1260
cagaatcatc cagacgctgt tttcctgcaa gaaccacaag aaagccaaag ccattaaact    1320
gatccttctg gtggtcatcg tgtttttcct cttctggaca ccctacaacg ttatgatttt    1380
cctggagacg cttaagctct atgacttctt tcccagttgt gacatgagga aggatctgag    1440
gctggccctc agtgtgactg agacggttgc atttagccat tgttgcctga atcctctcat    1500
ctatgcattt gctggggaga agttcagaag atacctttac cacctgtatg ggaaatgcct    1560
ggctgtcctg tgtgggcgct cagtccacgt tgatttctcc tcatctgaat cacaaaggag    1620
caggcatgga agtgttctga gcagcaattt tacttaccac acgagtgatg gagatgcatt    1680
gctccttctc tgaagggaat cccaaagcct tgtgtctaca gagaacctgg agttcctgaa    1740
```

<210> SEQ ID NO 16
<211> LENGTH: 660
<212> TYPE: DNA
<213> ORGANISM: Homo sapiens

<400> SEQUENCE: 16

```
cctattcaat tatttcctgt ggttaaattc attgccatgg ggaaaactga gtcaaagggc      60
atgggaacac attatctttg catacacaca tatgaaagtc atatattaca caaccttttac    120
```

```
tgagtcgtat tatatacaaa acatgaacgc agatccagag ctattccaaa ggcaatgaga    180
ccaagcctct tccctcaata atttaaatgc agaagagaag tgaaggaata atcacgcttt    240
gcattaggtg gtagcagagg agtactacgt gacttctgac ctgcgtcttt aagggacagg    300
ggttctccag gtaaagaaag aggtggcatt ccaggctgag gaaacagcat gtataaagga    360
agtgtgtgag agccacaatg tgagaaaact ctgtgcgaat attaaaaggc gttagaagcg    420
gagtgggtgg taggaacttt ctgagctgag ctgttagctg tgggctgagc taaaacaacc    480
aatggagggg gtgctggttc tcctcagggt gtttacgggg tttcttcgtt attacctgat    540
cctcattcca actgttgaac cataagactt ttaattaaag tttaacctat tcctggactt    600
ctaagaagga ggaaataatt attttggctt gagaaataaa agaagagaaa taaacacttt    660

<210> SEQ ID NO 17
<211> LENGTH: 410
<212> TYPE: DNA
<213> ORGANISM: Homo sapiens

<400> SEQUENCE: 17
ccagccccag agatatagac atgagccaat gggaagagaa gcactgaggg gggacatact     60
gtgaggcaga ctgaacggta cagtaggtgg cccagttccg cctttatccc ttacagggag    120
gaccccaatc taggcccaag agggaaagcc acgtgcctgt atgagcgtat gagcatgtgc    180
atgcgcgtgt gtgcacaggg tggtgcacct ggcagggtc cttgagtgag gcatgcccca    240
ttctgtagca gggaacctgg aatgggctgt gtgttctgca agaaattgga gccggtggcc    300
acggccaagg aggatgctgg cctggaaggg gacttcagaa gctacggggc agcagaccac    360
tatgggcctg accccactaa ggcccggcct gcatcctcat ttgcccacat              410

<210> SEQ ID NO 18
<211> LENGTH: 1500
<212> TYPE: DNA
<213> ORGANISM: Homo sapiens

<400> SEQUENCE: 18
tcaagtgatt ctcctacctc agcctcctga gtagctggga ttatgggcgc ccaccaccac     60
acctggctaa ttttttgtact tttagtagag acgtggtttc gccatgttgg ccaggctggt    120
ctcgaactcc tgacttctgg ttgatctgcc caccgcaacc tcccaaagtg cagggattac    180
aggcataaac caccacgccc ggttttttttt tttttttttt gagatggagt tttgctcttg    240
ttgcccagac tggagtgcag ttcctcaatc tcggctcact gcaacctctg cctcccagat    300
tcaagcaatt cttctgcctc agcctctgga gtagctggga ttacaggcac ctgccaccat    360
tcccggctaa ttttttgtat ttttagtaga cagggtttt caccatgttg gccaggctga    420
tcttgaactc ctgacttcag gtgatccacc cgcctcagcc tcccagagtg ctgggattac    480
aggcatgagc caccacaccc agctttagct ggcattttc tacaaagagg atcttcaact    540
agaaatgaac cacagtttct ccttaaaaag gcaggataaa tgcttaattc tctaaggaaa    600
gggttttgtt ttttcttttt aaacaagaga ttctagaatg tgtttgtatg ctaagaggat    660
aactctgtgg aaggaaaagc tggatggtac gagagatgga gttacagagg tgtaacatcc    720
ccagaaggtg agaggattta gaattcaggt ggggaaggag gagaaggggt aggatgttgg    780
aagacaaaag aaaagtgtg agctgctcat ctgggcagag tgatagggcc tgcttagtga    840
gaaatgcacc agaggattgc tgggcctggt tagtgtccta ttgaggctgg gagttgcgac    900
```

```
cctgtctgca tagcaagcag ttttctcctc cacatttaga aggtaaggga ggtcgggcgc    960
agtggctcac gcctataatc ccaacacttt gggaggccga ggcaggtgga tcacctaagg   1020
ttgggacttc gagaccagcc tgaccaacat ggagaaaccc tgtctctact aaaaatacaa   1080
aattactgca ctccagcctg ggcgacagag tgagactcca tctcaaaaaa aaaaaaaata   1140
caaaattagg caggcgtggt ggcgcatgcc tgtaatccca gctactcggg aggctgaggc   1200
aggagaatcg cttgaatctg ggaggaggag attgcggtga gctgagatcg tgccattgca   1260
ctccagccta ggcaacaaga gcgaaactct gtctcaaaaa aaaaaaaaaa aaaaaagaa    1320 ggtaatggtt agattcctgc aggcctgggt tttccaggca ggtacactgg agggagaggg   1380
agggagaggg aggccggaca gtgccaggtc tttgcaacga atgaccataa ggactgacag   1440
cagaatctag gctggttgaa agcaggagtg agaagaggag gagagtgatg gctagctggg   1500
```

<210> SEQ ID NO 19
<211> LENGTH: 720
<212> TYPE: DNA
<213> ORGANISM: Homo sapiens

<400> SEQUENCE: 19

```
gcaggggcca agcacacagg gcctcagagg acaagacaaa gctgctggat tttattattc     60
tttattatta tggtatcgta tgtattgtat ttttattttt ccaagcaaaa tgaaaggtaa    120
ggcactggga gattttaagc aagggactaa tgtggcccaa cacatatttt aaaaagtaga    180 agcaatttt tttttttgaga cggagtcttg ctttgtcgcc caggctgaag tccagtgccg    240
tgatctccgc tcactgcaac ctccgcctcc tgggttcaaa cgattctcct gcctcagcct    300
cctgagtagc tgggattaca ggcaccggca ccacacccag ctaattttgg tattttagt    360 agaggcgggg cttcaccaaa ttggccaggc tggtctcgat ctcctgacct caagtgattc    420
gcccgcctca gcctcccaaa acaatgggat tacaggcgtc agccaccgag cccggcctga    480
gaagcaatgt tgtcattttg ttcttccatt catttgctta ttcagtcatc aattcttgaa    540
tttcttcatt cattctttct taccttccat tatttagttt ttcactgggc tttccttttgt   600 tcatctgtta attcctttgt cctttggttg attcacgtgt tcctatacac agaaagcctg    660
ctactgtgtg ctgggccttg tgtgggtact ggaggcatct acaagagcca gaccctgcc    720
```

<210> SEQ ID NO 20
<211> LENGTH: 780
<212> TYPE: DNA
<213> ORGANISM: Homo sapiens

<400> SEQUENCE: 20

```
aagtaacagt ggtgggagtg gggactgaac cccagattga ggaggggtca gggatcccta     60
tcagacagag agactggaac tgatagagga tgctaccgtt tctctttttg tttttaaaaa    120
tcttttccca catgttctaa gatactcagt ttttcttcct tttttttttt ttttttttt    180 ttcttgagac ggagtctcgc tctgtcgccc aggctggagt gcagtggcgc catctcggct    240
cactgcaagc tccgcctccc gggttcacac cattctcctg cctcagcctc ctgagtagct    300
gagactacag gcgcccgcca ccacgcccgg ctaattttt gatttttagt agagatgggc    360
tttcactgtg ttagccagga cggtcttgat ctcctaacat cgtgatccac ccgcctcggc    420
ctcccaaagt gctgggatta caggcgtgag ccgctgcacc cggcctttc tttctttttt    480 ttaaaaaaag tcattttctg caacaaaacc cacattcttt ttttgtgttt tttttttta    540 aggcagggtc ttgctctgtc acccaaggta gagtgcagta gctcaatcac agctcactgc    600
```

```
agcctcgacc tgcctgactc gagggatcct tccacctctg cctctgcagt agctgggacc      660
acaggtgcac accaccacac cgagctaact taagaaaaat ttttttggt agagatggtg       720 tctccctatg ctgcctaggc tggtctggaa ttcctgggct caagcaatcc tcccacccaa      780
```

<210> SEQ ID NO 21
<211> LENGTH: 1740
<212> TYPE: DNA
<213> ORGANISM: Homo sapiens

<400> SEQUENCE: 21

```
ctaagggaag ggtcttctgc tgctcaccac ccttaacagc cctgtgtccc cagtgctcag      60
cccctgagga agggaaggcg tgctgacagg gtccatgtga tccatgtcca gtggctctgg     120
tgacagcagt ctgaagtcaa ctggctgtga aactcgagt aaggccagtc ccgatctggt      180
cctcagtgat ggagaaaagc ccctcttaac ctccaattca atgatcctaa aagagcaggt     240
gcttcggggt tgctgaaact gcgcttttgg aggggctttt gggaaggcc gggctgggga     300 ctcaggtctg gagggtgaca gagccgacct cccgtaaacc agggaggagg aaggtggggg     360
cgggtgggcc taggatctgg gggcgcctcc tcgctgcggg gagctggctt ggggctaggg     420
cgtgactgtc tccctgccac catcaccgcc cgccggccgt gactgcaata agagaagtcc     480
gaggcggctt cctcctccct gcccagcagg ggcggcggtc agaggcgggc agcaccccag     540
ttctccccgc acgccggcac tcgcggctgc tggagccccg gctggctcac cccggggccg     600
ggcagaattg ggctccaggt aagcgacagc gtcgggtggg gactgggcag gtcaagcagt     660
gccctccccc tcgaggctct ggagagagga ctggggtac acgggaagag aagcctgaac     720 ctggggtcg gggacacat gagcaaggtg acagccaaag gaccccagc ccgaaaaggc       780 ctaaggagga aaacgggcga cctgaaaagc aaggctgata aacctggagg agagggcgga     840
ggggagcacg gggaagccg accaaaggga ccccaaaaa ggtctagtgg gtaaaatgga      900
ggggactgat aagagtttag gaagggggct gaggtggggg agaaggatta aggggaatcc     960
ccaggacggt ctgggggaga aactgaaggg atcgtgagag tgggactttg gggagaagcc    1020
gacgggtctg atgggtccag gagaggggaa atgggtgggg gtgctggagg gaacaggaga    1080
gggagctggc gggaaggggg ttgaggagaa cgacttctgg aggacggaga acctggggtg    1140
caattgcggg tccaggaagt tcccctcttc cgagccggcc gaagtcgggg tgaagcccac    1200
agcccgcagg gtaacgttag cggccgcgac cgcggccccg cgaccctctc ggcccgccct    1260
tgcggtaggt tccgggctgc aggggactcc tgccgggcgc gcgaggcgtg ggtccccgct    1320
tcctggggaa gtccccgccc tcggcaggga caggcctctc cggcgcccc ctccgcgccc     1380 gcggcggtct cggcccgcgc tccccgctgg atccgggaat tgctgccgcc ccgacggaaa    1440
tcctgccttt gaccgcgagt gcccgcaggg gctgcctcca aggcaacgag agggcgggcc    1500
gcgctgggcc gccgcgggc tccggtggg cgcagccccc tttgctctcc gccttcgccc      1560 cctttggaa tcctcggtct ggtgggtggg gggtgggctt cccgaccgag gtaggaggcg     1620
atgccgctgt gttcagggat cctggggtgg aggatctgct gttgagaga cctgggttct     1680 tagcaagact gggcccttaa ttgctgtgtg actgtgggca agttacaggg cttctctggg    1740
```

<210> SEQ ID NO 22
<211> LENGTH: 1200
<212> TYPE: DNA
<213> ORGANISM: Homo sapiens

<400> SEQUENCE: 22

```
gccacactgt gaaatctaga ctcccatccc ttggctgccc ctggaccccc gcccccgcc      60
gccatggctt ccatctcctg aaaatcctga gtcccaggcc agatggcatc taaagagctg   120
tgttttagag gctggtgggt ggttttcagc aacaggtgga aaaccacttt tacccacaag   180
aagtggaaaa aactgctaat ggcctcggga ccacatggag ggtaaaggcc accccgatc    240
ctgcacacac ctggcctcac cacgtggtg gtggagtcag acagggttgg gtgggtatgt    300
cttcttcagg aggcagtttc gaggcctcaa gaaaggatgg tgtgagatga aggggggtta   360
atgaaggcag ggcacggtgg ctcacgcctg taatcccagc actttaggag gccgaggtgg   420
gtggatcacc tgaggtcaga gttcaagaa cagcctggcc aacatgacta aaccccatct    480
ctactaaaaa tacaaaaatt agctgggca tggtggcaga cgcctgtaat cccagctact    540
caggaggctg aggcaggaga attgcttgaa cccgggaggc agaggttgca gtgagccgag   600
atcgaaccat cgcattccag ccttggcgac agaatgagac actgtttcaa aaaaaaaaa    660
aagaagaaga agaagaagaa gaacaaagaa agaaagaaag ggagttaatg agcagtgggg   720
gcctcagcaa aggcactggc attcagccag gtggagggtc tcggtgagag gactgagggt   780
gagggatgga agcccgcccg gtctgaggga tagggcctag tgagagatgc ggcacagtgg   840
gatgggagtc acctgcagac ctcagccttg ctccctgacc ctccagcccct ggcctgcccc   900
cggccagccc agagcctgga ggagaagccg gaactcttgc aggatggtgg tttcctgccc   960
ctgcccaaag tcccggttcc cttttgatga atcccccag gcggctgggc cagctcagcc   1020
ctctcacctc accctgggaa cttctctttc ttctcagccc tgcccagttc tgtaccctct   1080
ggtcccacac cgtcactgcc acggaggacc ttcctcaagg gaaaggaggg aagtgaaagt   1140
tcactgggca cttactgtat gtctgatgct ttcagtgatg tgacccccatt tgatgctgag   1200
```

<210> SEQ ID NO 23
<211> LENGTH: 960
<212> TYPE: DNA
<213> ORGANISM: Homo sapiens

<400> SEQUENCE: 23

```
gcttatgtca aagatccaag gtcatagagc tactgaagaa tggagctggg gagggccaca    60
gggcagatgt tgaagtgagg agcactgcgg tccagggttg gacctcagtt tgatacttgt   120
aacctgattt tgaccctgat ggggatctcg gaggcgactc ctgtaaacca gatgttcaag   180
agacatattt ataaacagaa ccaagtgccc agaatgatgc tgtggctact ctctgagctg   240
cccccttcct ggtattagca ggcagcgaag ttcagtgctg agaaaagaga gacctggctt   300
cttcagattc agcgactgcc tgagaaaatc tgggcagata tggctctctc tctctctctc   360
ctgcgcccct ccctccccc acctgcgccc tgcctgctgt atcaaggatt tagagcatga   420
ggcacagggc tgagaacact aggtgctcct taagagacac acgttattgc aggggtgtcc   480
aatcttttgg cttccctggg ccgcattgga agaagaaaaa ttgtcttgag ccacacataa   540
aatacactaa cactaatgat agctgatgag ctttaaaaaa ttgcaaaaaa ggccgggtgc   600
agtggctcat gcctgtaatc ccagcacttt gggaggccga ggcggcaga tcacgaggtc    660
aggagatcga gaccatccgg gctaacacgg tgaaacccg tctctactca aaatacaaaa    720
aattagccaa gcgtgttggc agcgcgcctg tagtcccagc tactcaggag gctgaggcag   780
aagaatcact tgaacccagg aggcggaggt tgcagtgagc caagattgtg ccactttact   840
ccagcctggg caacagagtg agaccccgtc tcaaaaaaaa tcacaaaaaa aatctcataa    900
```

```
tgttttcaga aagtttacta atatgtgttg ggccacattc aaagctgtcc tgggctgcat    960
```

<210> SEQ ID NO 24
<211> LENGTH: 600
<212> TYPE: DNA
<213> ORGANISM: Homo sapiens

<400> SEQUENCE: 24

```
gggttggctc attgtggggc ttcccaaggt actctggtag ccccagcttc tgacctggtc     60
cttttctctg tatggggata ggaggagagc tccggaggta ggtatccact ctcactcagc    120
caccacatgg aaccctaggg tggctgggag cacagcaggg ttcagaggaa ggactgtttt    180
ttgtttgttt gtttgtttgt ttttgagatg gagtcttgct ctgtcacccg gctggagtg    240
cagtggtgcg atctcggctc actgcaagct ccacctccca ggttcaagtg attctgctgc    300
ctcggcctcc caagtagctg ggactacagg cgcccacctc cacgtctggc taattttgt    360
attttagta gagacggggt ttcaccatat tggccaggct ggtctcgaac tcctgacctt    420
gtgatccact cacctcggtc tcccaaagtg ctgggattat aggcgtgagc cactgcgcct    480
ggccggaaga actggttttt aggagatggt gactggggac tgtgagggag ctgagcatgg    540
cttgatagaa atcctgttag agagatgatt ataatgttca aaatcatgtg tgtctgagtg    600
```

<210> SEQ ID NO 25
<211> LENGTH: 660
<212> TYPE: DNA
<213> ORGANISM: Homo sapiens

<400> SEQUENCE: 25

```
agccccttg gtgcttctgc cccatgccct accctgctga gtagccctga ctctgcaggg     60
attggggtga ccctgttcat tgccctgtat gactatgagg ctcgaactga ggatgacctc    120
accttcacca agggcgagaa gttccacatc ctgaacaata cgtaagtgac caggccacct    180
agtcagaaca ttgcctgggc tgggagcagg acacagacag gaatcccacc tggtccctag    240
cctcagaatg ctccagccta gttgggaaca catatacata acaataaaaa ccctgggtga    300
ctgcaactgt gtgctggttg agggggggtgg tgttgggcca ctgcacccgg cctggaggag    360
atgatttta agctgaggct ataaaaatga aatagacggc cgggtgcagt ggctcatgcc    420
tgtaatccca gcactttggg aggccaaggc gggtggatca cctgaggtca ggagttcgag    480
accagcctgg ccaacatggt gaaaccctgt ctctattaaa aatacaaaaa ttagcagggc    540
atggtggcgc atgcctgtaa tcccagctac ttgagaggct gaggcagaag aatcacttga    600
acccgggagg cagaggttgc agtgagctga gattgcacca ctgcactcca gcctaggcaa    660
```

<210> SEQ ID NO 26
<211> LENGTH: 1500
<212> TYPE: DNA
<213> ORGANISM: Homo sapiens

<400> SEQUENCE: 26

```
gcccatgcta atccatgccc ctgaatcagc ccagaggaag ggacaccttt tcttaattgc     60
cactaaaact cctcagtttg tttgctgtgg cccttgcaga gggcacaacg ggctagggca    120
gaaatttggg actcatgaga gtaaagatga tcattaaggc tatataggag ggggctgggg    180
gcggtgacac atgcatgtaa tcccagcact ttgggaggcc gaggcgggcg gatcacatga    240
ggtcaggagt tcaagaccag cctggccaat gtggtgaaac cttatctcta ctaaaaatac    300
```

| | |
|---|---|
| aaaaattagc cgggtgtagt ggcaggcacc tgtagttcca gctactcaga aggctgaggc | 360 |
| aagagaatca cttgaacctg ggaggtggag gttgcagtga gctgagatcg agccactgca | 420 |
| ctccagcctg ggtgacagag caagactccg tctcaaaaaa aattaattaa ttaaaaattt | 480 |
| ttaaaaaagc tatatagacg gttaaggaag agagtggaga gtgcaaaagg ttggccctag | 540 |
| gaccccactt tggggaaagc tgccctcgaa ggagaaggag ccattggaga agagaggaaa | 600 |
| tccagaccag gccaagtcag aacaaccgag agagcggaga agcttcagga aacaagagag | 660 |
| ggcgtgtcag aggctaccgc tggatttggc agtggggtg accttggtga gagatttctc | 720 |
| tgtgtgaggg tgggaggcgg aggccagaca gcagagcctg ggaggagtg ggaggtgagg | 780 |
| aagtggagac ccaagtgtga agcactttt caagtgaagg gaaggcgaga agatacagca | 840 |
| gaatgttgac ggcaagatgg aacttagaat agtttccttt ggggaaggga gaaatgtggg | 900 |
| catgttgga ggttgttgga atagagaggc tgcatgcagg tggaggctgc tggcaggaag | 960 |
| tgggtatcac tgagcaggag cgggtaggcg aggttcagag gtcaagtgcg gtgaggccca | 1020 |
| agtctgggga ggtggtagga ggcgtgaaga agaggacgga caattatgca gaggacagga | 1080 |
| ggtttgtggg gagcttcatg cttgtgtcca catcttggag ccagtgtcac caagcactga | 1140 |
| gaggtgctca gtgcagtgtt gtggttacgg gtagtgtggt taggagcaca ggccctaaag | 1200 |
| cagacagcct gggttcctgt tctagcaact gctgccctga ctgtctaatg gggtttaaca | 1260 |
| atagtagcta tctcacaaca ttgttaggag aattaagtga atacatacgt gtattaaggc | 1320 |
| agaccctaac acgaaatatg tgtgttatta ttatagtgat tattaaggag gtagctaatg | 1380 |
| tcatgcgtgt gggagcgggg agggctttga aaaaacttga caatgtgtcc tgtctataca | 1440 |
| gtccctcaac acttcctccg tcccctcct gcctgccctc ctggacacac cacttgccaa | 1500 |

<210> SEQ ID NO 27
<211> LENGTH: 780
<212> TYPE: DNA
<213> ORGANISM: Homo sapiens

<400> SEQUENCE: 27

| | |
|---|---|
| ccctcccagc caggatgtga agcaggtgta ccagccccat tttacacatg gggaaaatgg | 60 |
| agtcttggct tgtgaggtga ctgtgcagga ggctgaggtg aggtttgagc agagcgtacc | 120 |
| tgactcttgc ctgcctttcc caacaggtgg tactttggaa agattgggag aaaggatgca | 180 |
| gagaggcagc tgctttcacc aggcaacccc caggggggcct ttctcattcg ggaaagcgag | 240 |
| accaccaaag gtaggggtgg tgccacgccc caaggcgact gggaggccca gccattgggg | 300 |
| tagggctagg agcggtaggc tgcttgggtt aaggccaaga ctgggaccag gtcctaggga | 360 |
| tgctgctgtc gggcctctcc cagctcccag actaggcag aggagaacag cagatcaaaa | 420 |
| gtgatcctct ccacaggtgc ctactccctg tccatccggg actgggatca gaccagaggc | 480 |
| gatcatgtga agcattacaa gatccgcaaa ctggacatgg gcggctacta catcaccaca | 540 |
| cgggttcagt tcaactcggt gcaggagctg gtgcagcact acatgggtga gggcagggc | 600 |
| ctcagatccc tgaaccaacc aactgaagca ttgtccagat gggggaactg aggcccagag | 660 |
| aagggaaggg actaccaagc agtattggcc agacggaaac cagaacccaa ggatggggtc | 720 |
| tgccagccca ggatccagct ctgtgagctt ctggaggaaa gcagtccttc accaagcagc | 780 |

<210> SEQ ID NO 28
<211> LENGTH: 3300
<212> TYPE: DNA
<213> ORGANISM: Homo sapiens

<400> SEQUENCE: 28

```
aactgatctt agggtctggc accaggctgg gataggataa ggagtggagg ggggtgtcct    60
ggcccacctg tgactctact tcatgacccc tccctagag gtgaatgacg ggctgtgcaa    120
cctgctcatc gcgccctgca ccatcatgaa gccgcagacg ctgggcctgg ccaaggacgc    180
ctgggagatc agccgcagct ccatcacgct ggagcgccgg ctgggcaccg gctgcttcgg    240
ggatgtgtgg ctgggtacgg agctcccggg ggccgggacg agggcctggg ctcggggag    300
agggtcctga caagacagcc tccgagcagg cacgtggaac ggcagcacta aggtggcggt    360
gaagacgctg aagccgggca ccatgtcccc gaaggccttc ctggaggagg cgcaggtcat    420
gaagctgctg cggcacgaca agctggtgca gctgtacgcc gtggtgtcgg aggagcccat    480
ctacatcgtg accgagttca tgtgtcacgg tcaggaggcg gagcctggtc gggcgggatt    540
cggggtgaag ttaagagggg agttttcagg cgtgggacct gggacgcgat ctgtgaggga    600
caagggacaa tggcagagt cccactaagg accaggtgt gtaaaacgac tggagggctg    660
aggtgggagc cgggccgagt gagaccacta gggagctggg gagggggcg gtgcctccgg    720
tgttaggcgg gtagggcttg ggctaacgaa ggcagaatcg ggaatgaggg agggtctggg    780
gcggagtctg ggtgggtcgt gtccggaaca ccaaggaaca gaagaaacga gatgtgggca    840
gagtccgtgt ctggcagcag ggccaggacg agacaagtga ggggttgagg cacccgcggg    900
gtcctaagtg aggggcgggt ccaggtggga ggggctgagg ggcggggtca gcgagagga    960
ggaggggctg ggcccggg tagggctttg ccgctgactt tctggcttct tcccaggcag    1020
cttgctggat tttctcaaga acccagaggg ccaggatttg aggctgcccc aattggtgga    1080
catggcagcc caggtaactg ggccagcagc ctttacctcc cggacctccc acctattaac    1140
tgttcacaaa ttctctgtcc cttcaaacgc ctgggagggc ggccccgccc cctgcatcag    1200
ctgtgcctcc agctgtgcct gagaggtact gcctctcttt ctgggcctca gtctccccct    1260
ctggaaagtg ggttttttcaa atggtccctc accctcaaa caggccacgg tgttgtgagt    1320
ccacatgagc tcccatctct ccacactatg gtccccagg tagctgaggg catggcctac    1380
atggaacgca tgaactacat tcaccgcgac ctgagggcag ccaacatcct ggttggggag    1440
cggctggcgt gcaagatcgc agactttggc ttggcgcgtc tcatcaagga cgatgagtac    1500
aacccctgcc aaggtgccct gcttcacccc accttccaag agctccccat gcaacaaggg    1560
acttccatgg ggccccacgc actcaggaac ccttcctcac tccaggtcgc ccgagtcgcc    1620
ccatcctgat gtagtatgag aggcaattct gggctcaaat cccaggtcgg ccacttacca    1680
gccatgtggc cttgggcaag tcacctaacc tctgggagct gccgtttctc ttctgtaaag    1740
tgacaatatt cagataacag gaagtcagca gatgtttacc aggcacctgc tatgtgacag    1800
gcacagctat aattcttgaa tgaaagacaa tggcgtgtaa cagtgggaat tctgtagcca    1860
gaatgcctga gtatgaatcc cagccaggta ttaactctgt gatctgggca agttacctaa    1920
ctactcagtg tctccgtttc ctcgtctgta aaatgagtct ctatctcatg ggggttttgg    1980
gagggttaaa tgagttaatg catgcatatc acttaaaaca gtgtctggca cacaggaaag    2040
gctagccaag tattggccgt tattaggata agaattattg cgattttggg aaagtgccca    2100
tcactatact agacacatag taggtgttga ctagatacca tgtcctttct actatgccca    2160
gagacccttg tgctcaggat ccccgaaatc ctcatcccta gagtccccat tctctctctg    2220
tctcttttt tttttttttt ttttttttga gatggagtct cactgtcacc caggctgaag    2280
```

| | |
|---|---|
| tgcagtggtg cgatctcagg ttattgaagc ctcccaggtt caagcaattc tcctgccgca | 2340 |
| gcctccctag tagctgggat tacaggcacc cgccaccatg cccggctaat ttttgtattt | 2400 |
| ttagtagaga cagggtttcg ccatgttggc caggctggtc tcaaactcct gacctcaagt | 2460 |
| gatccgcctg ccttggcctc ccaaagtgct gggattacag acgtgagcca ctgcgcccag | 2520 |
| accccattct cttaatccag ctgtttccag ggaccccctc actaactttc cctgctcccc | 2580 |
| catcttctcc aggttccaag ttccccatca agtggacagc cccagaagct gccctctttg | 2640 |
| gcagattcac catcaagtca gacgtgtggt cctttgggat cctgctcact gagctcatca | 2700 |
| ccaagggccg aatcccctac ccaggtttgc ctcgccaggg gtagggctgg ggtgggggat | 2760 |
| ggtcacgggg aagggcttcc acctggctgt ccctttgact gacagagacc catccttcag | 2820 |
| gcatgaataa acgggaagtg ttggaacagg tggagcaggg ctaccacatg ccgtgccctc | 2880 |
| caggctgccc agcatccctg tacgaggcca tggaacagac ctggcgtctg gacccggagg | 2940 |
| agaggcctac cttcgagtac ctgcagtcct tcctggagga ctacttcacc tccgctgaac | 3000 |
| cacagtacca gcccggggat cagacatagc ctgtccgggc atcaaccctc tctggcggtg | 3060 |
| gccaccagtc cttgccaatc ccagagctg ttcttccaaa gccccaggc tggcttagaa | 3120 |
| ccccatagag tcctagcatc accgaggacg tggctgctct gacaccacct agggcaacct | 3180 |
| acttgtttta cagatggggc aaaaggaggc ccagagctga tctctcatcc gctctggccc | 3240 |
| caagcactat ttcttccttt tccacttagg cccctacatg cctgtagcct ttctcactcc | 3300 |

<210> SEQ ID NO 29
<211> LENGTH: 382
<212> TYPE: DNA
<213> ORGANISM: Homo sapiens

<400> SEQUENCE: 29

| | |
|---|---|
| gccctgagct gcttcttcac acactggtat ttgtatctgt ggtaaaccca gtgacacggg | 60 |
| ggagatgaca tacaaaaagg gcaggacctg agaaagatta agctgcaggc tccctgccca | 120 |
| taaaacaggg tgtgaaaggc atctcagcgg ctgccccacc atggctacct gggccctcct | 180 |
| gctccttgca gccatgctcc tgggcaaccc aggtaaggcc ttcccctcgg gatcgatcct | 240 |
| gatggcccac ccagcctcgc actctcaggc tggctgaacc tggagcttgg actctgtggg | 300 |
| cacccaggtg ccctgcctc ccccggcct tctccccgt catggaggcc tggcctcccc | 360 |
| tcagagccag gcttagtcca gt | 382 |

<210> SEQ ID NO 30
<211> LENGTH: 900
<212> TYPE: DNA
<213> ORGANISM: Homo sapiens

<400> SEQUENCE: 30

| | |
|---|---|
| tggtgtgtgc ctgtaatccc agctactcag gaggctgagg caggagaatt gcttgaagcc | 60 |
| gggagacaga ggtggcagtg agccgagatc acgccactgc actccagcct gggcgacaga | 120 |
| gtgaggatcc atctcaaaaa aaaaaaaaag gaatttcttt gtgatttacg atgttgagca | 180 |
| ggttttcaaa tgttttggtc attcttatct tcctttgcga attacctgtt caaatatttt | 240 |
| gcccatttaa aaaattggat tgctttatta ttattattgc agtagcagtt gatataataa | 300 |
| ggagtccgta aacagaccca cagtcaattg atattcaacc aacgtgccaa agcaattcaa | 360 |
| tgggaaaaga aaaatctttt caagaaattg atatgaagaa acaaaacctc aacccagctc | 420 |
| acactataca ttaatttgag atgagtcata gacctaaatg tcaaagttaa aattataaaa | 480 |

```
gttctagaaa aaaacataga ggtgattttt atgatagcgt aagtgaagat ttcctgaaga      540
agatacagca ggcaatattt cttttctttt cttttttttg agacggagtc tcgctctgtc      600
gccaggctgg agtgcagtgg cgcgatctcg gctcactgca agctccgcag aaggcaatat      660
ttcacagagg aattctttgt gggcctgggc ctgacttgca atgggccagt tcctggggta      720
ccatgggtgg gaattgggta aaacttaccc caggttctta tcacacggga ccccagaggc      780
ctgggtggag gcttgtgact aactacatga gctttgccac gtactcctca atacctctga      840
caaggactta ctgcagtgtt tggtctcacc aagtttccca cataaagag acatgagtca       900
```

<210> SEQ ID NO 31
<211> LENGTH: 1440
<212> TYPE: DNA
<213> ORGANISM: Homo sapiens

<400> SEQUENCE: 31

```
ttgtaatcat ataggtacaa agtcctacca attcttcctg aaatatgttt ccttatcaaa       60
aagtcctgca aagccgtgcg tggttgctca tgcctataat cccagcactt tggaggctgg      120
gaggatcgct tgagtccagg agttcgagac cagcctggac aacatatgga gacccatctc      180
taccaaaaat tttaaaatca gcaggggtgg tagtggcaag cacctgtggt ctcatctact      240
tgggaggctg aggtgggggg attgttggag cctgggcggt tgaggctgca gtgatctgtg      300
attgcaccac tgcactctag cctgaggtac agagcaagaa cttgtatcag aaaaaaaaaa      360
aaaaagtcct gcggtagctg acactgccat tgcctatacg attcccattc cctcatcctc      420
cctagcagga tatcaatttt gttcgaagtg tcaatgaagg ccaggtgcgg tggctgatgc      480
ctgtaatcct aacactttgg gaggccgagg caggcggatc acctgaggtc aggagttcaa      540
gaccagcctg ccaacatggt gaaaccctg tctctactaa aaacacacaa attagcaggg       600
catggtggcg tgcacctgta atcccagcta ctcaggaggc tgagacagga gaatcacttg      660
aacccggagg tggaggttgc aatcagccaa gatcacacca ctgcacttca gcttgggtga      720
caagagtgaa actctgtctc aaaaagaaa aacaaaacaa aaacaaacaa caacaacaaa      780
aagcaaagtg tcagtgaagg tccagcaaaa gactcccttc ctattgccct ttgcagccag      840
ggtcatcatg tgacacagtt cagatcaatg agatggaggc tgagggtccc tgggaaagat      900 gttttttccta tacaggtacc acctctttca gcttcactct ttccattttc cacgtgaaca      960
ggccttgtag cctggaggag ctacagctgc cttttgaga tgctgaggca ccctgtctga     1020
agaaggccct cacatcactc aacttgacta ctgggtgagc ccttggagag gcttccagc      1080 ctctgctctt caagccgaag taccacaggg gacacgagtc ccagagttac aggaccccag     1140
ctatggttca tgtgtaaagg gaaccattag gcaaccaggg gaaatgatga agaagatcta     1200
catttacaaa tgtggaaaga tgttcgtggt atattgttaa attaaaaagc tgtttaaaaa     1260 tagttttttgg gtcaagtgag atgactcact tatacttta gtataagtat gtcccatgca     1320
atatctggaa cgtacttgta ctaaggggtt tctccctcca tcggcacatc ccaggcatcc     1380
tggcagctgc tggcctccag caaccccaca ttctagttgt gtgggagtgg ggtgtggcat     1440
```

<210> SEQ ID NO 32
<211> LENGTH: 1680
<212> TYPE: DNA
<213> ORGANISM: Homo sapiens

<400> SEQUENCE: 32

| | | | | | |
|---|---|---|---|---|---|
| ctggcctggc | caaggaggag | agacaggcca | gggattctgg | tcctaactct | actggccaca | 60 |
| ctgtgtggcc | tgagaccccc | ctttccctcc | caagcccctg | cctccgcatc | tgcgtggtga | 120 |
| aggccattgg | ccctcatcgg | tggatctgcg | tttcctcggg | cctacactgt | ctaggattgt | 180 |
| gcggggctgg | tgagagaaca | agatctcttc | tgtgttcaag | gcagacttcc | tgccccctgc | 240 |
| accctgctct | ctcccaggcc | ttgaggtcag | tgtgagcccc | aagggcaaga | acacttctgg | 300 |
| aagggagagt | ggatttggct | gggccatctg | gatggaaggt | aaaaaagaa | aatcccttga | 360 |
| aaggagattg | agggaagttt | ctagacaaac | cgacccccaa | atctgtgttg | ctgggggaac | 420 |
| agaggagaag | agagagtctc | gccctcctgg | ctttctagaa | ggaacgtgag | aacacgtgtt | 480 |
| tgtgctgaga | gtgggtcaga | gcggctccag | ggcaaagcat | gtggacaggt | atcctggccc | 540 |
| cctgcaaggc | ccagctcctg | tcctaggccc | tggtcacctc | ctggactccc | accagccagg | 600 |
| agaacgggct | ttccctctcc | ttccgcctgc | ggaggggaag | ctgaagtctg | gtcttcctca | 660 |
| ggtctggtct | tctctcgtct | gagccctgag | tactacgacc | tggcaagagc | ccacctgcgt | 720 |
| gatgaggaga | atcctgcccc | gtgcctggcc | caggagggcc | cccaggtacg | tgttggctct | 780 |
| ctgctcacct | gccacagtcc | ctctcctttc | cctcctccct | ggtggctcct | ggggtgaggt | 840 |
| ctggagctct | ctaatggtca | ggaggtggga | gtggaggctg | ggctgtttct | gacgatgctg | 900 |
| gttttgttga | attcatgtct | ggccaggagg | gctacaggta | tctggcagac | tcctccagga | 960 |
| ggatcctctg | gggtctcacc | ctccaaggag | cctggggctg | cagaacccaa | ataggcagac | 1020 |
| tcccctggga | gttcctcaat | aggagagggg | caagtgcagg | gctgggaaag | tactgggggt | 1080 |
| gtgggaggct | gtttctgggg | tgtctcagag | cctctaagac | aagcaaaagg | gtgggcaggg | 1140 |
| gccaggcagc | cagttcaggc | cttcagtgta | tccacgctct | gggaagagat | cacggacatt | 1200 |
| cctgccggcc | tcagaaacac | aaagggcccc | tttcctgggc | actttcacgc | gctcccagag | 1260 |
| tgtctgagag | accatcataa | gggctttctt | tcctgacagg | gtgacctgtt | gaccaaaaca | 1320 |
| caggagctgg | gccgtgacta | caggacctgt | ctgacgatag | tccaaaaact | gaagaagatg | 1380 |
| gtggataagc | ccacccaggt | gaggccaagg | ggctacagag | cctcctgtct | gctgctcaat | 1440 |
| ggaggggcca | gcctgtgacc | aggtcgggga | tcggggagcc | cggggcacc | ttgcacagtg | 1500 |
| atcctggggg | agggcttcct | agaagggaat | ctgtgagtcc | ccgtgtgtct | gtggatgaat | 1560 |
| ttcagagaac | ttgtgaaatt | gtgactctct | ggaactgtgt | aagtcagacg | gcagagtata | 1620 |
| catggttttc | atcatgtatc | ctcaaagagg | gcttgtccca | gagaagttag | gaatcttccc | 1680 |

<210> SEQ ID NO 33
<211> LENGTH: 540
<212> TYPE: DNA
<213> ORGANISM: Homo sapiens

<400> SEQUENCE: 33

| | | | | | |
|---|---|---|---|---|---|
| gagccctacc | tggccagtct | tgggccaggc | cttggggact | gggagtaggg | gctgagcccc | 60 |
| gtctgtacag | tctctggccc | catgggcacc | aggtgccagc | tcctcgcacc | cagtactccc | 120 |
| attgctaggg | ctgctggaac | ctgcagggtg | gcagagctgg | gcaggactca | ccctataacc | 180 |
| atgtccactg | tggtgctgct | gctgcagaga | agtgtttcca | atgctgcgac | ccgggtgtgt | 240 |
| aggacgggga | ggtcacgatg | gcgcgacgtc | tgcagaaatt | tcatgaggag | gtatcagtct | 300 |
| agagttaccc | agggcctcgt | ggccggagaa | actgcccagc | agatctgtga | ggacctcagg | 360 |
| ttgtgtatac | cttctacagg | tgagtgcaga | ggtgacagca | gggatacctc | ctgagggttg | 420 |
| gagacagctt | cccccaggat | atatcaaagc | tgcctcctta | ctcccccatc | tcccagcttg | 480 |

```
ggaaagtgtg gagaattgag cagatggact ttagctagaa atgtttgaga aatactgatt    540
```

<210> SEQ ID NO 34
<211> LENGTH: 660
<212> TYPE: DNA
<213> ORGANISM: Homo sapiens

<400> SEQUENCE: 34

```
tgtggctttt ctattcaagg ccccacaacc tgctcaggct gccgactggc ttccaggatg     60
tgcctctggg tgtgttcagt agggtcaggt ggctctggga ccttaagcaa gtaacattct    120
gagtgcctgc ttctccttga ggacccacca catctgccca cagctggctg ttctctcctc    180
tccaggtccc ctctgagccc tctcaccttg tcctgtggaa gaagcacagg ctcctgtcct    240
cagatcccgg gaacctcagc aacctctgcc ggctcctcgc ttcctcgatc cagaatccac    300
tctccagtct ccctcccctg actccctctg ctgtcctccc ctctcacgag aataaagtgt    360
caagcaagat tttagccgca gctgcttctt ctttggtgga tttgaggggt gggtgtcagt    420
ggcatgctgg ggtgagctgt gtagtccttc aataaatgtc tgtcgtgtgt cccatacact    480
gttgtagatg ttatggattt agtggtgaac gagacaacct taacagcatt cacacagtta    540
gtcgtgaaat gcttactgag cactcaccac agccatgcgt tattcagaaa ggccaaggca    600
cacagtggcg atgtcccag aagctctcag accagtggga tagaccagca gggttagagg    660
```

<210> SEQ ID NO 35
<211> LENGTH: 469
<212> TYPE: DNA
<213> ORGANISM: Homo sapiens

<400> SEQUENCE: 35

```
tgaggctgtg ggtcccaccc actcagctca ctcgggcctc tggccaacag ggcatgggga     60
catcatatca ggtaagggga atgggtgtcc tacagagggg ttgccagcgg ggatgggtgc    120
tcagtggtct tctcccgatc aggctacatc cacgtgacgc agaccttcag cattatggct    180
gttctgtggg ccctggtgtc cgtgagcttc ctggtcctgt cctgcttccc ctcactgttc    240
cccccaggcc acggcccgct tgtctcaacc accgcagcct tgctgcagg taaggactct    300
ggactggact ggggcatcgc gagccagcga attcctgccg aggagctgag ccatctctct    360
tgtccttgtc cccagccatc tccatggtgg tggccatggc ggtgtacacc agcgagcggt    420
gggaccagcc tccacacccc cagatccaga ccttcttctc ctggtcctt              469
```

<210> SEQ ID NO 36
<211> LENGTH: 660
<212> TYPE: DNA
<213> ORGANISM: Homo sapiens

<400> SEQUENCE: 36

```
caatctcaca tatccaaaaa taagttcctg atctcacaca cagcctatgt gttcctccca     60
tggtcttccc catcttagga aatggcaacc ccatttttta ttttacttat ttgttttttt    120
gagatggagt ctcgccctgt tgcccaggct ggagtgcagt ggtgcaatct cggctcactg    180
caacctccgc ctccctcct gggttcaagt gattctcctg cctcagcctc caagtagct    240
gggattacag gcgtctgcca ccacgcccag ctaattttg tatttttagt ggagacgggg    300
tttcaccatg ttggccaggc tagtctcaaa ctcctgacct cgtgatccgc ccgcctcggc    360
ctcccaaagt gctgggatta caggtgtgag ccaccacgcc cggccaaaca acccccatttt   420
```

```
tatccagcta ctcaagccaa caactttggg attcaatgtt ggcttttttt tttttttttt    480 tttttttgaga cagggtctca ctcttgccca ggctacaatg cagtggcgtg atcacagctc   540
actgcagcct ccacctccca ggctcaactg agcctcccac ctcagcctcc tgagcagcta   600
agactacagg catgcaccac ccactatgcc tgggtaattt tttaatttttt tgtagagatg   660
```

<210> SEQ ID NO 37
<211> LENGTH: 1080
<212> TYPE: DNA
<213> ORGANISM: Homo sapiens

<400> SEQUENCE: 37

```
tgatgccttc cataataact gtttaccatt agcattcatt tctttaatag aacgtaggtt    60
aattgaggat tagtcttttt aaattttatt ttattttatt tttttgaga tggagtctca   120 ctctgtcacc caggctggag tacggtggtg cgatcttggc tcactgcaac ttctgactcc   180
cgggttcaag cgattctcct gcctcagcct cccgagtagc tggaattaca ggtgcacgcc   240
accactccca gctaattttt tggggtcttc cgtggcagat gggggctact gaggagcttt   300
caagcccggg agaggttgga aggggctgga gaaagttgga agagacctgg gtgattcaaa   360
aaaactgaca gtgcttagac aagactgaca gagacctaag agaaccaagt ggccaagcag   420
gcgacgtgag ctgtgaaccc cgaaaatctg agacaggtct cagttaattt agaaagttta   480
ttttgccatg tagtcacagc tactcaggag gctgaggcag gagaatggcg tgaacccggg   540
aggcggagct tgcagtgagc cgagatcgtg ccactgcact ccagcctggg caacagagcg   600
agattccatc tcaaaaaaaa gaacaataga agtttatttt tgccaaagtt gaggacatgc   660
gcccgtgaca cagcctcagg atgtcctgac gacatgtgcc caaggtggtc ggggcacagc   720
ttggttctat acatttaggg gagacatgac atatcaatca atagatgtaa gaagtacatt   780
ggtgcatcca ggaaggtggg gacaactcaa agcagggagg gggattccac gttacaggta   840
ggtgagagaa aaattgttgc attctttgag tttcttttttt cctagatgga gtctaactct   900
gttgcccagg ctagagtgca gtggcacaat ctcggcttac tgcaacctcc acctcctggg   960
ttcaagtgat tctcctacct cagtctcctg agtctgagac tacaggcgtg caccaccatg  1020
cccggctaat ttttgtattt ttagtagaga tggggtttca ccatgttggc caggctggtt  1080
```

<210> SEQ ID NO 38
<211> LENGTH: 840
<212> TYPE: DNA
<213> ORGANISM: Homo sapiens

<400> SEQUENCE: 38

```
agagctctca ggaaaagctt cagaaggagg cctggggttt tcctctggca accacagacc    60
acatctggtt gagaaagctg ctggagatcc tgcgagcaat tctgtcttca aggccccagc   120
tgccttgcct ttgtgctctt aagagatggt cttggctggc tgggtgcggt cactcacgcc   180
tgtaattcca gcactttggg aggctgaagc aggtggatca cctgaggtca ggagttcgag   240
accagcctga ccaacgtgga gaaaccccgt ctctactaaa aatagaaagt cagccgggca   300
tggtggcgca tgcctgtaat cctagttact taggaggctg aggcaggagg atctcttgaa   360
cctgggaggc agaggttgct gtgagcccccg atcatgccat tgcactccag cctgagcaac   420
aaaagtgaaa ctgcgtctca aaaaaaaaaa aaaaaaaaa aaaaaagat gaccttcact   480 cacccgctct tactggcttg tggtgtctgt cagagggcct gggcctgtga tcagcctgtg   540 ataccctacat gtgcagagac tcactggagc caggtacagg tcacctctgt gtatgcatgc   600
```

```
atgcatgggt gtgatggtgg tggtagtggg acccacttgg ggagatgaga aatgaggtta    660
caggcttgga cctggaggtg aaaggagaat gaaaatggtc ggagttaggt atgaattata    720
gaggttgcag agaagaatga aaagacagtg gctgggcgca gtggctcact cctgtaatct    780
cagcactgtg ggaggctgag gcaggtggat cacctgaggt caggagttca agaccagcct    840

<210> SEQ ID NO 39
<211> LENGTH: 1020
<212> TYPE: DNA
<213> ORGANISM: Homo sapiens

<400> SEQUENCE: 39
tctccaagac agaggtcctc ttccagacta ctccctatgt attagtctat tctcacactg     60
ctataaataa ctgcctggcc gggcgtggtg gctcacacct gtaatcccaa cactttggga    120
ggccaaggtg ggcagatcac ctgaggtcag gagttaaaga ccagcctgtc aacatggtg    180 aaaacccgaa aatctactaa acctgaaatc tactaaaaat acaaaaatta gctgggtgtg    240
gtggcgggca cctgtaatcc cagctacttg ggaggctgaa gcaggagaac tgcttgaacc    300
tgggaggtgg agattgcagt gagccgagat tttgccactg ccctccagcc tgagtgacaa    360
gagtgagact ctgtctcaaa caacaacaac aacaacaaca aatgcctgag actgggtaat    420
ttataaagga aagaggttta tttgattcac agttcagcat ggctggggag gcctcaggaa    480
acttacaatc atggtggaag gtgaagggga agcaagccac tgtcttcaca gagtggcagg    540
aagaaggcca agcgaaggca ggaagagccc cttaaaaaaa caccatatct tgtgaaaact    600
cactcactat cacaagaaca gcatggggga agccggcccc atgattcaat acctccacc    660 tggtctctac ctagacacgt gaggattatg gggacacaat tcaaggtgcg atttgggtag    720
ggacacaaac cctaaccata tcaccgtttc acagaggtca agttttcctg ggccttctac    780
ctgggctgtg gtaccgtcac cttatacctg ctcgtagatg aggtgttgcc aggacctgat    840
ggtgtggatg gaagaggcta gcgtttgggg ggctggagaa ccctaaacca aaatccttat    900
gtcccccaac accccctagg ccccccgatc ctggtgataa aggccaccag gctggagccc    960
ccacccaagc agggatgcca ctgaactcat taatcagatg aggatgtggg tatgtctgac   1020

<210> SEQ ID NO 40
<211> LENGTH: 660
<212> TYPE: DNA
<213> ORGANISM: Homo sapiens

<400> SEQUENCE: 40
tacaccctag cctgattggc ttcctcccac ctcagggccc ccaagcctct ctctctcacc     60
tcttccagga agccccgact tggtgttgaa ggttccatgg gtgggagttg tagaatctgt    120
gacagaggca agtactaaac caccgcccaa accactgatg atctgacacc ctcagtgccc    180
tcccccatca cacactaagc ggggaactgg accccaggga ggggagggag gacgttgcct    240
gtgcaatcca ggaagggagg gtatgtgaaa agctaccggg aactgtgtga aaccaaacca    300
gcctcatgtg acaaagcgca ggaccccctca ctgccccaac tgcttgctgt tctctctttc    360
ttgggctcta aggacccagg agtctgggtg cacagcctcc ttctctctga gattcaagag    420
tctgatcagc agcctcttcc tcctccagga cccagaagcc ctgagcttat cccatggag    480 ctctgccggt ccctggccct gctgggggc tccctgggcc tgatgttctg cctgattgct    540
ttgagcaccg atttctggtt tgaggctgtg ggtcccaccc actcagctca ctcgggcctc    600
```

```
tggccaacag ggcatgggga catcatatca ggtaagggga atgggtgtcc tacagagggg    660
```

<210> SEQ ID NO 41
<211> LENGTH: 540
<212> TYPE: DNA
<213> ORGANISM: Homo sapiens

<400> SEQUENCE: 41

```
ggggcaagtg cttaaactct ttctggctcc ccaggtgccc tgagcctggg tgctcactgt     60
ggcggtcccc gtcctggcta tgaaaccttg tgagcagaag gcaagagcgg caagatgagt    120
tttgagcgtt gtattccaaa ggcctcatct ggagcctcgg gaaagtctgg tcccacatct    180
gcccgccctt ccagcccttc cccagcccct cctcttgttt cttcattcat tcaacaaaat    240
ttggctggaa tctggttatt ttgagattaa ttctgccaag acataagcca actgtctgcc    300
agctccatgg taggagctgg gcaccaaggg aaggtgaggg cccaccaggc cgaccagcct    360
gcagggcgct cctgcccagt acgagtgccc ggcccgtgtg gacacaggct ccaacccgtg    420
tctatgtctc cccttctcca gcactttttct tcctccctgt gtctttctcc ctttagctgg    480
ctctctttcc ttctctctcc ctctctgatt ttgtcccccct tgccagaact cagcccttcc    540
```

<210> SEQ ID NO 42
<211> LENGTH: 22
<212> TYPE: DNA
<213> ORGANISM: Unknown
<220> FEATURE:
<223> OTHER INFORMATION: Primer 1455p

<400> SEQUENCE: 42

```
aaggattagg agaagaaggt tt                                              22
```

<210> SEQ ID NO 43
<211> LENGTH: 22
<212> TYPE: DNA
<213> ORGANISM: Unknown
<220> FEATURE:
<223> OTHER INFORMATION: Primer 1455o

<400> SEQUENCE: 43

```
taaaactata aatcccaccc ac                                              22
```

<210> SEQ ID NO 44
<211> LENGTH: 22
<212> TYPE: DNA
<213> ORGANISM: Unknown
<220> FEATURE:
<223> OTHER INFORMATION: Primer 1452r

<400> SEQUENCE: 44

```
acacaactct tctcctcaaa at                                              22
```

<210> SEQ ID NO 45
<211> LENGTH: 22
<212> TYPE: DNA
<213> ORGANISM: Unknown
<220> FEATURE:
<223> OTHER INFORMATION: Primer 1452q

<400> SEQUENCE: 45

```
tagggggttag gtaggtaatg aa                                             22
```

<210> SEQ ID NO 46
<211> LENGTH: 22

```
<212> TYPE: DNA
<213> ORGANISM: Unknown
<220> FEATURE:
<223> OTHER INFORMATION: Primer 1454p

<400> SEQUENCE: 46
atgtgggtaa atgaggatgt ag                                              22

<210> SEQ ID NO 47
<211> LENGTH: 22
<212> TYPE: DNA
<213> ORGANISM: Unknown
<220> FEATURE:
<223> OTHER INFORMATION: Primer 1454o

<400> SEQUENCE: 47
ccaaccccaa aaatataaac at                                              22

<210> SEQ ID NO 48
<211> LENGTH: 23
<212> TYPE: DNA
<213> ORGANISM: Unknown
<220> FEATURE:
<223> OTHER INFORMATION: Primer 1458r

<400> SEQUENCE: 48
accctaaact acttcttcac aca                                             23

<210> SEQ ID NO 49
<211> LENGTH: 22
<212> TYPE: DNA
<213> ORGANISM: Unknown
<220> FEATURE:
<223> OTHER INFORMATION: Primer 1458q

<400> SEQUENCE: 49
attggattaa gtttggtttt ga                                              22

<210> SEQ ID NO 50
<211> LENGTH: 22
<212> TYPE: DNA
<213> ORGANISM: Unknown
<220> FEATURE:
<223> OTHER INFORMATION: Primer 1503r

<400> SEQUENCE: 50
ccccaaactt aaaattcaat ac                                              22

<210> SEQ ID NO 51
<211> LENGTH: 23
<212> TYPE: DNA
<213> ORGANISM: Unknown
<220> FEATURE:
<223> OTHER INFORMATION: Primer 1503q

<400> SEQUENCE: 51
ttaggagaga agttgttatt ggt                                             23

<210> SEQ ID NO 52
<211> LENGTH: 22
<212> TYPE: DNA
<213> ORGANISM: Unknown
<220> FEATURE:
<223> OTHER INFORMATION: Primer 1504p

<400> SEQUENCE: 52
```
aggtagggga ttaggaaagt ag                                       22

<210> SEQ ID NO 53
<211> LENGTH: 22
<212> TYPE: DNA
<213> ORGANISM: Unknown
<220> FEATURE:
<223> OTHER INFORMATION: Primer 1504o

<400> SEQUENCE: 53
aattccaacc aaataaaaac at                                       22

<210> SEQ ID NO 54
<211> LENGTH: 22
<212> TYPE: DNA
<213> ORGANISM: Unknown
<220> FEATURE:
<223> OTHER INFORMATION: Primer 1505p

<400> SEQUENCE: 54
atttaagtag tgaggatgga gg                                       22

<210> SEQ ID NO 55
<211> LENGTH: 22
<212> TYPE: DNA
<213> ORGANISM: Unknown
<220> FEATURE:
<223> OTHER INFORMATION: Primer 1505o

<400> SEQUENCE: 55
ccaataaacc aatctttcct aa                                       22

<210> SEQ ID NO 56
<211> LENGTH: 18
<212> TYPE: DNA
<213> ORGANISM: Unknown
<220> FEATURE:
<223> OTHER INFORMATION: Primer 1506p

<400> SEQUENCE: 56
tttagaaatg ggaagggg                                            18

<210> SEQ ID NO 57
<211> LENGTH: 24
<212> TYPE: DNA
<213> ORGANISM: Unknown
<220> FEATURE:
<223> OTHER INFORMATION: Primer 1506o

<400> SEQUENCE: 57
aaaaatcact aaacctacaa caaa                                     24

<210> SEQ ID NO 58
<211> LENGTH: 22
<212> TYPE: DNA
<213> ORGANISM: Unknown
<220> FEATURE:
<223> OTHER INFORMATION: Primer 1507r

<400> SEQUENCE: 58
aaacccttta caaaatcaaa aa                                       22

<210> SEQ ID NO 59
<211> LENGTH: 22
<212> TYPE: DNA
<213> ORGANISM: Unknown

```
<220> FEATURE:
<223> OTHER INFORMATION: Primer 1507q

<400> SEQUENCE: 59
ggatagtagt agggatgtgg aa                                          22

<210> SEQ ID NO 60
<211> LENGTH: 24
<212> TYPE: DNA
<213> ORGANISM: Unknown
<220> FEATURE:
<223> OTHER INFORMATION: Primer 1508p

<400> SEQUENCE: 60
tgttttgtaa attatggagt gagt                                        24

<210> SEQ ID NO 61
<211> LENGTH: 22
<212> TYPE: DNA
<213> ORGANISM: Unknown
<220> FEATURE:
<223> OTHER INFORMATION: Primer 1508o

<400> SEQUENCE: 61
aaaacctacc actatatcca cc                                          22

<210> SEQ ID NO 62
<211> LENGTH: 22
<212> TYPE: DNA
<213> ORGANISM: Unknown
<220> FEATURE:
<223> OTHER INFORMATION: Primer 1509r

<400> SEQUENCE: 62
tcactcatta cccaaactaa aa                                          22

<210> SEQ ID NO 63
<211> LENGTH: 22
<212> TYPE: DNA
<213> ORGANISM: Unknown
<220> FEATURE:
<223> OTHER INFORMATION: Primer 1509q

<400> SEQUENCE: 63
ttagaggaag tggtgtgtgt ag                                          22

<210> SEQ ID NO 64
<211> LENGTH: 19
<212> TYPE: DNA
<213> ORGANISM: Unknown
<220> FEATURE:
<223> OTHER INFORMATION: Primer 1510r

<400> SEQUENCE: 64
ccattctcct acctcaacc                                              19

<210> SEQ ID NO 65
<211> LENGTH: 26
<212> TYPE: DNA
<213> ORGANISM: Unknown
<220> FEATURE:
<223> OTHER INFORMATION: Primer 1510q

<400> SEQUENCE: 65
aaaaataaaa gttaaggggt ttatag                                      26
```

```
<210> SEQ ID NO 66
<211> LENGTH: 25
<212> TYPE: DNA
<213> ORGANISM: Unknown
<220> FEATURE:
<223> OTHER INFORMATION: Primer 1511r

<400> SEQUENCE: 66
cacaatccaa tcatactctt ttaat                                              25

<210> SEQ ID NO 67
<211> LENGTH: 22
<212> TYPE: DNA
<213> ORGANISM: Unknown
<220> FEATURE:
<223> OTHER INFORMATION: Primer 1511q

<400> SEQUENCE: 67
atgtaatgtg ggttaggtat gg                                                 22

<210> SEQ ID NO 68
<211> LENGTH: 22
<212> TYPE: DNA
<213> ORGANISM: Unknown
<220> FEATURE:
<223> OTHER INFORMATION: Primer 1512p

<400> SEQUENCE: 68
aattgggagg tagtagagtg gt                                                 22

<210> SEQ ID NO 69
<211> LENGTH: 22
<212> TYPE: DNA
<213> ORGANISM: Unknown
<220> FEATURE:
<223> OTHER INFORMATION: Primer 1512o

<400> SEQUENCE: 69
tcacccaaac aaaaatacta aa                                                 22

<210> SEQ ID NO 70
<211> LENGTH: 21
<212> TYPE: DNA
<213> ORGANISM: Unknown
<220> FEATURE:
<223> OTHER INFORMATION: Primer 1513p

<400> SEQUENCE: 70
ggaagggaag agagtttgtt a                                                  21

<210> SEQ ID NO 71
<211> LENGTH: 22
<212> TYPE: DNA
<213> ORGANISM: Unknown
<220> FEATURE:
<223> OTHER INFORMATION: Primer 1513o

<400> SEQUENCE: 71
accccttaat acctctccta aa                                                 22

<210> SEQ ID NO 72
<211> LENGTH: 22
<212> TYPE: DNA
<213> ORGANISM: Unknown
<220> FEATURE:
<223> OTHER INFORMATION: Primer 1514p
```

```
<400> SEQUENCE: 72
ttagtgttag aaagtggatg gg                                              22

<210> SEQ ID NO 73
<211> LENGTH: 22
<212> TYPE: DNA
<213> ORGANISM: Unknown
<220> FEATURE:
<223> OTHER INFORMATION: Primer 1514o

<400> SEQUENCE: 73
aatctataac cccttcaaaa cc                                              22

<210> SEQ ID NO 74
<211> LENGTH: 22
<212> TYPE: DNA
<213> ORGANISM: Unknown
<220> FEATURE:
<223> OTHER INFORMATION: Primer 1515p

<400> SEQUENCE: 74
ttttattttt aggttggggt aa                                              22

<210> SEQ ID NO 75
<211> LENGTH: 20
<212> TYPE: DNA
<213> ORGANISM: Unknown
<220> FEATURE:
<223> OTHER INFORMATION: Primer 1515o

<400> SEQUENCE: 75
actcttccat ccccttaaac                                                 20

<210> SEQ ID NO 76
<211> LENGTH: 22
<212> TYPE: DNA
<213> ORGANISM: Unknown
<220> FEATURE:
<223> OTHER INFORMATION: Primer 1516p

<400> SEQUENCE: 76
aggggaattt tgttgttttt at                                              22

<210> SEQ ID NO 77
<211> LENGTH: 23
<212> TYPE: DNA
<213> ORGANISM: Unknown
<220> FEATURE:
<223> OTHER INFORMATION: Primer 1516o

<400> SEQUENCE: 77 acaactttc ttccttactc aca                                              23

<210> SEQ ID NO 78
<211> LENGTH: 21
<212> TYPE: DNA
<213> ORGANISM: Unknown
<220> FEATURE:
<223> OTHER INFORMATION: Primer 1517p

<400> SEQUENCE: 78
gggtggaaaa tatggttttt a                                               21

<210> SEQ ID NO 79
```

```
<211> LENGTH: 22
<212> TYPE: DNA
<213> ORGANISM: Unknown
<220> FEATURE:
<223> OTHER INFORMATION: Primer 1517o

<400> SEQUENCE: 79
aataatcctc aaaactctcc aa                                               22

<210> SEQ ID NO 80
<211> LENGTH: 22
<212> TYPE: DNA
<213> ORGANISM: Unknown
<220> FEATURE:
<223> OTHER INFORMATION: Primer 1518r

<400> SEQUENCE: 80
ttacattact caaaacatcc ca                                               22

<210> SEQ ID NO 81
<211> LENGTH: 22
<212> TYPE: DNA
<213> ORGANISM: Unknown
<220> FEATURE:
<223> OTHER INFORMATION: Primer 1518q

<400> SEQUENCE: 81
ttatttgtga agtggggtta gt                                               22

<210> SEQ ID NO 82
<211> LENGTH: 20
<212> TYPE: DNA
<213> ORGANISM: Unknown
<220> FEATURE:
<223> OTHER INFORMATION: Primer 1519p

<400> SEQUENCE: 82
tttttggggt tgagaattta                                                  20

<210> SEQ ID NO 83
<211> LENGTH: 22
<212> TYPE: DNA
<213> ORGANISM: Unknown
<220> FEATURE:
<223> OTHER INFORMATION: Primer 1519o

<400> SEQUENCE: 83
tctacaaact acactcccct tc                                               22

<210> SEQ ID NO 84
<211> LENGTH: 23
<212> TYPE: DNA
<213> ORGANISM: Unknown
<220> FEATURE:
<223> OTHER INFORMATION: Primer 1520p

<400> SEQUENCE: 84
ggaatgttag gtttagaggt ttt                                              23

<210> SEQ ID NO 85
<211> LENGTH: 23
<212> TYPE: DNA
<213> ORGANISM: Unknown
<220> FEATURE:
<223> OTHER INFORMATION: Primer 1520o

<400> SEQUENCE: 85
```
caaactacaa taccctttc tca 23

<210> SEQ ID NO 86
<211> LENGTH: 22
<212> TYPE: DNA
<213> ORGANISM: Unknown
<220> FEATURE:
<223> OTHER INFORMATION: Primer 1521r

<400> SEQUENCE: 86
aaccttcacc ataaatcaat tc 22

<210> SEQ ID NO 87
<211> LENGTH: 23
<212> TYPE: DNA
<213> ORGANISM: Unknown
<220> FEATURE:
<223> OTHER INFORMATION: Primer 1521q

<400> SEQUENCE: 87
ggtgttgtta ttaaaatggt tgt 23

<210> SEQ ID NO 88
<211> LENGTH: 22
<212> TYPE: DNA
<213> ORGANISM: Unknown
<220> FEATURE:
<223> OTHER INFORMATION: Primer 1522p

<400> SEQUENCE: 88
aaaatgaatg ttttggtgat ta 22

<210> SEQ ID NO 89
<211> LENGTH: 23
<212> TYPE: DNA
<213> ORGANISM: Unknown
<220> FEATURE:
<223> OTHER INFORMATION: Primer 1522o

<400> SEQUENCE: 89
aacacttcca tacctactcc ttt 23

<210> SEQ ID NO 90
<211> LENGTH: 21
<212> TYPE: DNA
<213> ORGANISM: Unknown
<220> FEATURE:
<223> OTHER INFORMATION: Primer 1523p

<400> SEQUENCE: 90
aaaagtttag agttggttgg g 21

<210> SEQ ID NO 91
<211> LENGTH: 22
<212> TYPE: DNA
<213> ORGANISM: Unknown
<220> FEATURE:
<223> OTHER INFORMATION: Primer 1523o

<400> SEQUENCE: 91
cttcccactt accatcttat tt 22

<210> SEQ ID NO 92
<211> LENGTH: 22
<212> TYPE: DNA

```
<213> ORGANISM: Unknown
<220> FEATURE:
<223> OTHER INFORMATION: Primer 1524p

<400> SEQUENCE: 92
tttattgtta tggggaaaat tg                                              22

<210> SEQ ID NO 93
<211> LENGTH: 20
<212> TYPE: DNA
<213> ORGANISM: Unknown
<220> FEATURE:
<223> OTHER INFORMATION: Primer 1524o

<400> SEQUENCE: 93
aaaaattcct accacccact                                                 20

<210> SEQ ID NO 94
<211> LENGTH: 20
<212> TYPE: DNA
<213> ORGANISM: Unknown
<220> FEATURE:
<223> OTHER INFORMATION: Primer 1525p

<400> SEQUENCE: 94
agtgggtggt aggaattttt                                                 20

<210> SEQ ID NO 95
<211> LENGTH: 23
<212> TYPE: DNA
<213> ORGANISM: Unknown
<220> FEATURE:
<223> OTHER INFORMATION: Primer 1525o

<400> SEQUENCE: 95
ctcttctttt atttctcaaa cca                                             23

<210> SEQ ID NO 96
<211> LENGTH: 22
<212> TYPE: DNA
<213> ORGANISM: Unknown
<220> FEATURE:
<223> OTHER INFORMATION: Primer 1526p

<400> SEQUENCE: 96
ggattattta aggttgggat tt                                              22

<210> SEQ ID NO 97
<211> LENGTH: 22
<212> TYPE: DNA
<213> ORGANISM: Unknown
<220> FEATURE:
<223> OTHER INFORMATION: Primer 1526o

<400> SEQUENCE: 97
cctcttctca ctcctacttt ca                                              22

<210> SEQ ID NO 98
<211> LENGTH: 22
<212> TYPE: DNA
<213> ORGANISM: Unknown
<220> FEATURE:
<223> OTHER INFORMATION: Primer 1527p

<400> SEQUENCE: 98
aaaggtaagg tattgggaga tt                                              22
```

<210> SEQ ID NO 99
<211> LENGTH: 25
<212> TYPE: DNA
<213> ORGANISM: Unknown
<220> FEATURE:
<223> OTHER INFORMATION: Primer 1527o

<400> SEQUENCE: 99
caaaataaca acattacttc tcaaa                                          25

<210> SEQ ID NO 100
<211> LENGTH: 22
<212> TYPE: DNA
<213> ORGANISM: Unknown
<220> FEATURE:
<223> OTHER INFORMATION: Primer 1528p

<400> SEQUENCE: 100
agattggaat tgatagagga tg                                             22

<210> SEQ ID NO 101
<211> LENGTH: 24
<212> TYPE: DNA
<213> ORGANISM: Unknown
<220> FEATURE:
<223> OTHER INFORMATION: Primer 1528o

<400> SEQUENCE: 101
tcctaactaa cacaataaaa accc                                           24

<210> SEQ ID NO 102
<211> LENGTH: 22
<212> TYPE: DNA
<213> ORGANISM: Unknown
<220> FEATURE:
<223> OTHER INFORMATION: Primer 1529p

<400> SEQUENCE: 102
ggtttttagt gatggagaaa ag                                             22

<210> SEQ ID NO 103
<211> LENGTH: 22
<212> TYPE: DNA
<213> ORGANISM: Unknown
<220> FEATURE:
<223> OTHER INFORMATION: Primer 1529o

<400> SEQUENCE: 103
cactacttaa cctacccaat cc                                             22

<210> SEQ ID NO 104
<211> LENGTH: 24
<212> TYPE: DNA
<213> ORGANISM: Unknown
<220> FEATURE:
<223> OTHER INFORMATION: Primer 1530p

<400> SEQUENCE: 104
gagtaaggtg atagttaaag ggat                                           24

<210> SEQ ID NO 105
<211> LENGTH: 20
<212> TYPE: DNA
<213> ORGANISM: Unknown
<220> FEATURE:

<223> OTHER INFORMATION: Primer 1530o

<400> SEQUENCE: 105
caattacacc ccaaattctc                                                                           20

<210> SEQ ID NO 106
<211> LENGTH: 22
<212> TYPE: DNA
<213> ORGANISM: Unknown
<220> FEATURE:
<223> OTHER INFORMATION: Primer 1531p

<400> SEQUENCE: 106
taatgagtag tgggggtttt ag                                                                        22

<210> SEQ ID NO 107
<211> LENGTH: 22
<212> TYPE: DNA
<213> ORGANISM: Unknown
<220> FEATURE:
<223> OTHER INFORMATION: Primer 1531o

<400> SEQUENCE: 107
aataaacttt cacttccctc ct                                                                        22

<210> SEQ ID NO 108
<211> LENGTH: 22
<212> TYPE: DNA
<213> ORGANISM: Unknown
<220> FEATURE:
<223> OTHER INFORMATION: Primer 1532r

<400> SEQUENCE: 108
atctaaactc ccatccctta ac                                                                        22

<210> SEQ ID NO 109
<211> LENGTH: 22
<212> TYPE: DNA
<213> ORGANISM: Unknown
<220> FEATURE:
<223> OTHER INFORMATION: Primer 1532q

<400> SEQUENCE: 109
gttggttagg ttgttttttga at                                                                       22

<210> SEQ ID NO 110
<211> LENGTH: 22
<212> TYPE: DNA
<213> ORGANISM: Unknown
<220> FEATURE:
<223> OTHER INFORMATION: Primer 1533p

<400> SEQUENCE: 110
agggttatag ggtagatgtt ga                                                                        22

<210> SEQ ID NO 111
<211> LENGTH: 25
<212> TYPE: DNA
<213> ORGANISM: Unknown
<220> FEATURE:
<223> OTHER INFORMATION: Primer 1533o

<400> SEQUENCE: 111
tctaaatcct taatacaaca aacaa                                                                     25

```
<210> SEQ ID NO 112
<211> LENGTH: 22
<212> TYPE: DNA
<213> ORGANISM: Unknown
<220> FEATURE:
<223> OTHER INFORMATION: Primer 1534p

<400> SEQUENCE: 112
ggtttagagg aaggattgtt tt                                              22

<210> SEQ ID NO 113
<211> LENGTH: 21
<212> TYPE: DNA
<213> ORGANISM: Unknown
<220> FEATURE:
<223> OTHER INFORMATION: Primer 1534o

<400> SEQUENCE: 113
catactcaac tccctcacaa t                                               21

<210> SEQ ID NO 114
<211> LENGTH: 26
<212> TYPE: DNA
<213> ORGANISM: Unknown
<220> FEATURE:
<223> OTHER INFORMATION: Primer 1535r

<400> SEQUENCE: 114
aacttctaac ctaatccttt ctctaa                                          26

<210> SEQ ID NO 115
<211> LENGTH: 23
<212> TYPE: DNA
<213> ORGANISM: Unknown
<220> FEATURE:
<223> OTHER INFORMATION: Primer 1535q

<400> SEQUENCE: 115
tgtagtttta gttatttggg agg                                             23

<210> SEQ ID NO 116
<211> LENGTH: 22
<212> TYPE: DNA
<213> ORGANISM: Unknown
<220> FEATURE:
<223> OTHER INFORMATION: Primer 1536r

<400> SEQUENCE: 116
cccttaatac ttctacccca ta                                              22

<210> SEQ ID NO 117
<211> LENGTH: 22
<212> TYPE: DNA
<213> ORGANISM: Unknown
<220> FEATURE:
<223> OTHER INFORMATION: Primer 1536q

<400> SEQUENCE: 117
tgattaggtg gtttggttat tt                                              22

<210> SEQ ID NO 118
<211> LENGTH: 22
<212> TYPE: DNA
<213> ORGANISM: Unknown
<220> FEATURE:
<223> OTHER INFORMATION: Primer 1537p
```

```
<400> SEQUENCE: 118
attttatttt ggggaaagtt gt                                              22

<210> SEQ ID NO 119
<211> LENGTH: 22
<212> TYPE: DNA
<213> ORGANISM: Unknown
<220> FEATURE:
<223> OTHER INFORMATION: Primer 1537o

<400> SEQUENCE: 119
tcaataatac ccacttccta cc                                              22

<210> SEQ ID NO 120
<211> LENGTH: 22
<212> TYPE: DNA
<213> ORGANISM: Unknown
<220> FEATURE:
<223> OTHER INFORMATION: Primer 1538p

<400> SEQUENCE: 120
gttgttggaa tagagaggtt gt                                              22

<210> SEQ ID NO 121
<211> LENGTH: 21
<212> TYPE: DNA
<213> ORGANISM: Unknown
<220> FEATURE:
<223> OTHER INFORMATION: Primer 1538o

<400> SEQUENCE: 121
aacacaaaca taaaactccc c                                               21

<210> SEQ ID NO 122
<211> LENGTH: 22
<212> TYPE: DNA
<213> ORGANISM: Unknown
<220> FEATURE:
<223> OTHER INFORMATION: Primer 1539p

<400> SEQUENCE: 122
ttgtggtttt tgtagagggt at                                              22

<210> SEQ ID NO 123
<211> LENGTH: 22
<212> TYPE: DNA
<213> ORGANISM: Unknown
<220> FEATURE:
<223> OTHER INFORMATION: Primer 1539o

<400> SEQUENCE: 123
acaactttcc ccaaaataaa at                                              22

<210> SEQ ID NO 124
<211> LENGTH: 22
<212> TYPE: DNA
<213> ORGANISM: Unknown
<220> FEATURE:
<223> OTHER INFORMATION: Primer 1540p

<400> SEQUENCE: 124
aggttaagat tgggattagg tt                                              22

<210> SEQ ID NO 125
<211> LENGTH: 22
```

```
<212> TYPE: DNA
<213> ORGANISM: Unknown
<220> FEATURE:
<223> OTHER INFORMATION: Primer 1540o

<400> SEQUENCE: 125
ctactttcct ccaaaaactc ac                                              22

<210> SEQ ID NO 126
<211> LENGTH: 21
<212> TYPE: DNA
<213> ORGANISM: Unknown
<220> FEATURE:
<223> OTHER INFORMATION: Primer 1541p

<400> SEQUENCE: 126
ggtttgtgag gtgattgtgt a                                               21

<210> SEQ ID NO 127
<211> LENGTH: 24
<212> TYPE: DNA
<213> ORGANISM: Unknown
<220> FEATURE:
<223> OTHER INFORMATION: Primer 1541o

<400> SEQUENCE: 127
ttctcctcta ccctaatcta aaaa                                            24

<210> SEQ ID NO 128
<211> LENGTH: 22
<212> TYPE: DNA
<213> ORGANISM: Unknown
<220> FEATURE:
<223> OTHER INFORMATION: Primer 1542p

<400> SEQUENCE: 128
gggagagggt tttgataaga ta                                              22

<210> SEQ ID NO 129
<211> LENGTH: 22
<212> TYPE: DNA
<213> ORGANISM: Unknown
<220> FEATURE:
<223> OTHER INFORMATION: Primer 1542o

<400> SEQUENCE: 129
ccaactccct aataatctca ct                                              22

<210> SEQ ID NO 130
<211> LENGTH: 22
<212> TYPE: DNA
<213> ORGANISM: Unknown
<220> FEATURE:
<223> OTHER INFORMATION: Primer 1543p

<400> SEQUENCE: 130
gtgagattat tagggagttg gg                                              22

<210> SEQ ID NO 131
<211> LENGTH: 24
<212> TYPE: DNA
<213> ORGANISM: Unknown
<220> FEATURE:
<223> OTHER INFORMATION: Primer 1543o

<400> SEQUENCE: 131
```
aactaccata tccaccaatt aaaa                                                 24

<210> SEQ ID NO 132
<211> LENGTH: 22
<212> TYPE: DNA
<213> ORGANISM: Unknown
<220> FEATURE:
<223> OTHER INFORMATION: Primer 1544r

<400> SEQUENCE: 132
aactctactt cataacccct cc                                                   22

<210> SEQ ID NO 133
<211> LENGTH: 22
<212> TYPE: DNA
<213> ORGANISM: Unknown
<220> FEATURE:
<223> OTHER INFORMATION: Primer 1544q

<400> SEQUENCE: 133
gaggttgttt tgttaggatt tt                                                   22

<210> SEQ ID NO 134
<211> LENGTH: 22
<212> TYPE: DNA
<213> ORGANISM: Unknown
<220> FEATURE:
<223> OTHER INFORMATION: Primer 1545r

<400> SEQUENCE: 134
tctttaacaa attcaccatc aa                                                   22

<210> SEQ ID NO 135
<211> LENGTH: 21
<212> TYPE: DNA
<213> ORGANISM: Unknown
<220> FEATURE:
<223> OTHER INFORMATION: Primer 1545q

<400> SEQUENCE: 135
ttaagttagt ttgggggttt t                                                    21

<210> SEQ ID NO 136
<211> LENGTH: 22
<212> TYPE: DNA
<213> ORGANISM: Unknown
<220> FEATURE:
<223> OTHER INFORMATION: Primer 1546r

<400> SEQUENCE: 136
cctcccacct attaactatt ca                                                   22

<210> SEQ ID NO 137
<211> LENGTH: 22
<212> TYPE: DNA
<213> ORGANISM: Unknown
<220> FEATURE:
<223> OTHER INFORMATION: Primer 1546q

<400> SEQUENCE: 137
tattttggta ggggttgtat tt                                                   22

<210> SEQ ID NO 138
<211> LENGTH: 18
<212> TYPE: DNA
<213> ORGANISM: Unknown

```
<220> FEATURE:
<223> OTHER INFORMATION: Primer 1547p

<400> SEQUENCE: 138
gggtattatg ggtgggaa                                                    18

<210> SEQ ID NO 139
<211> LENGTH: 23
<212> TYPE: DNA
<213> ORGANISM: Unknown
<220> FEATURE:
<223> OTHER INFORMATION: Primer 1547o

<400> SEQUENCE: 139
aaaccaaaca ctacaataaa tcc                                              23

<210> SEQ ID NO 140
<211> LENGTH: 19
<212> TYPE: DNA
<213> ORGANISM: Unknown
<220> FEATURE:
<223> OTHER INFORMATION: Primer 1548r

<400> SEQUENCE: 140
acaaaacctc aacccaact                                                   19

<210> SEQ ID NO 141
<211> LENGTH: 24
<212> TYPE: DNA
<213> ORGANISM: Unknown
<220> FEATURE:
<223> OTHER INFORMATION: Primer 1548q

<400> SEQUENCE: 141 tggtattta ggaattggtt tatt                                              24

<210> SEQ ID NO 142
<211> LENGTH: 22
<212> TYPE: DNA
<213> ORGANISM: Unknown
<220> FEATURE:
<223> OTHER INFORMATION: Primer 1549r

<400> SEQUENCE: 142
ctttcaactt cactctttcc at                                               22

<210> SEQ ID NO 143
<211> LENGTH: 21
<212> TYPE: DNA
<213> ORGANISM: Unknown
<220> FEATURE:
<223> OTHER INFORMATION: Primer 1549q

<400> SEQUENCE: 143
gggttgttgg aggttagtag t                                                21

<210> SEQ ID NO 144
<211> LENGTH: 22
<212> TYPE: DNA
<213> ORGANISM: Unknown
<220> FEATURE:
<223> OTHER INFORMATION: Primer 1550r

<400> SEQUENCE: 144
tcctccctaa caaaatatca at                                               22
```

```
<210> SEQ ID NO 145
<211> LENGTH: 22
<212> TYPE: DNA
<213> ORGANISM: Unknown
<220> FEATURE:
<223> OTHER INFORMATION: Primer 1550q

<400> SEQUENCE: 145
ttgaagtgta gtggtgtgat tt                                              22

<210> SEQ ID NO 146
<211> LENGTH: 22
<212> TYPE: DNA
<213> ORGANISM: Unknown
<220> FEATURE:
<223> OTHER INFORMATION: Primer 1551p

<400> SEQUENCE: 146
ttaagataag taaaagggtg gg                                              22

<210> SEQ ID NO 147
<211> LENGTH: 22
<212> TYPE: DNA
<213> ORGANISM: Unknown
<220> FEATURE:
<223> OTHER INFORMATION: Primer 1551o

<400> SEQUENCE: 147
ctctaaaatt catccacaaa ca                                              22

<210> SEQ ID NO 148
<211> LENGTH: 22
<212> TYPE: DNA
<213> ORGANISM: Unknown
<220> FEATURE:
<223> OTHER INFORMATION: Primer 1552p

<400> SEQUENCE: 148
ggttagggat tttggtttta at                                              22

<210> SEQ ID NO 149
<211> LENGTH: 21
<212> TYPE: DNA
<213> ORGANISM: Unknown
<220> FEATURE:
<223> OTHER INFORMATION: Primer 1552o

<400> SEQUENCE: 149
taacccactc tcaacacaaa c                                               21

<210> SEQ ID NO 150
<211> LENGTH: 22
<212> TYPE: DNA
<213> ORGANISM: Unknown
<220> FEATURE:
<223> OTHER INFORMATION: Primer 1553r

<400> SEQUENCE: 150
aaacccaact cctatcctaa ac                                              22

<210> SEQ ID NO 151
<211> LENGTH: 22
<212> TYPE: DNA
<213> ORGANISM: Unknown
<220> FEATURE:
<223> OTHER INFORMATION: Primer 1553q
```

<400> SEQUENCE: 151
gggtgagatt ttagaggatt tt                                              22

<210> SEQ ID NO 152
<211> LENGTH: 22
<212> TYPE: DNA
<213> ORGANISM: Unknown
<220> FEATURE:
<223> OTHER INFORMATION: Primer 1554p

<400> SEQUENCE: 152
attgaagaag atggtggata ag                                              22

<210> SEQ ID NO 153
<211> LENGTH: 23
<212> TYPE: DNA
<213> ORGANISM: Unknown
<220> FEATURE:
<223> OTHER INFORMATION: Primer 1554o

<400> SEQUENCE: 153
cctaacttct ctaaaacaaa ccc                                             23

<210> SEQ ID NO 154
<211> LENGTH: 22
<212> TYPE: DNA
<213> ORGANISM: Unknown
<220> FEATURE:
<223> OTHER INFORMATION: Primer 1555r

<400> SEQUENCE: 154
accaatctta aaccaaacct ta                                              22

<210> SEQ ID NO 155
<211> LENGTH: 24
<212> TYPE: DNA
<213> ORGANISM: Unknown
<220> FEATURE:
<223> OTHER INFORMATION: Primer 1555q

<400> SEQUENCE: 155
aatttttagg aggtattttt gttg                                            24

<210> SEQ ID NO 156
<211> LENGTH: 22
<212> TYPE: DNA
<213> ORGANISM: Unknown
<220> FEATURE:
<223> OTHER INFORMATION: Primer 1556r

<400> SEQUENCE: 156
cccacaacta actattctct cc                                              22

<210> SEQ ID NO 157
<211> LENGTH: 22
<212> TYPE: DNA
<213> ORGANISM: Unknown
<220> FEATURE:
<223> OTHER INFORMATION: Primer 1556q

<400> SEQUENCE: 157
tttattggtt tgagagtttt tg                                              22

<210> SEQ ID NO 158

```
<211> LENGTH: 19
<212> TYPE: DNA
<213> ORGANISM: Unknown
<220> FEATURE:
<223> OTHER INFORMATION: Primer 1557r

<400> SEQUENCE: 158
accccacaac ctactcaaa                                               19

<210> SEQ ID NO 159
<211> LENGTH: 22
<212> TYPE: DNA
<213> ORGANISM: Unknown
<220> FEATURE:
<223> OTHER INFORMATION: Primer 1557q

<400> SEQUENCE: 159
aggatagtag agggagttag gg                                           22

<210> SEQ ID NO 160
<211> LENGTH: 22
<212> TYPE: DNA
<213> ORGANISM: Unknown
<220> FEATURE:
<223> OTHER INFORMATION: Primer 1456o

<400> SEQUENCE: 160
caaaccaacc tcatataaca aa                                           22

<210> SEQ ID NO 161
<211> LENGTH: 22
<212> TYPE: DNA
<213> ORGANISM: Unknown
<220> FEATURE:
<223> OTHER INFORMATION: Primer 1456p

<400> SEQUENCE: 161
gaggggaagt aggataggat ta                                           22

<210> SEQ ID NO 162
<211> LENGTH: 22
<212> TYPE: DNA
<213> ORGANISM: Unknown
<220> FEATURE:
<223> OTHER INFORMATION: Primer 1558r

<400> SEQUENCE: 162
attcctaatc tcacacacaa cc                                           22

<210> SEQ ID NO 163
<211> LENGTH: 22
<212> TYPE: DNA
<213> ORGANISM: Unknown
<220> FEATURE:
<223> OTHER INFORMATION: Primer 1558q

<400> SEQUENCE: 163
tgagtagttg gataaaaatg gg                                           22

<210> SEQ ID NO 164
<211> LENGTH: 19
<212> TYPE: DNA
<213> ORGANISM: Unknown
<220> FEATURE:
<223> OTHER INFORMATION: Primer 1559p

<400> SEQUENCE: 164
```

-continued

```
gttggaagag atttgggtg                                              19

<210> SEQ ID NO 165
<211> LENGTH: 22
<212> TYPE: DNA
<213> ORGANISM: Unknown
<220> FEATURE:
<223> OTHER INFORMATION: Primer 1559o

<400> SEQUENCE: 165
attatcccca ccttcctaaa ta                                          22

<210> SEQ ID NO 166
<211> LENGTH: 20
<212> TYPE: DNA
<213> ORGANISM: Unknown
<220> FEATURE:
<223> OTHER INFORMATION: Primer 1560p

<400> SEQUENCE: 166
ggttgagaaa gttgttggag                                             20

<210> SEQ ID NO 167
<211> LENGTH: 21
<212> TYPE: DNA
<213> ORGANISM: Unknown
<220> FEATURE:
<223> OTHER INFORMATION: Primer 1560o

<400> SEQUENCE: 167
caaactaatc acaaacccaa a                                           21

<210> SEQ ID NO 168
<211> LENGTH: 22
<212> TYPE: DNA
<213> ORGANISM: Unknown
<220> FEATURE:
<223> OTHER INFORMATION: Primer 1561r

<400> SEQUENCE: 168
accccaacta ccttaccttt at                                          22

<210> SEQ ID NO 169
<211> LENGTH: 25
<212> TYPE: DNA
<213> ORGANISM: Unknown
<220> FEATURE:
<223> OTHER INFORMATION: Primer 1561q

<400> SEQUENCE: 169
atttggtttt agtgagtttt tgtat                                       25

<210> SEQ ID NO 170
<211> LENGTH: 24
<212> TYPE: DNA
<213> ORGANISM: Unknown
<220> FEATURE:
<223> OTHER INFORMATION: Primer 1562r

<400> SEQUENCE: 170
aattttccta aaccttctac ctaa                                        24

<210> SEQ ID NO 171
<211> LENGTH: 20
<212> TYPE: DNA
```

```
<213> ORGANISM: Unknown
<220> FEATURE:
<223> OTHER INFORMATION: Primer 1562q

<400> SEQUENCE: 171 gtgttgggggg atataaggat                                              20

<210> SEQ ID NO 172
<211> LENGTH: 20
<212> TYPE: DNA
<213> ORGANISM: Unknown
<220> FEATURE:
<223> OTHER INFORMATION: Primer 1563p

<400> SEQUENCE: 172
aaggtgaagg ggaagtaagt                                               20

<210> SEQ ID NO 173
<211> LENGTH: 23
<212> TYPE: DNA
<213> ORGANISM: Unknown
<220> FEATURE:
<223> OTHER INFORMATION: Primer 1563o

<400> SEQUENCE: 173
cctaataacc tttatcacca aaa                                           23

<210> SEQ ID NO 174
<211> LENGTH: 20
<212> TYPE: DNA
<213> ORGANISM: Unknown
<220> FEATURE:
<223> OTHER INFORMATION: Primer 1564r

<400> SEQUENCE: 174
ctctctcacc tcttccaaaa                                               20

<210> SEQ ID NO 175
<211> LENGTH: 22
<212> TYPE: DNA
<213> ORGANISM: Unknown
<220> FEATURE:
<223> OTHER INFORMATION: Primer 1564q

<400> SEQUENCE: 175
gtaagtagtt ggggtagtga gg                                            22

<210> SEQ ID NO 176
<211> LENGTH: 21
<212> TYPE: DNA
<213> ORGANISM: Unknown
<220> FEATURE:
<223> OTHER INFORMATION: Primer 1565r

<400> SEQUENCE: 176
atctaacacc ctcaataccc t                                             21

<210> SEQ ID NO 177
<211> LENGTH: 21
<212> TYPE: DNA
<213> ORGANISM: Unknown
<220> FEATURE:
<223> OTHER INFORMATION: Primer 1565q

<400> SEQUENCE: 177
gagtgggtgg gatttatagt t                                             21
```

```
<210> SEQ ID NO 178
<211> LENGTH: 20
<212> TYPE: DNA
<213> ORGANISM: Unknown
<220> FEATURE:
<223> OTHER INFORMATION: Primer 1566r

<400> SEQUENCE: 178
ccccaaatac cctaaaccta                                               20

<210> SEQ ID NO 179
<211> LENGTH: 22
<212> TYPE: DNA
<213> ORGANISM: Unknown
<220> FEATURE:
<223> OTHER INFORMATION: Primer 1566q

<400> SEQUENCE: 179
gttggagaag gggagatata ga                                            22

<210> SEQ ID NO 180
<211> LENGTH: 22
<212> TYPE: DNA
<213> ORGANISM: Unknown
<220> FEATURE:
<223> OTHER INFORMATION: Primer 1567r

<400> SEQUENCE: 180
attccaaaaa cctcatctaa aa                                            22

<210> SEQ ID NO 181
<211> LENGTH: 20
<212> TYPE: DNA
<213> ORGANISM: Unknown
<220> FEATURE:
<223> OTHER INFORMATION: Primer 1567q

<400> SEQUENCE: 181
tttggtaagg gggataaaat                                               20
```

EPIGENETIC MARKER FOR THE IDENTIFICATION OF NATURAL KILLER CELLS

CROSS REFERENCE TO A RELATED APPLICATION

Figure 1:
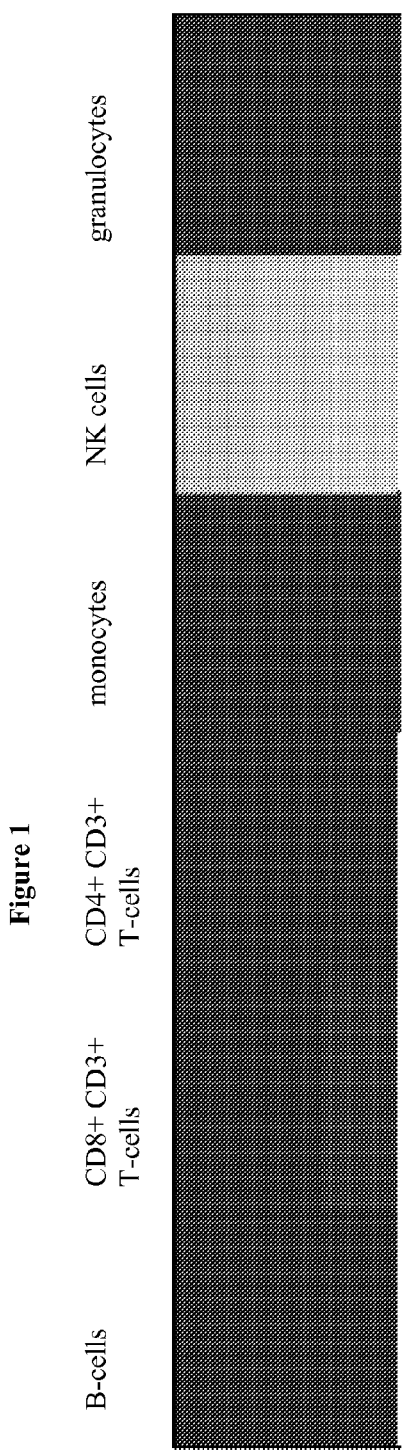

This application is a National Stage Application of International Application Number PCT/EP2010/055722, filed Apr. 28, 2010; which claims priority to European Application No. 09005876.9, filed Apr. 28, 2009; which are incorporated herein by reference in their entirety.

The Sequence Listing for this application is labeled "December2011_ST25.txt", which was created on Dec. 12, 2011, and is 180 KB. The entire contents are incorporated herein by reference in their entirety.

The present invention relates to a method, in particular an in vitro method for identifying natural killer cells of a mammal, preferably CD3−, non T-lymphocyte derived NK cells, but in certain embodiments also CD3+ NKT cells, which often express the surface proteins CD16 and/or CD56, comprising analyzing the methylation status of at least one CpG position in the CX3CR1 and/or FGR and/or NKG7 and/or GNLY genes, in particular their upstream regulatory regions, and in particular the promoter and other conserved regions of the genes CX3CR1 and/or FGR and/or NKG7 and/or GNLY, wherein a demethylation of at least one CpG in the analyzed sample to at least 70% is indicative for CD56 expressing NK cells, which might also be CD8+ or CD8−, CD56 dim or bright, CD16+ or CD16− NK cells. The methods of the present invention are useful for the detection, the quantification and quality assurance and control of NK cells. Furthermore, the present invention relates to a kit for performing the above methods as well as respective uses of the inventive methods or kits. The present invention furthermore provides an improved method for analysing the methylation status of at least one CpG position in the gene CX3CR1 and/or FGR and/or NKG7 and/or GNLY genes that allows for a precise analysis even from sub-optimal quality samples, such as non-freshly obtained blood, tissue or serum samples.

BACKGROUND OF THE INVENTION

Natural killer cells are granular cytotoxic lymphocytes, derived from CD34+ hematopoietic progenitor cells (HPCs). They represent an essential component of the innate immune system. They comprise about 5 to 20% of lymphocytes in the spleen, liver, and peripheral blood and are also present—even if at lower frequencies—in the bone marrow, the thymus, and in lymph nodes. They were originally identified by their ability to kill certain (tumor-) target cells without sensitization. This killing works in vivo and in vitro and is not restricted by the target cell's expression of major histocompatibility complex (MHC) molecules. NK cells also possess natural cytotoxic activity against conspicious, such as but not restricted to (virus-) infected and/or tumor, cells. In addition, they mediate antibody-dependent cellular cytotoxicity (ADCC) of targets through FcεRIII (CD16), a receptor that binds the Fc portion of antibodies.

In general, the traditional identifier for human NK cells is the absence of the T cell receptor complex (TCR, CD3), along with the expression of CD56, a 140-kDa isoform of neural cell adhesion molecule (NCAM). Based on their CD56 receptor expression density, human NK cells are often further subdivided into $CD56^{dim}$ or $CD56^{bright}$ NK cells. In the periphery, the majority (>90%) of NK cells have been found to consist of $CD56^{dim}$ along with high expression of CD16, and the remaining 10% are $CD56^{bright}$ NK cells coming along with low or no expression of CD16.

The described $CD56^{dim}$ NK cell fraction is generally considered the "classical cytotoxic NK cell subset". The $CD56^{bright}$ fraction displays much lower cytotoxicity and, instead, produces high amounts of cytokines, including IFNγ and TNFα, indicating a primary role in immunoregulatory function.

The measurement of the cellular components in the blood is generally considered easier than that of other organs, since the cells are (at least in the periphery) not adherent or matrixed in a scaffolded organ. However, this is only partially true, since with the current methods, which mostly use the surface expression of so called CD (cluster of differentiation) antigens, it still remains challenging to determine the cell types in clinical routine applications. This is because for the cell sorting analysis as commonly used the cell samples need to be freshly isolated or immediately fixated in order to keep the cell entities intact. The blood/immunological methods used for blood component measurement for blood cells present in other tissues, including solid tissues at or after inflammation, and or the growth of solid tumors are limited, since they represent at most semi-quantitative methods (of particular relevance is the immunohistochemistry). The identification of specific epigenetic markers will greatly facilitate the clinical routine application of the measurement of blood cell types.

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

Aberrant methylation of DNA frequently accompanies the transformation from healthy to cancerous cells. Among the observed effects are genome-wide hypomethylation, increased methylation of tumour suppressor genes and hypomethylation of many oncogenes (reviewed by Jones and Laird, Nature Genetics 21:163-167, 1999; Esteller, Oncogene 21:5427-5440, 2002; Laird, Nature Reviews/Cancer 3:253-266, 2003). Methylation profiles have been recognised to be tumour specific (i.e., changes in the methylation pattern of particular genes or even individual CpGs are diagnostic of particular tumour types) and there is now an extensive collection of diagnostic markers for bladder, breast, colon, oesophagus, stomach, liver, lung, and prostate cancers (summarized by Laird, Nature Reviews/Cancer 3:253-266, 2003).

EP 1213360 describes a method of identifying a cell, tissue or nucleus, comprising collecting information on the methylation pattern of DNA isolated from the cell, tissue or nucleus and analyzing the resultant information.

WO 2004/050706 describes a sub-group of T-cells, and relates to characteristics of regulatory T-cells which define them as such. The application also describes the uses of such T-cells, compositions comprising them and chemokines which recruit them in the modulation of an immune response.

Finally, EP 1826279 describes a method, in particular an in vitro method for identifying FoxP3-positive regulatory T cells, preferably CD25+ CD4+ regulatory T cells of a mammal, comprising analyzing the methylation status of at least one CpG position in the gene foxp3 or an orthologous or paralogous gene thereof, and the use of DNA-methylation analysis of the gene of the transcription factor FoxP3 for a detection and quality assurance and control of regulatory T cells.

In view of the above, it is an object of the present invention, to provide an improved method based on DNA methylation analysis as a superior tool in order to more conveniently and reliably identify NK cells and all different subsets of that cell type. Measurement can be done independent of purification, storage and to quite some extend also to tissue quality.

In a first aspect, the invention solves the above problem by providing a method for identifying natural killer cells in a sample derived from a mammal, comprising analysing the methylation status of at least one CpG position in one or more of the regions of one or more genes selected from NKG7, CX3CR1, FGR and GNLY, wherein a demethylation of at least one CpG position to at least 70% in said sample is indicative for a CD56 expressing natural killer cell. In a preferred embodiment, said natural killer cells of said mammal are preferably CD3−, non T-lymphocyte derived NK cells, but in certain embodiments also encompass CD3+ NKT cells.

In particular, methods of the invention are preferred, wherein said at least one CpG position in said sample is demethylated to more than 80% and preferably more than 90% and most preferred more than 95%.

A further embodiment of the invention then comprises the inventive method, wherein said at least one CpG position is present in the 5' region upstream from the transcription start, promoter region, the 5' or 3' untranslated regions, intron, and/or exon/intron border or in the 3' region downstream of the transcriptional stop. The invention provides that said at least one CpG position is preferably selected from the CpG positions of any of the genes CX3CR1 according to SEQ ID NO: 1, preferably selected from the CpG positions of the amplicon CX3CR1-1 (1452) according to SEQ ID NO: 5 or CX3CR1 amplicons ROI956 to 966, according to SEQ ID NOs: 6 to 16; FGR according to SEQ ID NO: 2, preferably of the amplicons FGR-1 (Amp. 1454) according to SEQ ID NO: 17 or FGR amplicons ROI967-977 according to SEQ ID NOs: 18 to 28; GNLY according to SEQ ID NO: 3, preferably of the amplicons GNLY 1 (1458) according to SEQ ID NO: 29 or GNLY amplicons ROI978 to 982 according to SEQ ID NOs: 30 to 34 and/or NKG7 according to SEQ ID NO: 4, preferably of the amplicons NKG7-1 (1455) according to SEQ ID NO: 35 or NKG7 amplicons ROI983 to 988 according to SEQ ID NOs: 36 to 41.

Yet another aspect relates to a method according to the present invention, wherein the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. Also preferred is an additional analysis of the marker CD56, CD16 and/or CD8.

In particular, the inventors regard the herein described methods to be suitable for routine application, for example on a DNA-chip. Samples are selected from a fresh, fresh-frozen or fully prepared (such as formalin fixed paraffin embedded) sample, including mammalian body fluid, preferable human blood samples, serum samples or tumourous or non-tumourous solid tissue samples, organ or cell type blood sample, a sample of blood lymphocytes or a fraction thereof. These samples should be mammalian, preferably mouse, rat, monkey or human. Especially preferred is a mammal, most preferred a human, which suffers from or is likely to suffer from autoimmune diseases, viral or bacterial infections, transplant rejections, cancer, and/or allergy or any disease directly correlated to NK cells, such as—including but not limited to—diseases as phenotypically described by SCID-X1.

Another embodiment of the invention relates to the above methods, wherein said identification comprises a distinction and, optionally, a further quantification, of said natural killer cells from all major peripheral blood cell types or non-blood cells, and then further comprises the step of concluding on the immune status of said mammal based on said natural killer cells as identified. Hereby, in a sample of a mammal, including whole blood or various subfractions as well as tissues or isolated subfractions of tissues, NK cells can be identified and quantified due to their (unique) methylation pattern in the analysed genes. Based on this they can be quantitated.

Another aspect then relates to a method of the invention, wherein a demethylation of at least one CpG position in a first gene selected from NKG7, CX3CR1, FGR and GNLY in combination with a demethylation of at least one CpG position of at least a second gene selected from NKG7, CX3CR1, FGR and GNLY is indicative for a CD56$^{dim}$ or CD56$^{bright}$ natural killer cell. A preferred aspect then relates to a method of the invention, wherein a demethylation of at least one CpG position of NKG7 to at least 70% in combination with a demethylation of at least one CpG position of a gene selected from CX3CR1, FGR and GNLY to at least 70% in said sample is indicative for a CD56$^{dim}$ or CD56$^{bright}$ or CD8$^+$ or CD8$^-$ natural killer cell.

In a further aspect the inventive method is useful for monitoring the level of CD56 expressing natural killer cells, in particular CD56$^{dim}$ or CD56$^{bright}$, and/or CD16$^+$ or CD16$^-$, and/or CD8$^+$ or CD8$^-$ natural killer cells in a mammal, comprising a method according to the invention, and comparing the amount of natural killer cells as identified to an earlier sample taken from the same mammal, and/or to a control sample.

In another aspect of the present invention, the method is also useful for measuring and/or monitoring the amount of said natural killer cells in response to chemical and/or biological substances that are provided to said mammal.

In yet another aspect, the invention provides an amplicon according to SEQ ID NOs: 5 to 41 or an amplicon produced by a primer-pair according to SEQ ID NOs: 42 to 181, and/or an oligomer hybridizing to a sequence selected from SEQ ID NOs: 1 to 41, preferably an oligomer selected from SEQ ID NOs: 42 to 181.

The invention also provides a kit for identifying and/or monitoring natural killer cells, in particular CD56$^{dim}$ or CD56$^{bright}$, and/or CD16$^+$ or CD16$^-$, and/or CD8$^+$ or CD8$^-$ natural killer cells, in a mammal based on the analysis of the methylation status of CpG positions in one or more genes selected from CX3CR1, FGR, NKG7 and GNLY, comprising materials for performing a method according to the invention.

Such an inventive kit comprises, but is not limited to, a) a bisulphite reagent, and b) materials for the methylation analysis of CpG positions selected from the CpG positions of the gene CX3CR1 according to SEQ ID NO: 1, preferably selected from the CpG positions of the amplicon CX3CR1-1 (1452)

according to SEQ ID NO: 5 or CX3CR1 amplicons ROI956-966, according to SEQ ID NOs: 6-16; FGR according to SEQ ID NO: 2, preferably of the amplicons FGR-1 (Amp. 1454) according to SEQ ID NO: 17 or FGR amplicons ROI967-977 according to SEQ ID NOs: 18-28; GNLY according to SEQ ID NO: 3, preferably of the amplicons GNLY 1 (1458) according to SEQ ID NO: 29 or GNLY amplicons ROI978-982 according to SEQ ID NOs: 30-34 and/or NKG7 according to SEQ ID NO: 4, preferably of the amplicons NKG7-1 (1455) according to SEQ ID NO: 35 or NKG7 amplicons ROI983-988 according to SEQ ID NOs: 36-41.

DETAILED DESCRIPTION OF THE INVENTION

The present invention solves the above problem that the detection of NK cells is problematic for routine applications by providing a method for identifying NK cells of a mammal, comprising analysing the methylation status of at least one CpG position in one or various, for example regulatory, potentially differentially methylated regions of the genes CX3CR1 and/or FGR and/or NKG7 and/or GNLY, wherein a demethylation of at least one CpG to at least 90% is indicative for CD56 expressing NK cells.

In another preferred embodiment of the present invention, the inventors furthermore present a novel and more specific way in order to monitor NK cells in all human body fluids, including human blood samples, or in any given (solid) tissue, organ or cell type.

The inventive concept is generally based on a specific demethylation of the CX3CR1 and/or FGR and/or NKG7 and/or GNLY regions in NK cells. Using a simple and precise quantitative PCR method, as a signal amplification method (e.g. a precise quantitative PCR method), the inventors show that the CX3CR1 and/or FGR and/or NKG7 and/or GNLY demethylation represents surrogate markers for lymphocyte counts in blood or tissues. The present inventors have thus identified particular regions within the CX3CR1 and/or FGR and/or NKG7 and/or GNLY genes that are functionally involved in, or reliably associated with, the existence of natural killer cells.

In one preferred embodiment, the preferred region for this identification is either the promoter, first intron or exon regions of, for example, the nucleotide sequence according to SEQ ID No. 1 and other regions containing a number of CpG motifs that exhibit a differential methylation status in cells expressing CD56 in either $CD56^{high}$ or $CD56^{dim}$ cells, which may or may not also express CD16 and CD8 compared with other cells not expressing CD56, using, for example, the bisulphite sequencing method or real time PCR analysis.

One further preferred embodiment is the distinction between and among functionally different fractions of natural NK cells, such as the cytotoxic sub-fraction (often characterized by the surface markers $CD56^{dim}$, and likely $CD16^{high}$) and the cytokine producing sub-fraction (i.e., often described as $CD56^{bright}$ and $CD16^{low/medium}$) or between CD8 positive and CD8 negative NK cell fractions or any other sub-fractions of NK cells. While, for the identification of the general NK cell population, a particular preferred embodiment is the identification by the bimodal marker NKG7, the inventors consider the fractionation of the subgroups such as $CD56^{dim}$ vs. $CD56^{bright}$ or CD8 positive or CD8 negative, the combination of NKG7 with the respective markers of CX3CR1, FGR and/or GNLY a preferred embodiment. Here, for example, the entire NK population might be typed and quantified by the proportion of NKG7 demethylated cells, while determining the $CD56^{bright}$ alternatively the $CD56^{dim}$ population by the full demethylation of CX3CR1, FGR or GNLY.

An implementation example would be that in a sample of full blood, the number of cells with an unmethylated NKG7 region determines the absolute number of NK-like cells, while the number of CX3CR1 or FGR or GNLY demethylated cells determines the proportion of truly cytotoxic or cytokine expressing NK cells. In such setting and as one embodiment, using the demethylation of CXCR1, FGR or GNLY alone would provide for the identification of cytotoxic, cytokine producing or CD8 positive or negative cells alone NK cells only, without determining the amount of the other NK or other cell fractions.

The inventors could demonstrate that in all or particular fractions of NK cells, such as $CD56^{bright}$ or $CD56^{dim}$ and/or CD16 positive or negative and CD8 positive or negative NK cells (defined by the principle ability to express CD56) the CpG motifs are almost completely demethylated (i.e. to more than 70%, preferably 80%, preferably, more than 90% and most preferred more than 95%), whereas the same motifs are completely methylated in all non-NK cells. Determination of the methylation status of the CX3CR1 and/or FGR and/or NKG7 and/or GNLY loci is a valuable tool to identify NK cells, such as will be required/or at least of some value for measuring NK cells in autoimmune diseases, (viral) infections, transplant rejections, cancer, allergy, or just the NK cell related immune status in any envisionable context, when desired. The assay allows measurement of NK cells without purification or any staining procedures. As a particularly preferred embodiment, the measurement of NK cells by either of the markers described in here can be easily detected and quantified from within solid tissue samples of healthy or diseased nature, including tumorous or non-tumourous tissues. For such analysis it is possible to make the analysis either from fresh, fresh-frozen or any type of conserved (such as, for example, formalin fixed and/or paraffin-embedded) tissue. Another preferred embodiment is to determine the ratio between NK cells on one hand and CD3+ T lymphocytes, CD19 positive B cells, FOXP3 CD25 CD3+ cells, monocytes and/or granulocytes.

The inventors have shown that the potential to form NK cell properties of mammalian immune cells coincide with epigenetic, i.e., DNA methylation based regulation in the genes CX3CR1 and/or FGR and/or NKG7 and/or GNLY. DNA methylation is a biologically and chemically stable epigenetic modification, resulting in long-term gene expression changes. The inventors found demethylation at the human CX3CR1 and/or FGR and/or NKG7 and/or GNLY loci to be restricted to NK cells when tested against all major peripheral blood cell types and a selection of non-blood cells. These data indicated that epigenetic modifications in the CX3CR1 and/or FGR and/or NKG7 and/or GNLY loci serve as valuable marker for the identification of cells with the phenotype of NK cells, regardless of the expression of any genes.

The present invention relies on the surprising finding that in a particular region of the gene for CX3CR1 and/or FGR and/or NKG7 and/or GNLY, the so-called "NK-SDR"s (NK cell specific demethylated regions), the CpG motifs are almost completely demethylated to more than 70%, preferably more than 80%, more preferably to more than 90%, preferably 91%, even more preferably more than 92% and most preferred more than 95%, whereas the same motifs are completely methylated in all non NK cells. Thus, this region provides a valuable and reliable tool for a diagnostic analysis according to the present invention.

NKG7

The gene NKG7 in humans is located on the reverse strand of chromosome 19. The gene region spans roughly 1.3 kb comprising 5' and 3' UTRs, 4 exons and 3 intronic regions (Ensembl release 53, March 2009). There is only evidence for a single splice variant of the gene, a mature transcript of 826 nucleotides which encodes for 165 amino acids of the final NKG7 protein product.

In a further aspect, a preferred NK-SDR of the present invention is the 5' UTR of NKG7, or preferable the 3' UTR of NKG7. Furthermore, natural killer cell specific demethylated regions of the present invention are located within the intronic sequences of this gene. In particular preferred are also NK-SDRs that are located around the exon-intron boundaries of NKG7, preferably the boundary between the first exon and first intron and/or the first intron and second exon and/or the second exon and second intron and/or the second intron and third exon and/or the third exon and third intron and/or the third intron and fourth exon, or any possible preferred combination of the above.

It is well established in the art that important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention, NK-SDRs are provided, which are located within 10000 bases upstream of the transcriptional start site of NKG7, preferably 9000 bases, 8000 bases, 7000 bases, 6000 bases, 5000 bases, 4000 bases, 3000 bases or 2000 bases upstream of NKG7, even more preferred is a region 1000 bases upstream of the transcriptional start of NKG7 and most preferable NK-SDRs in the first 500 bases upstream of the transcriptional start site of NKG7. It is, however, particularly preferred that NK-SDRs of the present invention are located within the gene promoter of NKG7.

Moreover, preferred embodiments of the present invention comprise NK-SDRs downstream of the open reading frame (ORF) of NKG7, preferably within 10000 bases downstream of the ORF of NKG7, more preferable 8000 bases downstream of NKG7, even more preferred is a region 6000 bases downstream of the ORF of NKG7, preferably 4000 bases downstream of NKG7 and most preferable NK-SDRs in the first 2000 bases downstream of the ORF of NKG7.

The present invention further preferably provides groups of NK-SDRs of NKG7, which comprise any possible combination of the aforementioned preferred NK-SDRs of NKG7.

Another aspect of the invention then relates to NK-SDRs of NKG7 that are found within the regions of SEQ ID NO: 4, preferably a region selected from the group of SEQ ID NOs: 35 to 41, preferably of SEQ ID NO: 35, or any combinations thereof. Further preferred are amplicons of NKG7 which are generated using a primer pair according to SEQ ID NOs: 160 to 181, wherein primers having the same number in their name, but differ in the last position of the name, are pairs.

CX3CR1

The gene CX3CR1 in humans is located on the reverse strand of chromosome 3. The gene region spans roughly 18.5 kb genomic DNA comprising 5' and 3' UTRs, 3 exons and 2 intronic regions (Ensembl release 53, March 2009). There are three alternatively spliced variants of the transcript that encode for final protein products ranging in size between 355 to 387 amino acids.

In a further aspect, a preferred NK-SDR of the present invention is the 5' UTR of CX3CR1, or preferable the 3' UTR of CX3CR1. Furthermore, natural killer cell specific demethylated regions of the present invention are located within the intronic sequences of this gene. In particular preferred are also NK-SDRs that are located around the exon-intron boundaries of CX3CR1, preferably the boundary between the first exon and first intron and/or the first intron and second exon and/or the second exon and the second intron and/or the second intron and third exon, or any possible preferred combination of the above.

It is well established in the art that important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention NK-SDRs are provided, which are located within 20000 bases upstream of the transcriptional start site of CX3CR1, preferable 15000 bases upstream of CX3CR1, even more preferred is a region 10000 bases, 9000 bases, 8000 bases, 7000 bases, 6000 bases, 5000 bases, 4000 bases, 3000 bases, 2000 bases or 1000 bases upstream of the transcriptional start of CX3CR1, and most preferable NK-SDRs in the first 500 bases upstream of the transcriptional start site of CX3CR1. It is, however, particularly preferred that NK-SDRs of the present invention are located within the gene promoter of CX3CR1.

Moreover, preferred embodiments of the present invention comprise NK-SDRs downstream of the open reading frame (ORF) of CX3CR1, preferably within 10000 bases downstream of the ORF of CX3CR1, more preferable 8000 bases downstream of CX3CR1, even more preferred is a region 6000 bases downstream of the ORF of CX3CR1, preferably 4000 bases downstream of CX3CR1 and most preferable NK-SDRs in the first 2000 bases downstream of the ORF of CX3CR1.

The present invention further preferably provides groups of NK-SDRs of CX3CR1, which comprise any possible combination of the aforementioned preferred NK-SDRs of CX3CR1.

Another aspect of the invention then relates to NK-SDRs of CX3CR1 that are found within the regions of SEQ ID NO: 1, preferably a region selected from the group of SEQ ID NOs: 5 to 16, preferably of SEQ ID NO: 5, or any combinations thereof. Further preferred are amplicons of CX3CR1 which are generated using a primer pair according to SEQ ID NOs: 50 to 95, wherein primers having the same number in their name, but differ in the last position of the name, are pairs.

FGR

The gene FGR in humans is located on the reverse strand of chromosome 1. The gene region spans about 23.12 kb genomic DNA comprising 5' and 3' UTRs, 11 exons and 10 intronic regions (Ensembl release 53, March 2009). There are 4 alternatively spliced variants of the transcript that, however, differ only in their respective 3' UTRs. All splice variants encode a mature protein of 529 amino acids.

In a further aspect, a preferred NK-SDR of the present invention is the 5' UTR of FGR, or preferable the 3' UTR of FGR. Furthermore, natural killer cell specific demethylated regions of the present invention are located within the intronic sequences of this gene. In particular preferred are also NK-SDRs that are located around the exon-intron boundaries of FGR, preferably the boundary between the first exon and first intron and/or the first intron and second exon and/or the second exon and the second intron and/or the second intron and third exon and/or the third exon and third intron and/or the third intron and fourth exon and/or the fourth exon and fourth intron and/or the fourth intron and fifth exon and/or the fifth exon and fifth intron and/or the fifth intron and sixth exon and/or the sixth exon and sixth intron, and/or the sixth intron and seventh exon and/or the seventh exon and seventh intron and/or the seventh intron and eighth exon and/or the eighth exon and eighth exon and/or the eighth intron and ninth exon and/or the ninth exon and ninth intron and/or the ninth intron and tenth exon and/or the tenth exon and tenth intron and/or the tenth intron and eleventh exon, or any possible preferred combination of the above.

It is well established in the art that important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention NK-SDRs are provided, which are located within 10000 bases upstream of the transcriptional start site of FGR, preferable 9000 bases, 8000 bases, 7000 bases, 6000 bases, 5000 bases, 4000 bases, 3000 bases or 2000 bases upstream of FGR, even more preferred is a region 1000 bases upstream of the transcriptional start of FGR, and most preferable NK-SDRs in the first 500 bases upstream of the transcriptional start site of FGR. It is, however, particularly preferred that NK-SDRs of the present invention are located within the gene promoter of FGR.

Moreover, preferred embodiments of the present invention comprise NK-SDRs downstream of the open reading frame (ORF) of FGR, preferably within 10000 bases downstream of the ORF of FGR, more preferable 8000 bases downstream of FGR, even more preferred is a region 6000 bases downstream of the ORF of FGR, preferably 4000 bases downstream of FGR and most preferable NK-SDRs in the first 2000 bases downstream of the ORF of FGR.

The present invention further preferably provides groups of NK-SDRs of FGR, which comprise any possible combination of the aforementioned preferred NK-SDRs of FGR.

Another aspect of the invention then relates to NK-SDRs of FGR that are found within the regions of SEQ ID NO: 2, preferably a region selected from the group of SEQ ID NOs: 17 to 28, preferably of SEQ ID NO: 17, or any combinations thereof. Further preferred are amplicons of FGR which are generated using a primer pair according to SEQ ID NO: 96 to 137, wherein primers having the same number in their name, but differ in the last position of the name, are pairs.

GNLY

The gene GNLY in humans is located on the forward strand of the second chromosome. The gene region spans 4.7 kb of genomic DNA comprising 5' and 3' UTRs, 6 exons and 5 intronic regions (Ensembl release 53, March 2009). There are 4 alternatively spliced variants of the transcript that encode protein products of between 89 and 145 amino acids.

In a further aspect, a preferred NK-SDR of the present invention is the 5' UTR of GNLY, or preferable the 3' UTR of GNLY. Furthermore, natural killer cell specific demethylated regions of the present invention are located within the intronic sequences of this gene. In particular preferred are also NK-SDRs that are located around the exon-intron boundaries of GNLY, preferably the boundary between the first exon and first intron and/or the first intron and second exon and/or the second exon and the second intron and/or the second intron and third exon and/or the third exon and third intron and/or the third intron and fourth exon and/or the fourth exon and fourth intron and/or the fourth intron and fifth exon and/or the fifth exon and fifth intron and/or the fifth intron and sixth exon, or any possible preferred combination of the above.

It is well established in the art, that important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention NK-SDRs are provided, which are located within 10000 bases upstream of the transcriptional start site of GNLY, preferable 9000 bases, 8000 bases, 7000 bases, 6000 bases, 5000 bases, 4000 bases, 3000 bases or 2000 bases upstream of GNLY, even more preferred is a region 1000 bases upstream of the transcriptional start of GNLY and most preferable NK-SDRs in the first 500 bases upstream of the transcriptional start site of GNLY. It is, however, particularly preferred that NK-SDRs of the present invention are located within the gene promoter of GNLY.

Moreover, preferred embodiments of the present invention comprise NK-SDRs downstream of the open reading frame (ORF) of GNLY, preferably within 10000 bases downstream of the ORF of GNLY, more preferable 8000 bases downstream of GNLY, even more preferred is a region 6000 bases downstream of the ORF of GNLY, preferably 4000 bases downstream of GNLY and most preferable NK-SDRs in the first 2000 bases downstream of the ORF of GNLY.

The present invention further preferably provides groups of NK-SDRs of GNLY, which comprise any possible combination of the aforementioned preferred NK-SDRs of GNLY.

Another aspect of the invention then relates to NK-SDKs of GNLY that are found within the regions of SEQ ID NO: 3, preferably a region selected from the group of SEQ ID NOs: 29 to 34, preferably of SEQ ID NO: 29, or any combinations thereof. Further preferred are amplicons of GNLY which are generated using a primer pair according to SEQ ID NOs: 138 to 159, wherein primers having the same number in their name, but differ in the last position of the name, are pairs.

Yet, the next aspect of the invention then relates to combined natural killer cell specific demethylation regions, wherein the combinations of the invention are composed of the single preferred NK-SDRs of the above genes NKG7, CX3CR1, FGR and GNLY. Thus, preferably for the analysis of a sample of cells, multiple demethylation patterns of NK-SDRs are combined to conclude the presence of a CD56 expressing natural killer cell or a sub-fraction of natural killer cells, preferably $CG56^{dim}$ or $CD56^{bright}$ NK cells and/or CD16+ or CD16− NK cells and/or CD8+ or CD8− NK cells.

In another embodiment, the method according to the present invention is preferred, wherein said analysis of the methylation status comprises amplification with at least one primer of the primer pairs useful to amplify an amplicon selected from the group comprising SEQ ID NOs: 5 to 41.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight Sequencing methyl specific restriction assays. With the amplification, the amplicon of the NK-SDR or any other region in the CX3CR1 and/or FGR and/or NKG7 and/or GNLY genes or any paralog or ortholog as described herein is produced that is a particularly preferred "tool" for performing the method(s) according to the present invention. Consequently, an oligomer according to any of SEQ ID NOs: 42 to 181 or the amplicon as amplified by the primer pair selected from SEQ ID NOs: 42 to 181 constitute preferred embodiments of the present invention, or any other sequence in the CX3CR1 and/or FGR and/or NKG7 and/or GNLY loci.

The person of skill will furthermore be able to select specific subsets of CpG positions in order to minimise the amount of sites to be analyzed, for example all sites as present on the amplicons according to SEQ ID No 5 to 41, or any other sequence in the CX3CR1 and/or FGR and/or NKG7 and/or GNLY genes.

In order to analyze the methylation status of CpG positions, any known method to analyse DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

Another important aspect of the present invention then relates to an amplicon according to SEQ ID NOs: 5 to 41 or an amplicon produced by a primer-pair according to SEQ ID NOs: 42 to 181, and/or an oligomer hybridizing to a sequence selected from SEQ ID NOs: 1 to 41, preferably an oligomer selected from SEQ ID NOs: 42 to 181. These amplicons provide important tools for performing preferred embodiments of the methods of the present invention.

Furthermore, preferred is a method according to the invention, further comprising the step of analysing the cellular markers CD56, CD16 and/or CD8. In order to analyze these additional markers, any known method to analyse expression can be used, such as methods using antibodies, and/or methylation analysis. The analysis of these markers preferably further improves the accuracy of the analysis, and might allow to identify sub-sets of cells. Thus, the method according to the present invention comprises an identification that is a distinction of said natural killer cells from all major peripheral blood cell types or non-blood cells.

The method according to the present invention can be performed with any mammal having the above markers or orthologs or paralogs thereof, preferred is a method according to the present invention, wherein said mammal is a mouse, rat, monkey or human, preferably a human.

The method(s) according to the present invention can be performed in vitro and/or in vivo. In general, all biological samples can be used, as long as they contain suitable cells or suitable DNA of cells of interest. Preferred is a method wherein said sample is selected from a fresh, fresh-frozen or fully prepared sample including mammalian body fluid, preferable human blood samples, serum samples or a tumourous or non-tumourous solid tissue, organ or cell type blood sample, a sample of blood lymphocytes or a fraction thereof.

Another preferred aspect of the present invention then relates to the use of the method according to the present invention as above in diagnostics and the use in monitoring diseases. Thereby, the invention is directed at a method according to the present invention which further comprises the step of concluding on the immune status of said mammal based on said natural killer cells as identified. In said method according to the invention, a demethylation of at least one CpG position in a first gene selected from NKG7, CX3CR1, FGR and GNLY in combination with a demethylation of at least one CpG position in at least a second gene selected from NKG7, CX3CR1, FGR, and GNLY is indicative for a $CD56^{dim}$ or $CD56^{bright}$ natural killer cell.

Another important aspect of the present invention then relates to a method according to the present invention for monitoring the level of CD56 expressing natural killer cells, in particular $CD56^{dim}$ or $CD56^{bright}$, and/or CD16+ or CD16−, and/or CD8+ or CD8− natural killer cells in a mammal, comprising a method according to the invention as above, and comparing the amount of natural killer cells as identified with an earlier sample taken from the same mammal, and/or with a control sample. Preferably, said method is performed on a sample from a mammal suffering from or is likely to suffer from autoimmune diseases, transplant rejections, cancer, allergy and/or any disease directly correlated to NK cells, such as, but not limited to SCID-X1.

Further preferred, said method according to the invention then further comprises measuring and/or monitoring the amount of the amount of natural killer cells in response to chemical and/or biological substances that are provided to said mammal. That is, changes in the amount or ratio of natural killer cells that are caused by, for example, the treatment of a disease (e.g. as described herein), and the success and/or progress of said treatment in terms of an effect on the natural killer cells can be followed using this method. A follow-up of the methylation pattern based on the markers herein will point to changes in the cells that are due to a response to said chemical and/or biological substances, in some cases even before a phenotypic change can be observed.

In yet another aspect of the present invention, the present invention provides a method for identifying chemical and/or biological substances that selectively modulate natural killer cells expressing the markers as described herein, comprising contacting one or more of said chemical and/or biological substance with said natural killer cells, and detecting, whether said chemical and/or biological substance modulates the methylation of the CpG positions as analyzed, and/or whether said one or more of said chemical and/or biological substance selectively modulates the amount and/or ratio of marker-expressing natural killer cells. Particularly preferred is a modulation of said natural killer cells that increases the amount and/or ratio of said natural killer cells.

The method can be performed in vitro and/or in vivo. In this aspect, the present invention provides a method, sometimes called a "screening-method", that seeks to identify chemical and/or biological substances modulating expression of the markers as above that can be used as starting points for the development of natural killer cell-specific medication and respective pharmaceutical compositions. The present method is based on the fact that it is well accepted that the marker genes as identified herein must play a central role for the development of natural killer cells. Therefore, factors stimulating marker expression are interesting for the treatment of patients. Such factors, which lead to a stable modification, preferably induction, of the development/ratio/amount of natural killer cells, can be detected with the method described in this invention.

Chemical and/or biological substances that are suitable as screening compounds are known to the person of skill and, for example, include small molecules, peptides and proteins, and antibodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 80%, preferably 90%, and more preferably 95%.

Another important aspect of the present invention then relates to a method according to the present invention, which further comprises the step of providing a treatment for a patient suffering from or being likely to suffer from autoimmune diseases, transplant rejections, cancer, allergy and/or any disease directly correlated to NK cells, such as, but not limited to SCID-X1, wherein said treatment modulates, and preferably increases the amount and/or proportion of NK cells in said, preferably, cancer patient. Preferred is a method according to the present invention, wherein said treatment is selected from providing chemical and/or biological substances that selectively stimulate NK cells in said patient, or a treatment that stimulates the expression of the marker genes as above or supports the biological activity of said marker genes in said NK cells in said patient. Preferred examples of such treatments are demethylating agents that provide for an reduced methylation of said genes.

Yet another preferred aspect of the present invention relates to an improved method of treatment of diseases that are related to marker gene expression, such as autoimmune diseases, transplant rejections, cancer, allergy and/or any disease directly correlated to NK cells, such as, but not limited to SCID-X1, comprising a method as described herein above. The term "treatment" also includes a prevention of marker gene expression related diseases.

In yet another aspect of the present invention, the present invention provides a kit for identifying and/or monitoring natural killer cells, in particular $CD56^{dim}$ or $CD56^{bright}$, and/or CD16+ or CD16−, and/or CD8+ or CD8− natural killer cells, in a mammal based on the analysis of the methylation status of CpG positions in one or more genes selected from CX3CR1, FGR, NKG7 and GNLY, comprising materials for performing a method according to any of claims 1 to 13, in particular a kit comprising a) a bisulfite reagent, and b) materials for the methylation analysis of CpG positions selected from the CpG positions of the gene CX3CR1-1 (1452) according to SEQ ID NO: 5, or CX3CR1 amplicons ROI956 to 966, according to SEQ ID NOs: 6 to 16; FGR according to SEQ ID NO: 2, preferably of the amplicon FGR-1 (Amp. 1454) according to SEQ ID NO: 17, or FGR amplicons ROI967 to 977 according to SEQ ID NOs: 18 to 28; GNLY according to SEQ ID NO: 3, preferably of the amplicon GNLY 1 (1458) according to SEQ ID NO: 29, or GNLY amplicons ROI978 to 982 according to SEQ ID NOs: 30 to 34 and/or NKG7 according to SEQ ID NO: 4, preferably of the amplicon NKG7-1 (1455) according to SEQ ID NO: 35 or NKG7 amplicons ROI983 to 988 according to SEQ ID NOs: 36 to 41. The person of skill will furthermore be able to select materials for specific subsets of CpG positions in order to minimize the amount of sites to be analyzed, for example all sites as present on an amplicon as above or all sites as present on another amplicon as above, or orthologous or paralogous CpG positions thereof. The kit can be a diagnostic kit.

In yet another aspect of the present invention, the present invention relates to the use of an oligomer or amplicon according to the present invention or a kit according to the present invention for identifying and/or monitoring $CD56^{dim}$ or $CD56^{bright}$, and/or CD16+ or CD16−, and/or CD8+ or CD8− natural killer cells in a mammal.

The present invention will now be further described in more detail in the form of preferred embodiments thereof in the following examples, nevertheless, without being limited thereto. For the purposes of the present invention, all references as cited herein are incorporated by reference in their entireties.

BRIEF DESCRIPTION OF THE DRAWINGS AND SEQUENCES

FIG. 1 shows the measurement of various leukocyte cell fractions, including NK cells (second from the left). Each line represents an exemplary individual CpG in the selected and representative amplicon of the gene CX3CR1 (amplicon 1452: CX3CR1-1, SEQ ID NO: 5). Beginning from the left each respective row shows the methylation of the given CpGs in B cells, CD8 positive CD3+ T cells, CD4 positive CD3+ cells, monocytes, NK cells, and granulocytes. The gray tones indicate the level of methylation in each cell type.

Figure 2:
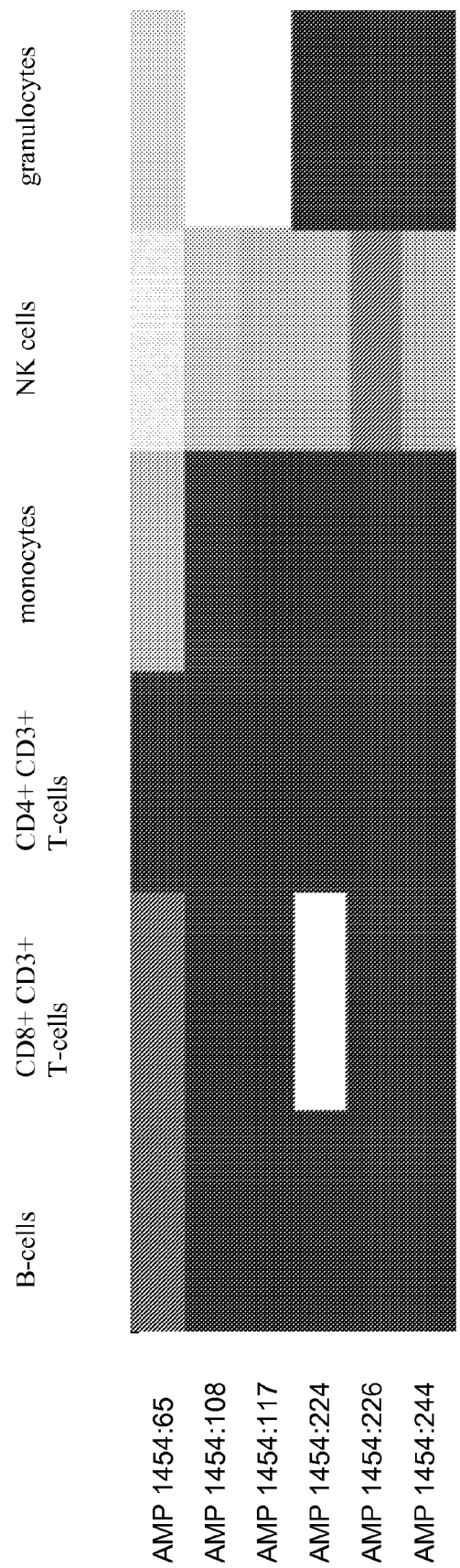

FIG. 2 shows the measurement of various leukocyte cell fractions, including NK cells. Each line represents an exemplary individual CpG in the selected and representative amplicon of the gene FGR (amplicon 1454: FGR-1, SEQ ID NO: 17). Beginning from the left each respective row shows the methylation of the named CpGs in B cells, CD8 positive CD3+ T cells, CD4 positive CD3+ cells, monocytes, NK cells, and granulocytes. The gray tones indicate the level of methylation in each cell type.

Figure 3:
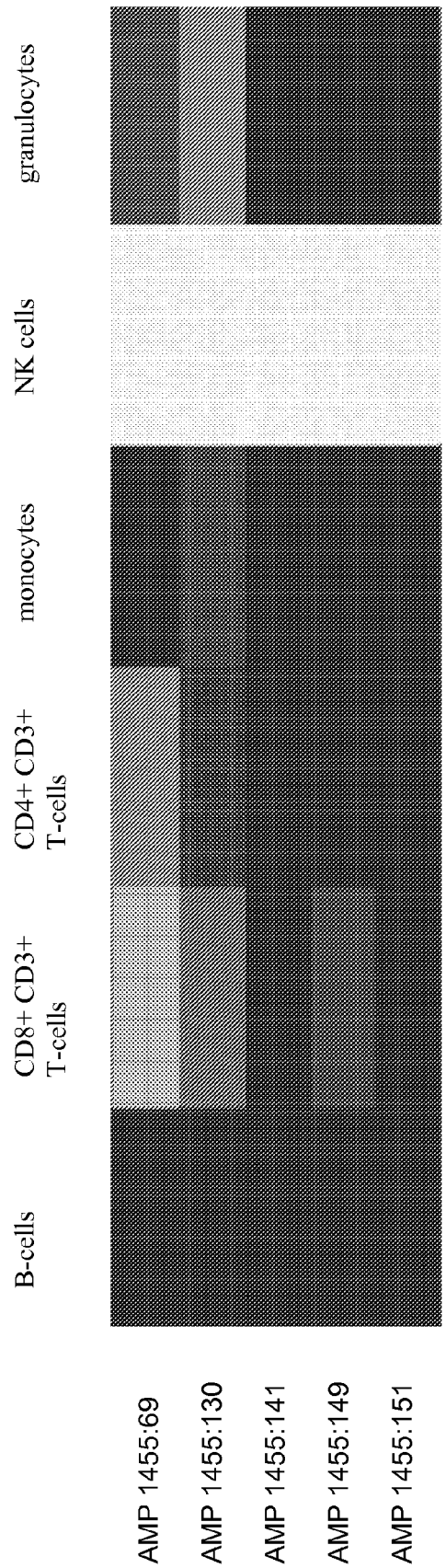

FIG. 3 shows the measurement of various leukocyte cell fractions, including NK cells. Each line represents an exemplary individual CpG in the selected and representative amplicon of the gene NKG7 (amplicon 1455: NKG7-1, SEQ ID NO: 35). Beginning from the left each respective row shows the methylation of the named CpGs in B cells, CD8 positive CD3+ T cells, CD4 positive CD3+ cells, monocytes, NK cells, and granulocytes. The gray tones indicate the level of methylation in each cell type.

FIG. 4 shows the measurement of various leukocyte cell fractions, including NK cells. Each line represents an exemplary individual CpG in the selected and representative amplicon of the gene GNLY (amplicon 1458: GNLY-1, SEQ ID NO: 29). Beginning from the left each respective row shows the methylation of the named CpGs in B cells, CD8 positive CD3+ T cells, CD4 positive CD3+ cells, monocytes, NK cells, and granulocytes. The gray tones indicate the level of methylation in each cell type.

SEQ ID NO: 1 shows the nucleotide sequence of the human gene region of CX3CR;

SEQ ID NO: 2 shows the nucleotide sequence of the human gene region of FGR;

SEQ ID NO: 3 shows the nucleotide sequence of the human gene region of GNLY;

SEQ ID NO: 4 shows the nucleotide sequence of the human gene region of NKG7;

SEQ ID NO: 5 shows nucleotide sequences of the CX3CR1 amplicons CX3CR1-1;

SEQ ID NOs: 6 to 16 show nucleotide sequences of the CX3CR1 amplicons ROI956 to 966;

SEQ ID NO: 17 shows nucleotide sequences of the FGR amplicons FGR-1;

SEQ ID NOs: 18 to 28 show nucleotide sequences of the FGR amplicons ROI967 to 977;

SEQ ID NO: 29 shows nucleotide sequences of the GNLY amplicons GNLY-1;

SEQ ID NOs: 30 to 34 show nucleotide sequences of the GNLY amplicons ROI978 to 982;

SEQ ID NO: 35 shows nucleotide sequences of the NKG7 amplicons NKG7-1;

SEQ ID NOs: 36 to 41 show nucleotide sequences of the NKG7 amplicons ROI983 to 988; and SEQ ID NOs: 42 to 181: show primer sequences as listed in table 1.

TABLE 1

Primer Sequences

| Primer Name | Target Gene Name | Sequence | SEQ ID NO: |
|---|---|---|---|
| 1455o | NKG7 | TAAAACTATAAATCCCACCCAC | 42 |
| 1455p | NKG7 | AAGGATTAGGAGAAGAAGGTTT | 43 |
| 1452q | CX3CR1 | TAGGGGTTAGGTAGGTAATGAA | 44 |
| 1452r | CX3CR1 | ACACAACTCTTCTCCTCAAAAT | 45 |
| 1454o | FGR | CCAACCCCAAAAATATAAACAT | 46 |
| 1454p | FGR | ATGTGGGTAAATGAGGATGTAG | 47 |

TABLE 1-continued

Primer Sequences

| Primer Name | Target Gene Name | Sequence | SEQ ID NO: |
|---|---|---|---|
| 1458q | GNLY | ATTGGATTAAGTTTGGTTTTGA | 48 |
| 1458r | GNLY | ACCCTAAACTACTTCTTCACACA | 49 |
| 1503r | CX3CR1 | CCCCAAACTTAAAATTCAATAC | 50 |
| 1503q | CX3CR1 | TTAGGAGAAGTTGTTATTGGT | 51 |
| 1504p | CX3CR1 | AGGTAGGGGATTAGGAAAGTAG | 52 |
| 1504o | CX3CR1 | AATTCCAACCAAATAAAAACAT | 53 |
| 1505p | CX3CR1 | ATTTAAGTAGTGAGGATGGAGG | 54 |
| 1505o | CX3CR1 | CCAATAAACCAATCTTTCCTAA | 55 |
| 1506p | CX3CR1 | TTTAGAAATGGGAAGGGG | 56 |
| 1506o | CX3CR1 | AAAAATCACTAAACCTACAACAAA | 57 |
| 1507r | CX3CR1 | AAACCCTTTACAAAATCAAAAA | 58 |
| 1507q | CX3CR1 | GGATAGTAGTAGGGATGTGGAA | 59 |
| 1508p | CX3CR1 | TGTTTTGTAAATTATGGAGTGAGT | 60 |
| 1508o | CX3CR1 | AAAACCTACCACTATATCCACC | 61 |
| 1509r | CX3CR1 | TCACTCATTACCCAAACTAAAA | 62 |
| 1509q | CX3CR1 | TTAGAGGAAGTGGTGTGTGTAG | 63 |
| 1510r | CX3CR1 | CCATTCTCCTACCTCAACC | 64 |
| 1510q | CX3CR1 | AAAAATAAAAGTTAAGGGGTTTATAG | 65 |
| 1511r | CX3CR1 | CACAATCCAATCATACTCTTTTAAT | 66 |
| 1511q | CX3CR1 | ATGTAATGTGGGTTAGGTATGG | 67 |
| 1512p | CX3CR1 | AATTGGGAGGTAGTAGAGTGGT | 68 |
| 1512o | CX3CR1 | TCACCCAAACAAAAATACTAAA | 69 |
| 1513p | CX3CR1 | GGAAGGGAAGAGAGTTTGTTA | 70 |
| 1513o | CX3CR1 | ACCCCTTAATACCTCTCCTAAA | 71 |
| 1514p | CX3CR1 | TTAGTGTTAGAAAGTGGATGGG | 72 |
| 1514o | CX3CR1 | AATCTATAACCCCTTCAAAACC | 73 |
| 1515p | CX3CR1 | TTTTATTTTTAGGTTGGGGTAA | 74 |
| 1515o | CX3CR1 | ACTCTTCCATCCCCTTAAAC | 75 |
| 1516p | CX3CR1 | AGGGGAATTTTGTTGTTTTAT | 76 |
| 1516o | CX3CR1 | ACAACTTTCTTCCTTACTCACA | 77 |
| 1517p | CX3CR1 | GGGTGGAAAATATGGTTTTTA | 78 |
| 1517o | CX3CR1 | AATAATCCTCAAAACTCTCCAA | 79 |
| 1518r | CX3CR1 | TTACATTACTCAAAACATCCCA | 80 |
| 1518q | CX3CR1 | TTATTTGTGAAGTGGGGTTAGT | 81 |
| 1519p | CX3CR1 | TTTTTGGGGTTGAGAATTTA | 82 |
| 1519o | CX3CR1 | TCTACAAACTACACTCCCCTTC | 83 |
| 1520p | CX3CR1 | GGAATGTTAGGTTTAGAGGTTTT | 84 |
| 1520o | CX3CR1 | CAAACTACAATACCCTTTTCTCA | 85 |
| 1521r | CX3CR1 | AACCTTCACCATAAATCAATTC | 86 |
| 1521q | CX3CR1 | GGTGTTGTTATTAAAATGGTTGT | 87 |
| 1522p | CX3CR1 | AAAATGAATGTTTTGGTGATTA | 88 |
| 1522o | CX3CR1 | AACACTTCCATACCTACTCCTTT | 89 |
| 1523p | CX3CR1 | AAAAGTTTAGAGTTGGTTGGG | 90 |
| 1523o | CX3CR1 | CTTCCCACTTACCATCTTATTT | 91 |
| 1524p | CX3CR1 | TTTATTGTTATGGGGAAAATTG | 92 |
| 1524o | CX3CR1 | AAAAATTCCTACCACCCACT | 93 |
| 1525p | CX3CR1 | AGTGGGTGGTAGGAATTTTT | 94 |
| 1525o | CX3CR1 | CTCTTCTTTTATTTCTCAAACCA | 95 |
| 1526p | FGR | GGATTATTTAAGGTTGGGATTT | 96 |
| 1526o | FGR | CCTCTTCTCACTCCTACTTTCA | 97 |
| 1527p | FGR | AAAGGTAAGGTATTGGGAGATT | 98 |
| 1527o | FGR | CAAAATAACAACATTACTTCTCAAA | 99 |
| 1528p | FGR | AGATTGGAATTGATAGAGGATG | 100 |
| 1528o | FGR | TCCTAACTAACACAATAAAAACCC | 101 |
| 1529p | FGR | GGTTTTTAGTGATGGAGAAAAG | 102 |
| 1529o | FGR | CACTACTTAACCTACCCAATCC | 103 |
| 1530p | FGR | GAGTAAGGTGATAGTTAAAGGGAT | 104 |
| 1530o | FGR | CAATTACACCCCAAATTCTC | 105 |
| 1531p | FGR | TAATGAGTAGTGGGGTTTTAG | 106 |
| 1531o | FGR | AATAAACTTTCACTTCCCTCCT | 107 |
| 1532r | FGR | ATCTAAACTCCCATCCCTTAAC | 108 |
| 1532q | FGR | GTTGGTTAGGTTGTTTTTGAAT | 109 |
| 1533p | FGR | AGGGTTATAGGGTAGATGTTGA | 110 |
| 1533o | FGR | TCTAAATCCTTAATACAACAAACAA | 111 |
| 1534p | FGR | GGTTTAGAGGAAGGATTGTTTT | 112 |
| 1534o | FGR | CATACTCAACTCCCTCACAAT | 113 |
| 1535r | FGR | AACTTCTAACCTAATCCTTTCTCTAA | 114 |
| 1535q | FGR | TGTAGTTTAGTTATTTGGGAGG | 115 |
| 1536r | FGR | CCCTTAATACTTCTACCCCATA | 116 |
| 1536q | FGR | TGATTAGGTGGTTTGGTTATTT | 117 |
| 1537p | FGR | ATTTTATTTTGGGGAAAGTTGT | 118 |
| 1537o | FGR | TCAATAATACCCACTTCCTACC | 119 |
| 1538p | FGR | GTTGTTGGAATAGAGAGGTTGT | 120 |
| 1538o | FGR | AACACAAACATAAAACTCCCC | 121 |

TABLE 1-continued

Primer Sequences

| Primer Name | Target Gene Name | Sequence | SEQ ID NO: |
|---|---|---|---|
| 1539p | FGR | TTGTGGTTTTTGTAGAGGGTAT | 122 |
| 1539o | FGR | ACAACTTTCCCCAAAATAAAAT | 123 |
| 1540p | FGR | AGGTTAAGATTGGGATTAGGTT | 124 |
| 1540o | FGR | CTACTTTCCTCCAAAAACTCAC | 125 |
| 1541p | FGR | GGTTTGTGAGGTGATTGTGTA | 126 |
| 1541o | FGR | TTCTCCTCTACCCTAATCTAAAAA | 127 |
| 1542p | FGR | GGGAGAGGGTTTTGATAAGATA | 128 |
| 1542o | FGR | CCAACTCCCTAATAATCTCACT | 129 |
| 1543p | FGR | GTGAGATTATTAGGGAGTTGGG | 130 |
| 1543o | FGR | AACTACCATATCCACCAATTAAAA | 131 |
| 1544r | FGR | AACTCTACTTCATAACCCCTCC | 132 |
| 1544q | FGR | GAGGTTGTTTGTTAGGATTTT | 133 |
| 1545r | FGR | TCTTTAACAAATTCACCATCAA | 134 |
| 1545q | FGR | TTAAGTTAGTTTGGGGGTTTT | 135 |
| 1546r | FGR | CCTCCCACCTATTAACTATTCA | 136 |
| 1546q | FGR | TATTTTGGTAGGGGTTGTATTT | 137 |
| 1547p | GNLY | GGGTATTATGGGTGGGAA | 138 |
| 1547o | GNLY | AAACCAAACACTACAATAAATCC | 139 |
| 1548r | GNLY | ACAAAACCTCAACCCAACT | 140 |
| 1548q | GNLY | TGGTATTTTAGGAATTGGTTTATT | 141 |
| 1549r | GNLY | CTTTCAACTTCACTCTTTCCAT | 142 |
| 1549q | GNLY | GGGTTGTTGGAGGTTAGTAGT | 143 |
| 1550r | GNLY | TCCTCCCTAACAAAATATCAAT | 144 |
| 1550q | GNLY | TTGAAGTGTAGTGGTGTGATTT | 145 |
| 1551p | GNLY | TTAAGATAAGTAAAAGGGTGGG | 146 |
| 1551o | GNLY | CTCTAAAATTCATCCACAAACA | 147 |
| 1552p | GNLY | GGTTAGGGATTTTGGTTTTAAT | 148 |
| 1552o | GNLY | TAACCCACTCTCAACACAAAC | 149 |
| 1553r | GNLY | AAACCCAACTCCTATCCTAAAC | 150 |
| 1553q | GNLY | GGGTGAGATTTTAGAGGATTTT | 151 |
| 1554p | GNLY | ATTGAAGAAGATGGTGGATAAG | 152 |
| 1554o | GNLY | CCTAACTTCTCTAAAACAAACCC | 153 |
| 1555r | GNLY | ACCAATCTTAAACCAAACCTTA | 154 |
| 1555q | GNLY | AATTTTTAGGAGGTATTTTTGTTG | 155 |
| 1556r | GNLY | CCCACAACTAACTATTCTCTCC | 156 |
| 1556q | GNLY | TTTATTGGTTTGAGAGTTTTG | 157 |
| 1557r | GNLY | ACCCCACAACCTACTCAAA | 158 |
| 1557q | GNLY | AGGATAGTAGAGGGAGTTAGGG | 159 |
| 1456o | NKG7 | CAAACCAACCTCATATAACAAA | 160 |
| 1456p | NKG7 | GAGGGGAAGTAGGATAGGATTA | 161 |
| 1558r | NKG7 | ATTCCTAATCTCACACACAACC | 162 |
| 1558q | NKG7 | TGAGTAGTTGGATAAAAATGGG | 163 |
| 1559p | NKG7 | GTTGGAAGAGATTTGGGTG | 164 |
| 1559o | NKG7 | ATTATCCCCACCTTCCTAAATA | 165 |
| 1560p | NKG7 | GGTTGAGAAAGTTGTTGGAG | 166 |
| 1560o | NKG7 | CAAACTAATCACAAACCCAAA | 167 |
| 1561r | NKG7 | ACCCCAACTACCTTACCTTTAT | 168 |
| 1561q | NKG7 | ATTTGGTTTTAGTGAGTTTTTGTAT | 169 |
| 1562r | NKG7 | AATTTTCCTAAACCTTCTACCTAA | 170 |
| 1562q | NKG7 | GTGTTGGGGATATAAGGAT | 171 |
| 1563p | NKG7 | AAGGTGAAGGGGAAGTAAGT | 172 |
| 1563o | NKG7 | CCTAATAACCTTTATCACCAAAA | 173 |
| 1564r | NKG7 | CTCTCTCACCTCTTCCAAAA | 174 |
| 1564q | NKG7 | GTAAGTAGTTGGGGTAGTGAGG | 175 |
| 1565r | NKG7 | ATCTAACACCCTCAATACCCT | 176 |
| 1565q | NKG7 | GAGTGGGTGGGATTTATAGTT | 177 |
| 1566r | NKG7 | CCCCAAATACCCTAAACCTA | 178 |
| 1566q | NKG7 | GTTGGAGAAGGGGAGATATAGA | 179 |
| 1567r | NKG7 | ATTCCAAAAACCTCATCTAAAA | 180 |
| 1567q | NKG7 | TTTGGTAAGGGGATAAAAT | 181 |

EXAMPLES

The inventors analyzed the methylation status of a multitude of candidate gene regions (amplicons) of NKG7, CX3CR1, FGR and GNLY within various cell types in comparison with an isolated fraction of natural killer cells. Surprisingly it was found, that specific areas in the genomic regions of the genes NKG7, CX3CR1, FGR and GNLY are significantly demethylated in natural killer cells compared to any other cell type.

TABLE 2

Positive-Identifiers for NK-Cells. Demethylated in NK-cells, methylated in all other cell types

| CpG-ID | Gene | Ovar | Whole Blood (Pool) | PBMC | Monocyte CD14+ BCST19 | Granulocyte CD15+ BCST18 | TH cells naive CD4+CD27+ CD45RA+ BCST21 | Th cells mem CD4+CD27+ CD45RA− BCST22 |
|---|---|---|---|---|---|---|---|---|
| cg22917487 | CX3CR1 | 0.88 | 0.83 | 0.89 | 0.92 | 0.92 | 0.94 | 0.90 |
| cg11254522 | FGR | 0.88 | 0.56 | 0.51 | 0.48 | 0.27 | 0.89 | 0.88 |
| cg25066857 | GNLY | 0.78 | 0.68 | 0.71 | 0.73 | 0.86 | 0.83 | 0.37 |
| cg12916723 | NKG7 | 0.73 | 0.65 | 0.66 | 0.79 | 0.57 | 0.93 | 0.85 |
| cg10126923 | NKG7 | 0.79 | 0.46 | 0.34 | 0.31 | 0.04 | 0.91 | 0.86 |

| CpG-ID | CTL naive CD8+CD27+ CD45RA+ BCST23 | CTL mem CD8+CD27+ CD45RA− BCST24 | B cells naive CD19+ CD45RA+ BCST25 | B cells mem CD19+CD45RA− BCST26 | Mean Value other cell Types | NK cells CD56+ BCS T20 | Methylation Difference Other-NK |
|---|---|---|---|---|---|---|---|
| cg22917487 | 0.92 | 0.59 | 0.57 | 0.79 | 0.83 | 0.13 | 0.69130567 |
| cg11254522 | 0.84 | 0.54 | 0.65 | 0.64 | 0.68 | 0.06 | 0.619407677 |
| cg25066857 | 0.79 | 0.17 | 0.58 | 0.54 | 0.63 | 0.11 | 0.520561154 |
| cg12916723 | 0.82 | 0.21 | 0.66 | 0.73 | 0.70 | 0.13 | 0.566323828 |
| cg10126923 | 0.86 | 0.15 | 0.71 | 0.84 | 0.61 | 0.06 | 0.544229773 |

* other cell types comprise all cells mentioned here, except whole blood or PBMCs Example 1

NKG7 Analysis

The inventors have purified various blood subsets including CD3/CD4, CD3/CD8 naïve and memory T lymphocytes, CD56 natural killer cells, CD19 naïve and memory B cells, CD14 monocytes and CD15 granulocytes. DNA from the purified cells was bisulfite-treated and analyzed at various CpG dinucleotide motifs. The inventors then compared the methylation status (finding C as for Cytosine that was methylated in the original (genomic) sequence versus T for cytosine that was unmethylated in the original sequence).

The data showed various CpG motifs and areas in the NKG7 gene that were demethylated in all NK cell samples while fully methylated in all other blood cell types. These data were generated in two steps: Initially, in a Golden Gate Illumina experiment, the inventors found differential methylation for a limited number of CpG, as indicated in table 2.

Then, upon finding the differential methylation in said Illumina experiment, the inventors further analyzed larger genomic regions by means of bisulfite sequencing. The latter procedure served for the exploring and extending of the differentially methylated regions and was conducted, for example with the differentially methylated gene regions of NKG7 as shown in FIG. 3. The primer sequences used to generate this particular amplicon are as follows:

```
                                    (SEQ ID NO: 42)
"1455p", "AAGGATTAGGAGAAGAAGGTTT"

(SEQ ID NO: 43)
"1455o", "TAAAACTATAAATCCCACCCAC"
```

Other similar amplicons generating differential methylation in this gene are generated by primers according to SEQ ID NOs: 160-181. Primer pairs are indicated with equal numbers, wherein a letter at the last position indicates the identity of the left or right primer.

Example 2

CX3CR1 Analysis

The inventors have purified various blood subsets including CD3/CD4, CD3/CD8 naïve and memory T lymphocytes, CD56 natural killer cells, CD19 naïve and memory B cells, CD14 monocytes and CD15 granulocytes. DNA from the purified cells was bisulfite-treated and analyzed at various CpG dinucleotide motifs. The inventors then compared the methylation status (finding C as for Cytosine that was methylated in the original (genomic) sequence versus T for cytosine that was unmethylated in the original sequence).

The data showed that various CpG motifs and areas in the CX3CR1 gene were demethylated in all NK cell samples while fully methylated in all other blood cell types. These data were generated in two steps: initially, in a Golden Gate Illumina experiment, differential methylation for a limited number of CpG was found, as indicated in table 2. Then, upon finding of the differential methylation in said Illumina experiment, the inventors analyzed larger genomic regions by means of bisulfite sequencing. This latter procedure served for the exploring and extending of the differentially methylated regions and was conducted, for example with the differentially methylated gene regions of CX3CR1 as shown in FIG. 1. The primer sequences used to generate this particular amplicon are as follows:

```
                                    (SEQ ID NO: 44)
"1452r", "ACACAACTCTTCTCCTCAAAAT"

(SEQ ID NO: 45)
"1452q", "TAGGGGTTAGGTAGGTAATGAA"
```

Other similar amplicons generating differential methylation in this gene are generated by primers according to SEQ ID NOs: 50 to 95. Primer pairs are named with equal numbers, wherein a letter at the last position indicates the identity of the left or right primer.

Example 3

FGR Analysis

The inventors have purified various blood subsets including CD3/CD4, CD3/CD8 naïve and memory T lymphocytes, CD56 natural killer cells, CD19 naïve and memory B cells, CD14 monocytes and CD15 granulocytes. DNA from the purified cells was bisulfite-treated analyzed at various CpG dinucleotide motifs. The inventors then compared the methylation status (finding C as for Cytosine that was methylated in the original (genomic) sequence versus T for cytosine that was unmethylated in the original sequence).

The data showed various CpG motifs and areas in the FGR gene that were demethylated in all NK cell samples while fully methylated in all other blood cell types. These data were generated in two steps: Initially, in a Golden Gate Illumina experiment, the inventors found differential methylation for a limited number of CpG, as indicated in table 2.

Then, upon finding of the differential methylation in said Illumina experiment, the inventors analysed larger genomic regions by means of bisulfite sequencing. This latter procedure served for exploring and extending the differentially methylated regions and was conducted, for example with the differentially methylated gene regions of FGR as shown in FIG. 2. The primer sequences used to generate this particular amplicon are as follows:

```
                                         (SEQ ID NO: 46)
"1454p", "ATGTGGGTAAATGAGGATGTAG"

(SEQ ID NO: 47)
"1454o", "CCAACCCCAAAAATATAAACAT"
```

Other similar amplicons generating differential methylation in this gene are generated by primers according to SEQ ID NOs: 96 to 137. Primer pairs are named with equal numbers, wherein a letter at the last position indicates the identity of the left or right primer.

Example 4

GNLY Analysis

The inventors have purified various blood subsets including CD3/CD4, CD3/CD8 nave and memory T lymphocytes, CD56 natural killer cells, CD19 naïve and memory B cells, CD14 monocytes and CD15 granulocytes. DNA from the purified cells was bisulfite-treated analyzed at various CpG dinucleotide motifs. The inventors then compared the methylation status (finding C as for Cytosine that was methylated in the original (genomic) sequence versus T for cytosine that was unmethylated in the original sequence).

The data showed various CpG motifs and areas in the GNLY gene that were demethylated in all NK cell samples while fully methylated in all other blood cell types. These data were generated in two steps: Initially, in a Golden Gate Illumina experiment, the inventors found differential methylation for a limited number of CpG, as indicated in table 2.

Then, upon finding of the differential methylation in said Illumina experiment, the inventors analyzed larger genomic regions by means of bisulfate sequencing. This latter procedure served for exploring and extending the differentially methylated regions and was conducted, for example with the differentially methylated gene regions of GNLY as shown in FIG. 4. The primer sequences used to generate this particular amplicon are as follows:

```
                                         (SEQ ID NO: 48)
"1458r", "ACCCTAAACTACTTCTTCACACA"

(SEQ ID NO: 49)
"1458q", "ATTGGATTAAGTTTGGTTTTGA"
```

Other similar amplicons generating differential methylation in this gene are generated by primers according to SEQ ID NOs: 138 to 159. Primer pairs are named with equal numbers, wherein a letter at the last position indicates the identity of the left or right primer.

---

The invention claimed is:

1. A method for identifying CD56-expressing natural killer cells in a sample derived from a human, wherein said method comprises the steps of:
   a) obtaining a sample comprising immune cells from said human,
   b) performing a nucleic acid based assay on the cells in the sample to determine the methylation status of at least one region of a GNLY gene, wherein the methylation status of the at least one region is determined by a method comprising amplifying the at least one region using a primer pair of SEQ ID NO: 146 and 147 and bisulfite sequencing, and
   c) identifying an immune cell in said sample as a CD56-expressing natural killer cell if the CpG positions in said at least one region as amplified are at least 90% demethylated as determined in step b).

2. The method according to claim 1, wherein determining the methylation status further comprises the use of a method selected from methylation specific enzymatic digests; analysis selected from CpG island methylation, MSP, HeavyMethyl, MethyLight, and Ms-SNu-PE; or other methods relying on a detection of amplified DNA.

3. The method according to claim 1, further comprising an analysis of the markers CD56, CD16 and/or CD8.

4. The method according to claim 1, wherein the step of identifying cells as the CD56-expressing natural killer cells comprises a distinction of said natural killer cells from all major peripheral blood cell types or non-blood cells.

5. The method according to claim 1, further comprising the step of evaluating an immune status of said human based on said natural killer cells as identified.

6. A method for monitoring a level of CD56-expressing natural killer cells in a human, comprising the method according to claim 1 and the method further comprising d) determining the amount of CD56-expressing natural killer cells identified in the sample and comparing the amount of CD56-expressing natural killer cells in the sample with an earlier sample taken from the same human and/or with a control sample.

7. The method according to claim 1, wherein said human suffers from or is likely to suffer from an autoimmune disease, transplant rejection, cancer, allergy and/or any disease directly correlated to NK cells.

8. The method according to claim 1, further comprising d) measuring and/or monitoring the amount of said CD56-expressing natural killer cells in response to chemical and/or biological substances that are provided to said human.

9. The method of according to claim 1, wherein the methylation status of at least one additional region is determined by amplifying the at least one additional region using a primer pair selected from SEQ ID NOs: 48 and 49 and SEQ ID NO: 148 and 149.

10. The method according to claim 1, wherein the immune cells are obtained from spleen, liver, peripheral blood, bone marrow, thymus, lymph node, or lymphatic fluid.

11. The method, according to claim 1, wherein said sample is a blood sample.

* * * * *